US011186623B2

(12) United States Patent
Lancaster et al.

(10) Patent No.: US 11,186,623 B2
(45) Date of Patent: Nov. 30, 2021

(54) ULTRA-LONG ACTING INSULIN-FC FUSION PROTEINS AND METHODS OF USE

(71) Applicant: Akston Biosciences Corporation, Beverly, MA (US)

(72) Inventors: Thomas M. Lancaster, Wenham, MA (US); Todd C. Zion, Marblehead, MA (US)

(73) Assignee: Akston Bioscience Corporation, Beverly, MA (US)

( * ) Notice: Subject to any disclaimer, the term of this patent is extended or adjusted under 35 U.S.C. 154(b) by 0 days.

(21) Appl. No.: 17/135,333

(22) Filed: Dec. 28, 2020

(65) Prior Publication Data
US 2021/0300983 A1  Sep. 30, 2021

Related U.S. Application Data

(60) Provisional application No. 62/953,470, filed on Dec. 24, 2019.

(51) Int. Cl.
*C07K 14/62* (2006.01)
*C12N 5/16* (2006.01)
*C07H 21/04* (2006.01)

(52) U.S. Cl.
CPC .............. *C07K 14/62* (2013.01); *C07H 21/04* (2013.01); *C07K 2319/30* (2013.01); *C07K 2319/70* (2013.01); *C12N 5/16* (2013.01)

(58) Field of Classification Search
CPC ..... C07K 16/62; C07K 2319/30; A61K 38/28
See application file for complete search history.

(56) References Cited

U.S. PATENT DOCUMENTS

| | | | |
|---|---|---|---|
| 8,933,207 | B2 | 1/2015 | Chen et al. |
| 9,074,015 | B2 | 7/2015 | Lancaster et al. |
| 9,855,318 | B2 | 1/2018 | Baldwin et al. |
| 10,597,435 | B2 | 3/2020 | Lancaster et al. |
| 10,709,766 | B2 | 7/2020 | Baldwin et al. |
| 10,822,386 | B2 | 11/2020 | Weiss |
| 10,851,147 | B2 | 12/2020 | Lancaster et al. |
| 10,870,686 | B2 | 12/2020 | Lancaster et al. |
| 10,894,089 | B2 | 1/2021 | Heo et al. |
| 10,947,292 | B2 | 3/2021 | Lancaster et al. |
| 10,961,294 | B2 | 3/2021 | Lancaster et al. |
| 2003/0040601 | A1 | 2/2003 | Diers et al. |
| 2012/0093814 | A1 | 4/2012 | Canada et al. |
| 2013/0142795 | A1 | 6/2013 | Bai et al. |
| 2013/0190475 | A1 | 7/2013 | Chen et al. |
| 2013/0190476 | A1 | 7/2013 | Lancaster et al. |
| 2014/0037699 | A1 | 2/2014 | Zion et al. |
| 2014/0302028 | A1 | 10/2014 | Zha |
| 2014/0357843 | A1 | 12/2014 | Oh et al. |
| 2016/0289290 | A1 | 10/2016 | Meehl et al. |
| 2016/0324932 | A1 | 11/2016 | Baldwin et al. |
| 2018/0009869 | A1 | 1/2018 | Lu et al. |
| 2018/0161448 | A1 | 6/2018 | Heo et al. |
| 2018/0177851 | A1 | 6/2018 | Baldwin et al. |
| 2018/0291076 | A1 | 10/2018 | Kjeldsen et al. |
| 2019/0315828 | A1 | 10/2019 | Lancaster et al. |
| 2019/0382439 | A1 | 12/2019 | Kim et al. |
| 2020/0131243 | A1 | 4/2020 | Lancaster et al. |
| 2020/0140516 | A1 | 5/2020 | Weiss |
| 2020/0140517 | A1 | 5/2020 | Weiss |
| 2020/0157169 | A1 | 5/2020 | Lancaster et al. |
| 2020/0157170 | A1 | 5/2020 | Lancaster et al. |
| 2020/0157171 | A1 | 5/2020 | Lancaster et al. |
| 2020/0231646 | A1 | 7/2020 | Lancaster et al. |
| 2020/0299343 | A1 | 9/2020 | Doerner et al. |
| 2020/0407413 | A1 | 12/2020 | Lancaster et al. |
| 2020/0407414 | A1 | 12/2020 | Lancaster et al. |

FOREIGN PATENT DOCUMENTS

| | | |
|---|---|---|
| CN | 101891823 | 11/2010 |
| CN | 101891823 A | 11/2010 |
| CN | 103509118 | 1/2014 |

(Continued)

OTHER PUBLICATIONS

Alleva, et al., "Immunological characterization and therapeutic activity of an altered-peptide ligand, NBI-6024, based an the immunodominant type 1 diabetes autoantigen insulin B-chain (9-23) peptide", Diabetes, 2002, 51(7) pp. 2126-2134.

Baeshen, et al., "Cell factories for insulin production", Microbial Cell Factories, 2014, 13(141).

Brüggemann, et al., "The immunogenicity of chimeric antibodies", Journal of Experimental Medicine, 1989,170(6) pp. 2153-2157.

Hua, et al., "Design of an Active Ultrastable Single-chain Insulin Analog", Journal of Biological Chemistry, 2008, 283 (21) pp. 14703-14716.

Strieizel, et al., "In Vitro functional characterization of feline IgGs", Veterinary Immunology and Immunopathology, 2014, 158(3-4) pp. 214-223 (abstract attached).

(Continued)

*Primary Examiner* — Gyan Chandra
(74) *Attorney, Agent, or Firm* — Hovey Williams LLP

(57) ABSTRACT

The present disclosure provides recombinantly manufactured ultra-long acting insulin-Fc fusion proteins for use in treating canine diabetes. The insulin-Fc fusion proteins comprise an insulin polypeptide linked via a peptide linker to an Fc-fragment of canine origin. Based on the results obtained, creating a treatment that is amenable to low cost manufacturing, exhibits sufficient in vivo bioactivity, displays extended duration of bioactivity, does not induce anti-drug antibodies, and substantially retains is potency over multiple administrations, requires a non-obvious combination of insulin polypeptide, peptide linkers, and species-specific Fc fragment, in addition to selective mutations on one or more of these components. Exemplary ultra-long acting insulin-Fc fusion proteins, polynucleotides encoding these insulin-Fc fusion proteins, and pharmaceutical formulations of exemplary insulin-Fc fusion proteins are provided, in addition to methods of use and preparation.

20 Claims, 11 Drawing Sheets
Specification includes a Sequence Listing.

(56) References Cited

FOREIGN PATENT DOCUMENTS

| | | |
|---|---|---|
| EP | 303380 | 2/1989 |
| EP | 3303380 | 4/2018 |
| EP | 3517544 | 7/2019 |
| EP | 2963056 | 11/2019 |
| EP | 3656792 | 5/2020 |
| WO | 2010/117760 | 10/2010 |
| WO | 2016044676 | 3/2016 |
| WO | 2016119023 | 8/2016 |
| WO | 2016177771 | 11/2016 |
| WO | 2016178905 | 11/2016 |
| WO | 2018009921 | 1/2018 |
| WO | 2018073185 | 4/2018 |
| WO | 2018107117 | 6/2018 |
| WO | 2019035010 | 2/2019 |
| WO | 2019204206 | 10/2019 |
| WO | 2020006529 | 1/2020 |
| WO | 2020070276 | 4/2020 |
| WO | 2020106748 | 5/2020 |
| WO | 2020236762 | 11/2020 |
| WO | 2021011827 | 1/2021 |
| WO | 2021022149 | 2/2021 |

OTHER PUBLICATIONS

Tang, et al., "Cloning and characterization of cDNAs encoding four different canine immunoglobulin γ chains", Veterinary Immunology and Immunopathology, 2001, 80(3-4) pp. 259-270 (abstract attached).

Terada, et al., "A chimeric human-cat Fcγ-Fel d1 fusion protein inhibits systemic, pulmonary, and cutaneous allergic reactivity to intratracheal cachallenge in mice sensitized to Fel d1, the major cat allergen", Clinical Immunology, 2006, 120(1) pp. 45-56 (abstract attached).

Wang, et al., "Proinsulin-Transferrin Fusion Protein as a Novel Long-Acting Insulin Analog for the Inhibition of Hepatic Glucose Production", Diabetes, 2014, 63 pp. 1779-1788.

Wang, et al., "IgG Fc engineering to modulate antibody effector functions", Protein Cell, Jan. 2018, 9(1), pp. 63-73.

Kim, et al., "Mammalian cell transfection: the present and the future", Analytical and Bioanalytical Chemistry, 2010, 397(8), pp. 3173-3178.

Fan, et al., "Improving the efficiency of CHO cell line generation using glutamine synthetase gene knockout cells", Biotechnology and Bioengineering, 2012, 109(4), pp. 1007-1015 (abstract attached).

Lodish, et al.,Molecular Cell Biology, Molecular Cell Biology, 4th edition, 2000, www.ncbi.nlm.gov/ books/NBK21654 (abstract attached).

Horvath, et al., "An automated DNA synthesizer employing deoxynucleoside 3'-phosphoramidites", Methods in Enzymology, Academic Press, 1987, 154, pp. 314-326 (abstract attached).

Dumont, et al., "Human cell lines for biopharmaceutical manufacturing: history, status, and future perspectives", Critical Reviews in Biotechnology, 2016, 36(6), pp. 1110-1122.

Singh, et al., "Combined blockade of HER2 and VEGF exerts greater growth inhibition of HER2-overexpressing gastric cancer xenografts than individual blockade", Experimental and Molecular Medicine, 2013, 45, 11 pages.

Huang, et al., "Production of recombinant murine-human chimeric IgM and IgG anti-Jsb for use in the clinical laboratory". Transfusion, 2003, 43(6), pp. 758-764 (abstract attached).

yourgenome.org, "What does DNA do?", 2016, https://www.yourgenome.org/facts/what-does-dna-do.

```
SEQ ID NO: 33    FVNQHLCGSDLVEALALVCGERGFFYTDPTGG-GPRRGIVEQCCHSICSLYQLENYCNGG  59
SEQ ID NO: 35    FVNQHLCGSDLVEALYLVCGERGFFYTDPTGG-GPRRGIVEQCCHSICSLYQLENYCNGG  59
SEQ ID NO: 37    FVNQHLCGSHLVEALYLVCGERGFFYTPKAGG-GPRRGIVEQCCTSICSLYQLENYCNGG  59
SEQ ID NO: 39    FVNQHLCGSHLVEALYLVCGERGFFYTPKAAAAAAAKGIVEQCCTSICSLYQLENYCNGG  60
                 ********.***** ***********   :.. .:****** *****************

SEQ ID NO: 33    GGAGGGGRCTDTPPCPVPEPLGGPSVLIFPPKPKDILRITRTPEVTCVVLDLGREDPEVQ  119
SEQ ID NO: 35    GGSGGGGRCTDTPPCPVPEPLGGPSVLIFPPKPKDILRITRTPEVTCVVLDLGREDPEVQ  119
SEQ ID NO: 37    GGSGGGGRCTDTPPCPVPEPLGGPSVLIFPPKPKDILRITRTPEVTCVVLDLGREDPEVQ  119
SEQ ID NO: 39    GGSGGGGRCTDTPPCPVPEPLGGPSVLIFPPKPKDILRITRTPEVTCVVLDLGREDPEVQ  120
                 **:*********************************************************

SEQ ID NO: 33    ISWFVDGKEVHTAKTQSREQQFNGTYRVVSVLPIEHQDWLTGKEFKCRVNHIDLPSPIER  179
SEQ ID NO: 35    ISWFVDGKEVHTAKTQSREQQFNGTYRVVSVLPIEHQDWLTGKEFKCRVNHIDLPSPIER  179
SEQ ID NO: 37    ISWFVDGKEVHTAKTQSREQQFNGTYRVVSVLPIEHQDWLTGKEFKCRVNHIDLPSPIER  179
SEQ ID NO: 39    ISWFVDGKEVHTAKTQSREQQFNGTYRVVSVLPIEHQDWLTGKEFKCRVNHIDLPSPIER  180
                 ************************************************************

SEQ ID NO: 33    TISKARGRAHKPSVYVLPPSPKELSSSDTVSITCLIKDFYPPDIDVEWQSNGQQEPERKH  239
SEQ ID NO: 35    TISKARGRAHKPSVYVLPPSPKELSSSDTVSITCLIKDFYPPDIDVEWQSNGQQEPERKH  239
SEQ ID NO: 37    TISKARGRAHKPSVYVLPPSPKELSSSDTVSITCLIKDFYPPDIDVEWQSNGQQEPERKH  239
SEQ ID NO: 39    TISKARGRAHKPSVYVLPPSPKELSSSDTVSITCLIKDFYPPDIDVEWQSNGQQEPERKH  240
                 ************************************************************

SEQ ID NO: 33    RMTPPQLDEDGSYFLYSKLSVDKSRWQQGDPFTCAVMHETLQNHYTDLSLSHSPG      294
SEQ ID NO: 35    RMTPPQLDEDGSYFLYSKLSVDKSRWQQGDPFTCAVMHETLQNHYTDLSLSHSPG      294
SEQ ID NO: 37    RMTPPQLDEDGSYFLYSKLSVDKSRWQQGDPFTCAVMHETLQNHYTDLSLSHSPG      294
SEQ ID NO: 39    RMTPPQLDEDGSYFLYSKLSVDKSRWQQGDPFTCAVMHETLQNHYTDLSLSHSPG      295
                 *******************************************************
```

FIG. 3

```
SEQ ID NO: 41    FVNQHLCGSDLVEALALVCGERGFFYTDPTGGGPRRGIVEQCCHSICSLYQLENYCNGGG  60
SEQ ID NO: 47    FVNQHLCGSDLVEALALVCGERGFFYTDPTGGGPRRGIVEQCCHSICSLYQLENYCNGGG  60
SEQ ID NO: 49    FVNQHLCGSHLVEALALVCGERGFFYTDPTGGGPRRGIVEQCCTSICSLYQLENYCNGGG  60
SEQ ID NO: 51    FVNQHLCGSDLVEALALVCGERGFFYTDPTGGGPRRGIVEQCCHSICSLYQLENYCNGGG  60
                 ********* ***************************** ** ****************

SEQ ID NO: 41    GAGGGGDCPKCPAPEMLGGPSVFIFPPKPKDTLLIARTPEVTCVVVDLDPEDPEVQISWF  120
SEQ ID NO: 47    GAGGGGDCPKCPAPEMLGGPSVFIFPPKPKDTLLIARTPEVTCVVVDLDPEDPEVQISWF  120
SEQ ID NO: 49    GAGGGGDCPKCPAPEMLGGPSVFIFPPKPKDTLLIARTPEVTCVVVDLDPEDPEVQISWF  120
SEQ ID NO: 51    GAGG-GGCPKCPAPEMLGGPSVFIFPPKPKDTLLIARTPEVTCVVVDLDPEDPEVQISWF  119
                 ****  *****************************************************

SEQ ID NO: 41    VDGKQMQTAKTQPREEQFNGTYRVVSVLPIGHQDWLKGKQFTCKVNNKALPSPIERTISK  180
SEQ ID NO: 47    VDGKQMQTAKTQPREEQFSGTYRVVSVLPIGHQDWLKGKQFTCKVNNKALPSPIERTISK  180
SEQ ID NO: 49    VDGKQMQTAKTQPREEQFQGTYRVVSVLPIGHQDWLKGKQFTCKVNNKALPSPIERTISK  180
SEQ ID NO: 51    VDGKQMQTAKTQPREEQFKGTYRVVSVLPIGHQDWLKGKQFTCKVNNKALPSPIERTISK  179
                 ****************** ****************************************

SEQ ID NO: 41    ARGQAHQPSVYVLPPSREELSKNTVSLTCLIKDFFPPDIDVEWQSNGQQEPESKYRTTPP  240
SEQ ID NO: 47    ARGQAHQPSVYVLPPSREELSKNTVSLTCLIKDFFPPDIDVEWQSNGQQEPESKYRTTPP  240
SEQ ID NO: 49    ARGQAHQPSVYVLPPSREELSKNTVSLTCLIKDFFPPDIDVEWQSNGQQEPESKYRTTPP  240
SEQ ID NO: 51    ARGQAHQPSVYVLPPSREELSKNTVSLTCLIKDFFPPDIDVEWQSNGQQEPESKYRTTPP  239
                 ************************************************************

SEQ ID NO: 41    QLDEDGSYFLYSKLSVDKSRWQRGDTFICAVMHEALHNHYTQESLSHSPG         290
SEQ ID NO: 47    QLDEDGSYFLYSKLSVDKSRWQRGDTFICAVMHEALHNHYTQESLSHSPG         290
SEQ ID NO: 49    QLDEDGSYFLYSKLSVDKSRWQRGDTFICAVMHEALHNHYTQESLSHSPG         290
SEQ ID NO: 51    QLDEDGSYFLYSKLSVDKSRWQRGDTFICAVMHEALHNHYTQESLSHSPG         289
                 **************************************************
```

FIG. 4

```
atg gaa tgg agc tgg gtc ttt ctc ttc ttc ctg tca gta acg act ggt gtc cac tcc ttc
 M   E   W   S   W   V   F   L   F   F   L   S   V   T   T   G   V   H   S   F
                              (SEQ ID NO: 54)

gtg aac cag cac ctg tgc ggc tcc gac ctg gtg gaa gct ctg gct ctc gtg tgc ggc gag
 V   N   Q   H   L   C   G   S   D   L   V   E   A   L   A   L   V   C   G   E cgg ggc ttc ttc tac acc gat ccc act gga ggc ggt cca cgc aga ggc atc gtg gaa cag
 R   G   F   F   Y   T   D   P   T   G   G   G   P   R   R   G   I   V   E   Q tgc tgc cac tcc atc tgc tcc ctg tac cag ctg gaa aac tac tgc aat ggc gga ggt ggt
 C   C   H   S   I   C   S   L   Y   Q   L   E   N   Y   C   N   G   G   G   G gca gga ggc ggt gga tgc ccc aag tgc ccc gct ccc gag atg ctg ggc gga ccc agc gtg
 A   G   G   G   G   C   P   K   C   P   A   P   E   M   L   G   G   P   S   V ttc atc ttc cct ccc aag ccc aag gac aca ctg ctg atc gcc agg acc ccg gag gtg acc
 F   I   F   P   P   K   P   K   D   T   L   L   I   A   R   T   P   E   V   T tgc gtg gtg gtg gac ctg gat ccc gaa gac ccc gag gtg cag atc agc tgg ttc gtg gat
 C   V   V   V   D   L   D   P   E   D   P   E   V   Q   I   S   W   F   V   D gga aag cag atg cag acc gcc aag acc caa ccc cgg gaa gag cag ttc aaa ggc acc tac
 G   K   Q   M   Q   T   A   K   T   Q   P   R   E   E   Q   F   K   G   T   Y agg gtg gtg agt gtg ttg ccc atc ggc cac cag gac tgg ctg aag ggg aag caa ttc aca
 R   V   V   S   V   L   P   I   G   H   Q   D   W   L   K   G   K   Q   F   T tgc aag gtt aat aac aag gcc ctg ccc agc ccc atc gag agg acc atc agc aag gcc agg
 C   K   V   N   N   K   A   L   P   S   P   I   E   R   T   I   S   K   A   R ggc cag gcc cac cag cca tct gtg tac gtg ctg ccc cca tct agg gag gaa ctg agc aag
 G   Q   A   H   Q   P   S   V   Y   V   L   P   P   S   R   E   E   L   S   K aac aca gtc agc ctt act tgc ctg atc aag gac ttc ttc cca ccg gac ata gac gtg gag
 N   T   V   S   L   T   C   L   I   K   D   F   F   P   P   D   I   D   V   E tgg cag agt aac ggc cag cag gag ccc gag agc aag tat agg acc aca ccg ccc caa ctg
 W   Q   S   N   G   Q   Q   E   P   E   S   K   Y   R   T   T   P   P   Q   L gac gag gac gga agc tac ttc ctc tac agc aaa ttg agc gtt gac aaa agc agg tgg cag
 D   E   D   G   S   Y   F   L   Y   S   K   L   S   V   D   K   S   R   W   Q cga ggc gac acc ttc atc tgc gcc gtg atg cac gag gct ttg cat aac cac tac acc cag
 R   G   D   T   F   I   C   A   V   M   H   E   A   L   H   N   H   Y   T   Q gag agc ctg tcc cac agc ccc gga tag (SEQ ID NO: 52)
 E   S   L   S   H   S   P   G   -  (SEQ ID NO: 51)
```

Fig. 12

ULTRA-LONG ACTING INSULIN-FC FUSION PROTEINS AND METHODS OF USE

PRIORITY AND RELATED APPLICATIONS

The present application is related to and claims the priority benefit of U.S. Patent Application Ser. No. 62/953,470, filed Dec. 24, 2019. The contents of the aforementioned patent application are hereby incorporated herein by reference in their entirety.

TECHNICAL FIELD

The present technology relates to compositions of insulin-Fc fusion proteins and their use to treat diabetes in companion animals, e.g., dogs.

BACKGROUND

The following description of the background of the present technology is provided simply as an aid in understanding the present technology and is not admitted to describe or constitute prior art to the present technology.

Diabetes is a chronic condition characterized by an insulin deficiency and/or ineffective use of insulin. Diabetics that have an absolute deficiency of insulin are categorized as having type 1 or insulin-dependent diabetes mellitus (IDDM). Type 1 diabetics are thought to have a genetic predisposition combined with immunologic destruction of the insulin-producing β-cells of the pancreas. In comparison, diabetics that can still produce some insulin but have a relative deficiency due to insulin resistance or other dysfunction, are classified as having type 2 or non-insulin-dependent diabetes mellitus (NIDDM). Type 2 diabetes is linked to genetic predisposition, obesity, and certain medications.

When a dog does not produce insulin or cannot use it normally, blood sugar levels elevate, resulting in hyperglycemia. Dogs generally exhibit an atypical glycemia phenotype with strong similarities to human type 1 diabetes. Dogs also occasionally exhibit atypical glycemia with strong similarities to type 2 diabetes in humans. Female dogs can also develop temporary insulin resistance while in heat or pregnant. In all cases, the dogs are treated with chronic insulin injection therapy. Left untreated, diabetes in dogs can lead to weight loss, loss of appetite, vomiting, dehydration, problems with motor function, coma, and even death.

Approximately 0.24% of dogs in the United States are affected by diabetes. Current diabetes therapies for dogs include the use of insulin, such as Vetsulin® for dogs (Intervet Inc., d.b.a. MERCK Animal Health, Summit, N.J.) which is administered once or twice daily. The burden of frequent injections on owners often results in a lack of treatment regimen compliance and under-dosing, leading to poor long-term health outcomes. In fact, the cost of insulin therapy and the practicality of dosing their pets up to 14 times per week leads a significant percentage of owners to select euthanasia for their pets as an alternative to intensive management of diabetes. Therefore, there is a need for cost effective and less burdensome treatment options for this disease.

SUMMARY OF THE PRESENT TECHNOLOGY

In an aspect, the present disclosure provides a fusion protein comprising an insulin polypeptide and an Fc fragment, wherein the insulin polypeptide and the Fc fragment are connected by a linker, such as a peptide linker, wherein the Fc fragment comprises one or more mutations to prevent natural glycosylation.

In one embodiment, the Fc fragment comprises the sequence:

```
                                            (SEQ ID NO: 32)
CPKCPAPEMLGGPSVFIFPPKPKDTLLIARTPEVTCVVVDLDPEDPEVQ

ISWFVDGKQMQTAKTQPREEQFKGTYRVVSVLPIGHQDWLKGKQFTCKV

NNKALPSPIERTISKARGQAHQPSVYVLPPSREELSKNTVSLTCLIKDF

FPPDIDVEWQSNGQQEPESKYRTTPPQLDEDGSYFLYSKLSVDKSRWQR

GDTFICAVMHEALHNHYTQESLSHSPG.
```

In some embodiments, the insulin polypeptide comprises a C-peptide of the sequence: GGGPRR (SEQ ID NO: 8).

In an embodiment, the present disclosure provides for a fusion protein comprising an insulin polypeptide and an Fc fragment, wherein the insulin polypeptide and the Fc fragment are connected by a linker (e.g., peptide linker), and wherein the fusion protein comprises the sequence:

```
                                            (SEQ ID NO: 51)
FVNQHLCGSDLVEALALVCGERGFFYTDPTGGGPRRGIVEQCCHSICSL

YQLENYCNGGGGAGGGGCPKCPAPEMLGGPSVFIFPPKPKDTLLIARTP

EVTCVVVDLDPEDPEVQISWFVDGKQMQTAKTQPREEQFKGTYRVVSVL

PIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDG

SYFLYSKLSVDKSRWQRGDTFICAVMHEALHNHYTQESLSHSPG.
```

In embodiments, the fusion protein comprises a dimer, wherein the dimer comprises two identical monomers bound together via disulfide bonds, e.g., the fusion protein is a homodimer. In some embodiments, the percentage homodimer of insulin-Fc fusion protein is greater than 90%.

In embodiments, the fusion proteins described herein are made using HEK293 cells, and the resulting homodimer titer after purification using Protein A beads or a Protein A column is greater than 40 mg/L. In embodiments, the insulin receptor IC50 for the fusion proteins described herein is less than or equal to 5000 nM. In embodiments, the serum half-life of the fusion proteins described herein in the blood or serum of a target animal upon administration is longer than about 3 days. In embodiments, for the fusion proteins described herein, the time during which there is a statistically significant decrease in blood glucose level in a subject relative to a pre-dose level is longer than one of 2 hours, 6 hours, 9 hours, 12 hours, 18 hours, 1 day, 1.5 days, 2 days, 2.5 days, 3 days, 4 days, 5 days, 6 days, 7 days, or longer.

In aspects, for the fusion proteins described herein, the NAOC after the first subcutaneous injection in a target animal is greater than 150% FBGL·days·kg/mg. In embodiments, for the fusion proteins described herein, the ratio of the NAOC after the third weekly subcutaneous injection of the fusion proteins in the target animal to the NAOC after the first subcutaneous injection of the fusion protein in the target animal is greater than 0.50.

In aspects, fusion proteins as described herein are formulated as a pharmaceutical composition. In embodiments, in the pharmaceutical composition the fusion protein is present at a concentration of about 3 mg/mL or greater. In embodiments, the composition is suitable for subcutaneous administration.

In aspects, a method is described for lowering the blood glucose level of a dog, the method comprising administering a physiologically effective amount of a fusion protein as described herein or a pharmaceutical composition thereof to the dog. In embodiments, the dog is diagnosed with diabetes. In some embodiments, the fusion protein is administered subcutaneously. In some embodiments, the fusion protein is administered daily, twice weekly, or once weekly to the dog. In examples, the fusion protein is administered once weekly to the dog at a dose between 0.025 and 0.5 mg/kg/week. In aspects, a cell engineered to express a fusion protein as described here in described. In examples, the cell is transfected with a nucleic acid encoding the fusion protein. In examples, the cell is a HEK293 cell or a CHO cell.

In an aspect, a cDNA encoding a fusion protein as described herein is described. In embodiments, the cDNA comprises the nucleic acid sequence encoding the insulin-Fc fusion protein of SEQ ID NO: 51):) where the leader sequence is underlined:

(SEQ ID NO: 52)
<u>atggaatggagctgggtctttctcttcttcctgtcagtaacgactggtg</u>
tccactccttcgtgaaccagcacctgtgcggctccgacctggtggaagc
tctggctctcgtgtgcggcgagcggggcttcttctacaccgatcccact
ggaggcggtccacgcagaggcatcgtggaacagtgctgccactccatct
gctccctgtaccagctggaaaactactgcaatggcggaggtggtgcagg
aggcggtggatgccccaagtgcccgctcccgagatgctgggcggaccc
agcgtgttcatcttccctcccaagcccaaggacacactgctgatcgcca
ggaccccggaggtgacctgcgtggtggtggacctggatcccgaagacc
cgaggtgcagatcagctggttcgtggatggaaagcagatgcagaccgcc
aagacccaacccgggaagagcagttcaaaggcacctacagggtggtga
gtgtgttgcccatcggccaccaggactggctgaaggggaagcaattcac
atgcaaggttaataacaaggccctgcccagcccatcgagaggaccatc
agcaaggccaggggccaggcccaccagccatctgtgtacgtgctgcccc
catctaggaggaactgagcaagaacacagtcagccttacttgcctgat
caaggacttcttcccaccggacatagacgtggagtggcagagtaacggc
cagcaggagcccgagagcaagtataggaccacaccgcccaactggacg
aggacggaagctacttcctctacagcaaattgagcgttgacaaaagcag
gtggcagcgaggcgacaccttcatctgcgccgtgatgcacgaggctttg
cataaccactacacccaggagagcctgtcccacgccccggatag.

BRIEF DESCRIPTION OF THE DRAWINGS

FIG. 3 illustrates a side-by-side sequence comparison of SEQ ID NO: 33, SEQ ID NO: 35, SEQ ID NO: 37 and SEQ ID NO: 39. "*" represents complete homology across all sequences at a given sequence position, while ":", "." or spaces refer to conservative, moderate, or very different amino acid mutations across the sequences at a given sequence position respectively.

FIG. 4 illustrates a side-by-side sequence comparison of SEQ ID NO: 41, SEQ ID NO: 47, SEQ ID NO: 49 and SEQ ID NO: 51. "*" represents complete homology across all sequences at a given sequence position, while ":", "." or spaces refer to conservative, moderate, or very different amino acid mutations across the sequences at a given sequence position respectively.

FIG. 12 illustrates the "full aa sequence" of a fusion protein (SEQ ID NO: 51) and its corresponding nucleic acid sequence (SEQ ID NO: 52).

DETAILED DESCRIPTION

Figure 1:
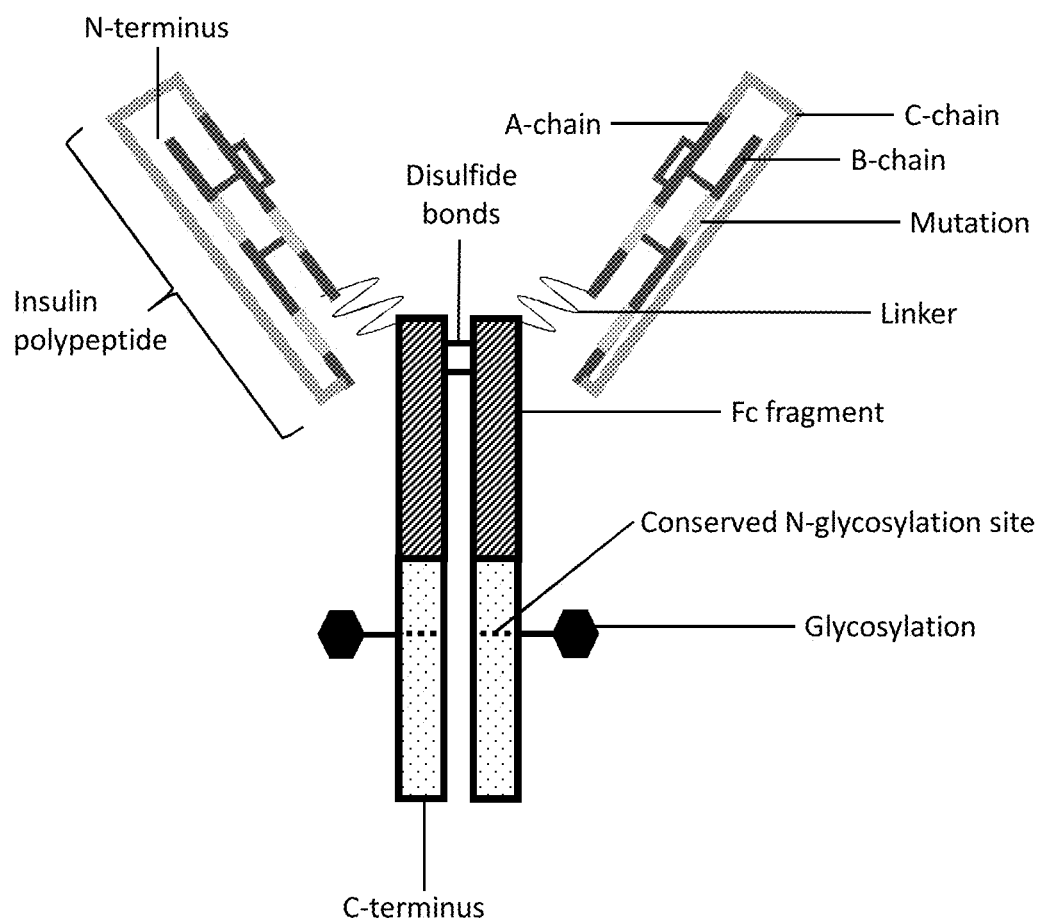
FIG. 1 shows a schematic representation of an exemplary insulin-Fc fusion protein homodimer.

An insulin treatment that requires less frequent dosing (e.g., once-weekly injections) would be less burdensome on the owners, leading to better compliance, fewer instances of euthanasia, and better outcomes for the pets. As disclosed herein, proposed ultra-long acting insulin treatments for veterinary clinical use comprise an insulin-Fc fusion protein making use of an Fc fragment to prolong their action in vivo. An insulin-Fc fusion protein suitable for an ultra-long acting treatment for diabetes should meet various design goals. An insulin-Fc fusion protein configuration suitable for an ultra-long acting treatment for diabetes in dogs should be manufacturable in mammalian cells, for example human embryonic kidney (HEK, e.g. HEK293) cells, with an acceptable titer of the desired homodimer product (e.g., greater than 40 mg/L homodimer titer from transiently transfected HEK cells, greater than 75 mg/L from transiently transfected from HEK cells, greater than 100 mg/L from transiently transfected HEK cells, etc.). Only candidates with a homodimer titer of greater than 40 mg/L from transiently transfected HEK cells are considered useful in the present invention, because experience has demonstrated that homodimer titers less than this level will not likely result in commercial production homodimer titers in Chinese hamster ovary (CHO) cells that meet the stringently low manufacturing cost requirements for veterinary products.

In addition, the molecule must bind the insulin receptor with an appreciable affinity (e.g., IC50 less than 5000 nM, IC50 less than 4000 nM, IC50 less than 3000 nM, IC50 less than 2500 nM, etc.) as measured in the 4° C. IM-9 insulin receptor binding assay. Based on experience, only molecules exhibiting insulin receptor activity IC50 values less than 5000 nM are deemed likely to exhibit the requisite bioactivity in the target species. The molecule must also demonstrate sustained bioactivity in vivo (e.g., demonstrate glucose lowering activity greater than about 2 hours, 6 hours, 9 hours, 12 hours, 18 hours, 1 day, 1.5 days, 2 days, 2.5 days, 3 days, 4 days, 5 days, 6 days, 7 days, or longer) to justify less frequent dosing. The molecule must also demonstrate prolonged system residence time in the target animal (e.g., the serum half-life must be greater than 3 days, or longer). The bioactive potency and duration of the bioactivity may be quantitatively represented by calculating the area over the percent fasting blood glucose (% FBGL) curve normalized to a given dose in mg/kg (NAOC) with units of % FBGL·days·kg/mg as described in Example 15. The NAOC increases with a greater drop in % FBGL, which is the case where the molecule demonstrates increased bioactivity, and when the % FBGL takes longer to return to 100%, which is the case where the insulin-Fc fusion protein demonstrates increased duration of action. To be useful as described herein, a molecule must demonstrate a sufficiently high NAOC value (e.g. preferably NAOC greater than 150% FBGL·days·kg/mg, more preferably NAOC greater than 200% FBGL·days·kg/mg, and even more preferably NAOC greater than 250% FBGL·days·kg/mg). Based on experience, at NAOC values greater than 150% FBGL·days·kg/mg, the dose requirements in the target species will be sufficiently low so as to reach an acceptable treatment cost.

Proposed ultra-long acting insulin treatments for veterinary clinical use in dogs comprise an insulin-Fc fusion protein making use of an Fc fragment to prolong the action in vivo.

Provided herein, therefore, are manufacturable, high purity, long-acting, bioactive, insulin-Fc fusion protein configurations comprising an insulin polypeptide, an Fc fragment, and a linker between the insulin polypeptide and the Fc fragment, and which exhibit acceptably high homodimer titers (e.g., homodimer titers greater than 40 mg/L), acceptable IR binding (e.g., insulin receptor activity IC50 less than 5000 nM, IC50 less than 4000 nM, IC50 less than 3000 nM, IC50 less than 2500 nM, etc.) and/or acceptable bioactivity in vivo (e.g., NAOC values greater than 150% FBGL·days·kg/mg). These exemplary insulin-Fc fusion protein configurations are expected to exhibit sufficiently high insulin receptor binding and a long enough half-life to justify repeated once-a-week dosing, rendering them suitable for the treatment of diabetes in dogs.

Definitions

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., insulin) having a chemical structure similar to that of another compound or conjugate but differing from it in at least one aspect.

As used herein, the term "antibody" or "antibody molecule" refers to an immunoglobulin molecule (Ig), immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. It is documented in the art that antibodies comprise several classes, for example IgA, IgM, or IgG in the case of mammals (e.g., humans and dogs). Classes of immunoglobulins can be further classified into different isotypes, such as IgGA, IgGB, IgGC, and IgGD for canines. Those skilled in the art will recognize that immunoglobulin isotypes of a given immunoglobulin class will comprise different amino acid sequences, structures, and functional properties from one another (e.g., different binding affinities to Fc(gamma) receptors). "Specifically binds" or "immunoreacts with" means that the antibody reacts with one or more antigenic determinants of the desired antigen and has a lower affinity for other polypeptides, e.g., does not react with other polypeptides.

As used herein, the term "area-under-the-curve" or "AUC" refers to the integrated area under the % FBGL vs. time curve for a subject after a given dose of an insulin-Fc fusion protein configuration is administered. As used herein, the term "area-over-the curve" or "AOC" is used as a measure of the biological potency of an insulin-Fc fusion protein configuration such that the AOC equals the difference between the total possible area under the % FBGL vs. time curve and the AUC value. As used herein, the "normalized area-over-the curve," "normalized AOC," or "NAOC" is the AOC value divided by the actual dose of insulin-Fc fusion protein administered. As used herein, the term "normalized AOC ratio" or "NAOCR" is the ratio of the NAOC resulting from a particular administration of an insulin-Fc fusion protein to the NAOC resulting from the first administration of an insulin-Fc fusion protein in a series of administrations. The NAOCR thus provides a measure of the change in biological activity of an insulin-Fc fusion protein after repeated administrations.

As used herein, the term "bioactivity," "activity," "biological activity," "potency," "bioactive potency," or "biological potency" refers to the extent to which an insulin-Fc fusion protein activates the insulin receptor and/or exerts a reduction in blood glucose levels in a target subject. As used herein, "in vitro activity" or "insulin receptor activity" refers to the affinity with which an insulin-Fc fusion protein binds to the insulin receptor and is typically measured by the concentration at which an insulin-Fc fusion protein displaces half of an insulin reference standard from the insulin receptor in a competitive binding assay (i.e., IC50). As used herein, "in vivo activity" refers to the extent and duration of reduction in a target subject's fasting blood glucose level after administration of an insulin-Fc fusion protein.

As used herein, the term "biosynthesis," "recombinant synthesis," or "recombinantly made" refers to the process by which an insulin-Fc fusion protein is expressed within a host cell by transfecting the cell with a nucleic acid molecule (e.g., vector) encoding the insulin-Fc fusion protein (e.g., where the entire insulin-Fc fusion protein is encoded by a single nucleic acid molecule). Exemplary host cells include mammalian cells, e.g., HEK293 cells or CHO cells. The cells can be cultured using standard methods in the art and the expressed insulin-Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a hormone receptor (e.g., an insulin hormone receptor or insulin receptor (IR)) or an Fc receptor which binds to an Fc fragment or the Fc region of an antibody (e.g. an Fc(gamma) receptor, for example Fc(gamma) receptor I, or an Fc neonatal receptor, for example FcRn). As used herein, "in vitro activity" or "Fc(gamma) receptor activity" or "Fc(gamma) receptor binding" or "FcRn receptor activity" or "FcRn binding" refers to the affinity with which an insulin-Fc fusion protein binds to the Fc receptor (e.g. Fc(gamma) receptor or FcRn receptor) and is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader. Alternatively, the affinity with which an insulin-Fc fusion protein binds to the Fc receptor (e.g. Fc(gamma) receptor or FcRn receptor) is measured by the OD 450 nm value obtained on a microplate reader in an enzyme-linked immunosorbent assay (ELISA) assay at a given concentration of the insulin-Fc fusion protein.

As used herein, the term "fasting blood glucose level" or "FBGL" refers to the average blood glucose level in a target subject at the end of a period during which no food is administered and just prior to the time at which an insulin-Fc fusion protein is administered. As used herein, the term "percent fasting blood glucose level," "% fasting blood glucose level," or "% FBGL" refers to the ratio of a given blood glucose level to the fasting blood glucose level multiplied by 100.

As used herein, the term "immunogenic" or "immunogenicity" refers to the capacity for a given molecule (e.g., an insulin-Fc fusion protein of the present invention) to provoke the immune system of a target subject.

As used herein, the term "insulin reference standard" is any one of: (i) a naturally occurring insulin from a mammal (e.g., a human or dog); (ii) an insulin polypeptide that does not comprise an Fc fragment; or (iii) a standard of care insulin (e.g., a commercially available insulin).

As used herein, the term "monomer" refers to a protein or a fusion protein comprising a single polypeptide. In embodiments, the "monomer" is a protein or a fusion protein, e.g., a single polypeptide, comprising an insulin polypeptide and an Fc fragment polypeptide, wherein the insulin polypeptide and Fc fragment polypeptide are joined by a peptide linker to form the single polypeptide. In embodiments, the monomer is encoded by a single nucleic acid molecule.

As used herein, "N-terminus" refers to the start of a protein or polypeptide that is initiated by an amino acid containing a free amine group that is the alpha-amino group of the amino acid (e.g. the free amino that is covalently linked to one carbon atom that is located adjacent to a second carbon atom, wherein the second carbon atom is part of the carbonyl group of the amino acid). As used herein, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, "pharmacodynamics" or "PD" generally refers to the biological effects of an insulin-Fc fusion protein in a subject. Specifically, herein the PD refers to the measure of the reduction in fasting blood glucose level over time in a subject after the administration of an insulin-Fc fusion protein.

As used herein, "pharmacokinetics" or "PK" generally refers to the characteristic interactions of an insulin-Fc fusion protein and the body of the subject in terms of its absorption, distribution, metabolism, and excretion. Specifically, herein the PK refers to the concentration of an insulin-Fc fusion protein in the blood or serum of a subject at a given time after the administration of the insulin-Fc fusion protein. As used herein, "half-life" refers to the time taken for the concentration of insulin-Fc fusion protein in the blood or serum of a subject to reach half of its original value as calculated from a first order exponential decay model for drug elimination. Insulin-Fc fusion proteins with greater "half-life" values demonstrate greater duration of action in the target subject.

The terms "sequence identity" "sequence homology" "homology" or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences. See, for example Ausubel et al., eds. (1995) *Current Protocols in Molecular Biology*, Chapter 19 (Greene Publishing and Wiley-Interscience, New York); and the ALIGN program (Dayhoff (1978) in Atlas of Polypeptide Sequence and Structure 5: Suppl. 3 (National Biomedical Research Foundation, Washington, D.C.). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is described in Smith and Waterman (1981) *Adv. Appl. Math* 2:482-489, herein incorporated by reference. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" or "target subject" or "patient" or "patient subject" are intended to include canines. Exemplary canine subjects include dogs having a disease or a disorder, e.g., diabetes or another disease or disorder described herein, or normal subjects.

As used herein, the term "titer" or "yield" refers to the amount of a fusion protein product (e.g., an insulin-Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of insulin-Fc fusion protein expressed by cells and purified via at least one affinity chromatography step (e.g. Protein A or Protein G) and includes monomers of insulin-Fc fusion protein, homodimers of insulin-Fc fusion protein, and higher-order molecular aggregates of homodimers of insulin-Fc fusion protein. As used herein, the term "percent homodimer" or "% homodimer" refers to the proportion of a fusion protein product (e.g., an insulin-Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" a subject having a disease or a disorder refer to subjecting the subject to a regimen, for example the administration of a fusion protein such as a fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve or affect the disease or disorder, or the symptoms of the disease or disorder. The treatment may inhibit deterioration or worsening of a symptom of a disease or disorder.

Insulin-Fc Fusion Protein Components and Structure

The present disclosure relates to a composition of a fusion protein (i.e., an insulin-Fc fusion protein) comprising an insulin polypeptide linked via a peptide linker to a species-specific Fc fragment, and its use to treat diabetes in dogs. As used herein, the terms "fusion protein" and "insulin-Fc fusion protein" refer to a protein comprising more than one part, for example from different sources (different proteins, polypeptides, cells, etc.), that are covalently linked through peptide bonds. The insulin-Fc fusion proteins are covalently linked by (i) connecting the genes that encode for each part into a single nucleic acid molecule and (ii) expressing in a host cell (e.g., HEK or CHO) the protein for which the nucleic acid molecule encodes as follows: (N-terminus)-insulin polypeptide-linker-Fc fragment-(C-terminus). The fully recombinant synthesis approach is preferred over methods in which the insulin polypeptide and Fc fragments are synthesized separately and then chemically conjugated. The chemical conjugation step and subsequent purification process increase the manufacturing complexity, reduce product yield, and increase cost.

As used herein, the term "dimer" refers to a protein or a fusion protein comprising two polypeptides linked covalently. In embodiments, two identical polypeptides are linked covalently (e.g., via disulfide bonds) forming a "homodimer". FIG. 1 diagrammatically represents an insulin-Fc fusion protein homodimer. The insulin polypeptide comprises a B-chain, a C-chain and an A-chain, and each insulin polypeptide is joined via a peptide linker to an Fc fragment. Two identical insulin-Fc fusion protein monomers are joined together vis disulfide bonds to form an insulin-Fc fusion protein homodimer. The total number of disulfide bonds in actuality may be greater or less than the number shown in FIG. 1. The Fc fragment comprises a conserver asparagine (N)-glycosylation site, at which glycols may bond during recombinant manufacturing of the insulin-Fc fusion protein in mammalian cells. In embodiments, the homodimer is encoded by a single nucleic acid molecule, wherein the homodimer is made recombinantly inside a cell by first forming insulin-Fc fusion protein monomers and by then assembling two identical insulin-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of the insulin-Fc fusion protein homodimers.

Insulin Polypeptide

An insulin polypeptide may be, for example, an insulin or insulin analog produced by β-cells in the islets of Langerhans within the pancreas. Insulin functions by regulating the absorption of glucose from the blood. Upon a stimulus, such as increased protein and glucose levels, insulin is released from β-cells and binds to the insulin receptor (IR), initiating a signal cascade that affects many aspects of mammalian (e.g., human) metabolism. Disruption of this process is directly related to several diseases, notably diabetes, insulinoma, insulin resistance, metabolic syndromes, and polycystic ovary syndrome. Insulin analogs of the present disclosure may be related to the structure of insulin yet contain one or more modifications. In some embodiments, the insulin analog comprises at least one amino acid substitution, deletion, addition or chemical modification relative to insulin, which may impact a particular feature or characteristic of the insulin-Fc fusion protein configuration. For example, the modifications or alterations described herein may impact the structure, stability, pH sensitivity, bioactivity, or binding affinity of the insulin-Fc fusion protein configuration to a cell surface receptor (e.g. an insulin hormone receptor) relative to a reference standard.

The amino acid sequence of insulin is strongly conserved throughout evolution, particularly in vertebrates. For example, native canine and porcine insulins differ by only one amino acid from human insulin, native bovine insulin differs by only three amino acids from human insulin, and native feline insulin differs by just four amino acids from human insulin. As used herein, the terms "B-chain or B-chain analog", "C-peptide" or "C-chain", and "A-chain or A-chain analog" refer to the peptide segments of an insulin polypeptide as illustrated in FIG. 1. Native insulin is a 51 amino acid hormone containing two peptide chains (i.e., a B-chain and an A-chain) connected via disulfide bonds (e.g., disulfide bonds formed by one or more B-chain cysteine side chain thiols and one or more A-chain cysteine side chain thiols). The A-chain of native insulin is 21 amino acids in length and the B-chain of native insulin is 30 amino acids in length. In the native form of insulin, the A-chain contains one intrachain disulfide bond formed by two A-chain cysteine side chain thiols. For reference purposes, the sequences for the human insulin B-chain of SEQ ID NO: 1 and the human insulin A-chain of SEQ ID NO: 2 are shown below:

(SEQ ID NO: 1)
FVNQHLCGSHLVEALYLVCGERGFFYTPKT (SEQ ID NO: 2)
GIVEQCCTSICSLYQLENYCN.

As used herein, the term "insulin" or "insulin polypeptide" encompasses mature insulin, preproinsulin, proinsulin, and naturally occurring insulin, or analogs thereof. In embodiments, an insulin polypeptide can be a full-length insulin polypeptide or a fragment thereof. In embodiments, an insulin polypeptide can comprise one or more fragments from mature insulin, preproinsulin, proinsulin, or naturally occurring insulin.

Insulin is normally constructed as a N-terminus-B-chain:C-chain:A-chain-C-terminus polypeptide, wherein the C-chain is cleaved in order to make it bioactive. For reference purposes, the sequence of the entire human insulin molecule including the C-chain (i.e., human proinsulin) is shown below with the C-chain underlined:

(SEQ ID NO: 3)
FVNQHLCGSHLVEALYLVCGERGFFYTPKT<u>RREAEDLQVGQVELGGGPG</u>
<u>AGSLQPLALEGSLQKR</u>GIVEQCCTSICSLYQLENYCN.

The transformation of the single-chain insulin polypeptide into a bioactive two-chain polypeptide is normally accomplished within the β-cells of the islets of Langerhans prior to glucose-stimulated insulin secretion by two endoproteases, Type I endoproteases, PC1 and PC3, that disrupt the C peptide-B chain connection and PC2, and a Type II endoprotease, that cleaves the C peptide-A chain bond at exactly the right sites. However, cell systems used for the biosynthesis of therapeutic molecules such as insulin (e.g. bacteria, yeast, and mammalian (e.g. HEK and CHO) cell systems) do not possess this pathway, and therefore the transformation must take place after expression and harvesting of the single chain polypeptide using chemical or enzymatic methods. All the known techniques for cleaving the C-chain after expression and harvesting rely on first modifying the C-chain such that it terminates in a lysine just before the N-terminus of the A-chain. Then, using an enzyme selected from the trypsin or Lys-C families, which clips peptide bonds specifically at the C-termini of lysine residues, the single chain-insulin polypeptide is cleaved at the C-terminal lysine of the C-chain and at the C-terminal lysine at the $29^{th}$ position from the N-terminus of the B-chain. In some cases, the resulting bioactive two-chain insulin is used without reattaching the clipped amino acid at the $30^{th}$ position from the N-terminus of the B-chain, and in some cases the clipped amino acid at the $30^{th}$ position from the N-terminus of the B-chain is added back to the molecule using an additional enzymatic method. Such a process works well with insulin because it contains only one lysine in its entire two chain polypeptide form. However, this process cannot be used on the insulin-Fc fusion proteins contained herein, because all known Fc fragments contain multiple lysine residues. The enzymatic cleavage process would, therefore, digest the Fc fragment into non-functional parts, thereby eliminating the ability of the Fc fragment to prolong the action of the insulin polypeptide in vivo. Therefore, an insulin-Fc fusion protein of the present invention must comprise an insulin polypeptide that does not require C-chain cleavage and is therefore bioactive in its single chain form.

A number of bioactive single chain insulin polypeptides have been described in the art. In all cases, the single chain insulin polypeptides contain C-chains of specific length and composition as well as A-chains and B-chains mutated at specific amino acid sites in order to achieve electrostatic balance, prevent aggregation, and enhance insulin receptor (IR) binding and/or downstream signaling to achieve bioactivity at levels comparable to that of the native two-chain insulin. Herein, the location of mutations on peptide segments are notated using the name of the segment (e.g., B-chain, C-chain, A-chain) and the number of the amino acid counting from the N-terminus of the segment. For example, the notation "B10" refers to the $10^{th}$ amino acid from the N-terminus of the amino acid sequence of the B-chain. The notation "A8" refers to the 8th amino acid from the N-terminus of the A-chain. Furthermore, if an amino acid is mutated from its native form to a new amino acid at a particular location, the location is appended with the one letter amino acid code for the new amino acid. For example, B10D refers to an aspartic acid mutation at the $10^{th}$ amino acid from the N-terminus of the amino acid sequence of the B-chain and A8H refers to a histidine mutation at the $8^{th}$ amino acid from the N-terminus of the amino acid sequence of the A-chain.

In examples, a single chain insulin analog comprises a C-chain 4-9 amino acids in length comprising a specific set of alanine substitutions and/or deletions derived from a C-chain of the sequence GGGPRR (SEQ ID NO: 8).

In some examples, the C-chain comprises the following sequence:

$X_1X_2X_3X_4X_5X_6X_7$RR (SEQ ID NO: 9)

wherein X1 is E or absent, X2 is E or absent, X3 is E, G or absent, $X_4$ is G, E, A, or absent, $X_5$ is G, E, A, F, or D, $X_6$ is G, E, or A, and $X_7$ is P or A.

In some examples, the C-chain comprises the following sequence:

E$X_1X_2X_3X_4$A (SEQ ID NO: 10)

wherein $X_1$ is E or A, $X_2$ is G or A, $X_3$ is A or P, and $X_4$ is A or R.

In some examples, the C-chain comprises the following sequence:

$X_1X_2$GPR (SEQ ID NO: 11)

wherein $X_1$ is E or absent, and $X_2$ is E or A.

In some examples, the C-chain comprises the following sequence:

$X_1$EG$X_2X_3X_4$(SEQ ID NO: 12)

wherein $X_1$ is E or absent, $X_2$ A or P, $X_3$ is A or R, and $X_4$ is A or R.

SEQ ID NO: 15 was developed by The Department of Biochemistry, Case Western Reserve University School of Medicine and the Department of Medicine, University of Chicago (see Hua, Q.-x, Nakagawa, S. H., Jia, W., Huang, K., Phillips, N. B., Hu, S.-q., Weiss, M. A., (2008) *J. Biol. Chem* Vol. 283, No. 21 pp 14703-14716). In this example, at position 8 of the A-chain (i.e., A8), histidine is substituted for threonine; at position 10 of the B-chain (i.e., B10), aspartic acid is substituted for histidine; at position 28 of the B-chain (i.e., B28), aspartic acid is substituted for proline; and at position 29 of the B-chain (i.e., B29), proline is substituted for lysine. The C-chain comprises SEQ ID NO: 8. SEQ ID NO: 15 is listed below with each of the non-native amino acids underlined:

```
                                              (SEQ ID NO: 15)
FVNQHLCGSDLVEALYLVCGERGFFYTDPTGGGPRRGIVEQCCHSICSL

YQLENYCN.
```

In embodiments, alanine may be substituted for tyrosine at position 16 from the N-terminus of the B-chain (i.e., B16) in SEQ ID NO: 15 to produce SEQ ID NO: 16, as an alanine substitution in this position is known to be less capable of activating insulin-specific T cells (Alleva, D. G., Gaur, A., Jin, L., Wegmann, D., Gottlieb, P. A., Pahuja, A., Johnson, E. B., Motheral, T., Putnam, A., Crowe, P. D., Ling, N., Boehme, S. A., Conlon, P. J., (2002) *Diabetes* Vol. 51, No. 7 pp 2126-2134). SEQ ID NO: 16 is listed below with each of the non-native amino acids underlined:

```
                                              (SEQ ID NO: 16)
FVNQHLCGSDLVEALALVCGERGFFYTDPTGGGPRRGIVEQCCHSICSL

YQLENYCN.
```

In some embodiments, it was unexpectedly discovered that specific amino acids in SEQ ID NO: 15 and SEQ ID NO: 16 led to the development of neutralizing anti-drug antibodies after repeated subcutaneous injections in the target animal (e.g., dog or cat) as is illustrated in Example 26. The anti-drug antibodies led to an unacceptable reduction in the NAOC after multiple injections (e.g., a NAOCR value after the third injection of less than 0.5), rendering the associated insulin-Fc fusion proteins non-viable. Specifically, it was discovered in the steps leading up to the invention of this disclosure that the A8 mutation to histidine and the B10 mutation to aspartic acid accounted for the vast majority of the anti-drug antibody specificity and thus represented immunogenic "hot spots" (e g immunogenic epitopes) on the insulin-polypeptide.

In addition to the B-Chain of SEQ ID NO: 15 (FVNQHLCGSDLVEALYLVCGERGFFYTDPT—SEQ ID NO: 5) and the B-chain of SEQ ID NO: 16 (FVNQHLCGSDLVEALALVCGERGFFYTDPT—SEQ ID NO: 4), other examples of B-chains that may be substituted for SEQ ID NO: 4 and SEQ ID NO: 5 in the insulin polypeptides of SEQ ID NO: 15 and SEQ ID NO: 16 include FVNQHLCGSHLVEALYLVCGERGFFYT$X_1X_2$PT, wherein $X_1X_2$ is PR, PE, PA, DP, EP, AP, DK, EK, ER, AK, or AR (SEQ ID NO: 6) and FVNQHLCGSHLVEALYLVCGERGFFYTKPT (SEQ ID NO: 7).

In some embodiments, in addition to the A-Chain of SEQ ID NO: 15 and SEQ ID NO: 16(GIVEQCCHSICSLYQLENYCN-SEQ ID NO: 14), other examples of A-chains that may be substituted for SEQ ID NO: 14 in the insulin polypeptides of SEQ ID NO: 15 and SEQ ID NO: 16 include GIVEQCCX1SICSLX2QLENYCN wherein X1 is T, H, S, E or A and wherein X2 is any amino acid other than P (SEQ ID NO: 13).

Table 1 illustrates the A-Chain analogs, C-Chain Analogs, and B-Chain analogs which may be selected from, in any combination in forming an insulin polypeptide of the present invention.

TABLE 1

A-Chain, C-Chain and B-Chains that may be selected in any combination to form an insulin polypeptide

| SEQ ID NO: | B-Chain | SEQ ID NO: | C-Chain | SEQ ID NO: | A-Chain |
|---|---|---|---|---|---|
| SEQ ID NO: 4 | FVNQHLCGSDLVEALA LVCGERGFFYTDPT | SEQ ID NO: 9 | X1X2X3X4X5X6X7RR wherein X1 is E or absent, X2 is E or absent, X3 is E G or absent, X4 is G, E A, or absent, X5 is G, E, A, F, or D, X6 is G, E, or A, and X7 is P or A. | SEQ ID NO: 13 | GIVEQCC$X_1$SICSL$X_2$QT NYCN wherein $X_1$ is T, H, S, E or A and wherein $X_2$ is any amino acid other than P |
| SEQ ID NO: 5 | FVNQHLCGSDLVEALY LVCGERGFFYTDPT | SEQ ID NO: 10 | E$X_1X_2X_3X_4$A wherein $X_1$ is E or A, $X_2$ is G or A, $X_3$ is A or P, and $X_4$ is A or R. | SEQ ID NO: 14 | GIVEQCCHSICSLYQLE NYCN |

TABLE 1-continued

A-Chain, C-Chain and B-Chains that may be selected in any combination to form an insulin polypeptide

| SEQ ID NO: | B-Chain | SEQ ID NO: | C-Chain | SEQ ID NO: | A-Chain |
|---|---|---|---|---|---|
| SEQ ID NO: 6 | FVNQHLCGSHLVEALY LVCGERGFEYTX$_1$X$_2$PT, wherein X$_1$X$^2$ is PR, PE, PA, DP, EP, AP, DK, EK, ER, AK, or AR | SEQ ID NO: 11 | X$_1$X$_2$GPR wherein X$_1$ is E or absent, and X$_2$ is E or A. | | |
| SEQ ID NO: 7 | FVNQHLCGSHLVEALY LVCGERGFFYTKPT | SEQ ID NO: 12 | X$_1$EGX$_2$X$_3$X$_4$ wherein X$_1$ is E or absent, X$_2$ A or P. X$_3$ is A or R, and X$_4$ is A or R. | | |

In some embodiments, the insulin polypeptide comprises the following sequence:

(SEQ ID NO: 17)
FVNQHLCGSHLVEALYLVCGERGFFYTDPTEEGPRRGIVEQCCHSICSL

EQLENYCN.

In some embodiments, the insulin polypeptide comprises the following sequence:

(SEQ ID NO: 18)
FVNQHLCGSHLVEALYLVCGERGFFYTDPTEEGAPRRGIVEQCCHSICS

LEQLENYCN.

In some embodiments, the insulin polypeptide comprises the following sequence:

(SEQ ID NO: 19)
FVNQHLCGSHLVEALYLVCGERGFFYTDPTEEGAAPRRGIVEQCCHSIC

SLEQLENYCN.

In some embodiments, the insulin polypeptide comprises the following sequence:

(SEQ ID NO: 20)
FVNQHLCGSHLVEALYLVCGERGFFYTDPTEEGAAAPRRGIVEQCCHSI

CSLEQLENYCN.

Linker

In some examples, the C-terminus of the insulin polypeptide is connected directly to the N-terminus of the Fc fragment (e.g. no linker or linker absent). In other examples, the successful construction of a recombinantly made insulin-Fc fusion protein requires a linker connecting the insulin polypeptide to the Fc fragment. In embodiments, an insulin-Fc fusion protein configurations described herein comprise a peptide linker between the insulin polypeptide and the Fc fragment comprising amino acids (e.g., natural or unnatural amino acids). In embodiments, the peptide linker can be encoded by a nucleic acid molecule, for example such that a single nucleic acid molecule can encode the various peptides within an insulin polypeptide as well as the peptide linker and the Fc fragment. The choice of peptide linker (for example, the length, composition, hydrophobicity, and secondary structure) could impact the manufacturability (i.e., the homodimer titer), the chemical and enzymatic stability, the bioactivity (i.e., the NAOC value), and the immunogenicity of the insulin-Fc fusion protein (Chen, X., Zaro, J., Shen, W. C., *Adv Drug Deliv Rev.* 2013 Oct. 15; 65(10): 1357-1369). In embodiments, the peptide linker comprises the sequence GGGGAGGGG (SEQ ID NO: 25). In embodiments, the peptide linker comprises the sequence GGGGSGGGG (SEQ ID NO: 26). In embodiments, the peptide linker comprises the sequence GGGGGQGGGGQGGGGQGGGGG (SEQ ID NO: 27).

Fc Fragment

In embodiments, the Fc fragment comprises the Fc region (e.g., hinge region, CH2 domain, and CH3 domain) of a mammalian IgG, for example a canine IgGA Fc fragment (SEQ ID NO: 28), a canine IgGB Fc fragment (SEQ ID NO: 29), a canine IgGC Fc fragment (SEQ ID NO: 30), or a canine IgGD Fc fragment (SEQ ID NO: 31). In embodiments, the C-terminal lysine that is often found in native canine or IgG isotype Fc fragment amino acid sequences (i.e., the lysine that represents the last amino acid of the Fc fragment sequence) is omitted to prevent the accidental production of unwanted amino acid sequence variants during manufacturing (e.g., Fc fragments containing the C-terminal lysine becoming mixed with Fc fragments where the C-terminal lysine is omitted, which can occur during production of the desired protein within cells (Dick, L W., (2008) *Biotechnol Bioeng.* August 15; 100(6) pp 1132-43). Therefore, in embodiments, the canine Fc fragment sequences lacking a C-terminal lysine are:

Canine IgGA (SEQ ID NO: 28)
RCTDTPPCPVPEPLGGPSVLIFPPKPKDILRITRTPEVTCVVLDLGRED

PEVQISWFVDGKEVHTAKTQSREQQFNGTYRVVSVLPIEHQDWLTGKEF

KCRVNHIDLPSPIERTISKARGRAHKPSVYVLPPSPKELSSSDTVSITC

LIKDFYPPDIDVEWQSNGQQEPERKHRMTPPQLDEDGSYFLYSKLSVDK

SRWQQGDPFTCAVMHETLQNHYTDLSLSHSPG

Canine IgGB (SEQ ID NO: 29)
DCPKCPAPEMLGGPSVFIFPPKPKDTLLIARTPEVTCVVVDLDPEDPEV

QISWFVDGKQMQTAKTQPREEQFNGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG

Canine IgGC (SEQ ID NO: 30)
CNNCPCPGCGLLGGPSVFIFPPKPKDILVTARTPTVTCVVVDLDPENPE

VQISWFVDSKQVQTANTQPREEQSNGTYRVVSVLPIGHQDWLSGKQFKC

KVNNKALPSPIEEIISKTPGQAHQPNVYVLPPSRDEMSKNTVTLTCLVK

DFFPPEIDVEWQSNGQQEPESKYRMTPPQLDEDGSYFLYSKLSVDKSRW

QRGDTFICAVMHEALHNHYTQISLSHSPG

Canine IgGD (SEQ ID NO: 31)
CISPCPVPESLGGPSVFIFPPKPKDILRITRTPEITCVVLDLGREDPEVQ

ISWFVDGKEVHTAKTQPREQQFNSTYRVVSVLPIEHQDWLTGKEFKCRVN

HIGLPSPIERTISKARGQAHQPSVYVLPPSPKELSSSDTVTLTCLIKDFF

PPEIDVEWQSNGQPEPESKYHTTAPQLDEDGSYFLYSKLSVDKSRWQQGD

TFTCAVMHEALQNHYTDLSLSHSPG

For canines, replacing the human Fc with canine IgGA is preferable to minimize any unwanted immunogenicity in dogs due to the IgGA isotype's lack of Fc(gamma) effector function in dogs (much like the human IgG2 isotype in humans). However, the insulin-Fc fusion protein configuration of SEQ ID NO: 33 comprising the insulin polypeptide of SEQ ID NO: 16, the peptide linker of SEQ ID NO: 25, and the canine IgGA fragment of SEQ ID NO: 28 was highly aggregated with low titers of the desired homodimer as illustrated in Example 20. The protein titer was 22 mg/L and the % homodimer was 24%, yielding a homodimer titer of 5.28 mg/L, which is significantly less than the required homodimer titer of 40 mg/L.

(SEQ ID NO: 33)
FVNQHLCGSDLVEALALVCGERGFFYTDPTGGGPRRGIVEQCCHSICSL

YQLENYCNGGGGAGGGGRCTDTPPCPVPEPLGGPSVLIFPPKPKDILRI

TRTPEVTCVVLDLGREDPEVQISWFVDGKEVHTAKTQSREQQFNGTYRV

VSVLPIEHQDWLTGKEFKCRVNHIDLPSPIERTISKARGRAHKPSVYVL

PPSPKELSSSDTVSITCLIKDFYPPDIDVEWQSNGQQEPERKHRMTPPQ

LDEDGSYFLYSKLSVDKSRWQQGDPFTCAVMHETLQNHYTDLSLSHSPG

A further insulin-Fc fusion protein configuration (SEQ ID NO: 35) comprising the canine IgGA Fc fragment of SEQ ID NO: 28, the insulin polypeptide of SEQ ID NO: 4, and the linker of SEQ ID NO: 26 similarly was highly aggregated with low titers of the desired homodimer as illustrated in Example 20. The protein titer was 21 mg/L and the % homodimer was 19%, yielding a homodimer titer of 3.99 mg/L, which is significantly less than the required homodimer titer of 40 mg/L.

(SEQ ID NO: 35)
FVNQHLCGSDLVEALYLVCGERGFFYTDPTGGGPRRGIVEQCCHSICSL

YQLENYCNGGGSGGGGRCTDTPPCPVPEPLGGPSVLIFPPKPKDILRI

TRTPEVTCVVLDLGREDPEVQISWFVDGKEVHTAKTQSREQQFNGTYRV

VSVLPIEHQDWLTGKEFKCRVNHIDLPSPIERTISKARGRAHKPSVYVL

PPSPKELSSSDTVSITCLIKDFYPPDIDVEWQSNGQQEPERKHRMTPPQ

LDEDGSYFLYSKLSVDKSRWQQGDPFTCAVMHETLQNHYTDLSLSHSPG

A further insulin-Fc fusion protein configuration (SEQ ID NO: 37) comprising the canine IgGA Fc fragment of SEQ ID NO: 28, the insulin polypeptide of SEQ ID NO: 23, and the linker of SEQ ID NO: 26 similarly was highly aggregated with low titers of the desired homodimer as illustrated in Example 20. The protein titer was 11 mg/L which is significantly less than the required homodimer titer of 40 mg/L.

(SEQ ID NO: 37)
FVNQHLCGSHLVEALYLVCGERGFFYTPKAGGGPRRGIVEQCCTSICSL

YQLENYCNGGGGSGGGGRCTDTPPCPVPEPLGGPSVLIFPPKPKDILRI

TRTPEVTCVVLDLGREDPEVQISWFVDGKEVHTAKTQSREQQFNGTYRV

VSVLPIEHQDWLTGKEFKCRVNHIDLPSPIERTISKARGRAHKPSVYVL

PPSPKELSSSDTVSITCLIKDFYPPDIDVEWQSNGQQEPERKHRMTPPQ

LDEDGSYFLYSKLSVDKSRWQQGDPFTCAVMHETLQNHYTDLSLSHSPG

A further insulin-Fc fusion protein configuration (SEQ ID NO: 39) comprising the canine IgGA Fc fragment of SEQ ID NO: 28, the insulin polypeptide of SEQ ID NO: 22, and the linker of SEQ ID NO: 26 similarly was highly aggregated with low titers of the desired homodimer as illustrated in Example 20. The protein titer was 18 mg/L which is significantly less than the required homodimer titer of 40 mg/L.

(SEQ ID NO: 39)
FVNQHLCGSHLVEALYLVCGERGFFYTPKAAAAAAAKGIVEQCCTSICS

LYQLENYCNGGGGSGGGGRCTDTPPCPVPEPLGGPSVLIFPPKPKDILR

ITRTPEVTCVVLDLGREDPEVQISWFVDGKEVHTAKTQSREQQFNGTYR

VVSVLPIEHQDWLTGKEFKCRVNHIDLPSPIERTISKARGRAHKPSVYV

LPPSPKELSSSDTVSITCLIKDFYPPDIDVEWQSNGQQEPERKHRMTPP

QLDEDGSYFLYSKLSVDKSRWQQGDPFTCAVMHETLQNHYTDLSLSHSP

G

The sequence alignment of the full amino acid sequences of the insulin-Fc fusion proteins SEQ ID NO: 33, SEQ ID NO: 35, SEQ ID NO: 37, and SEQ ID NO: 39 is shown in FIG. 3 (Clustal Omega). Despite mutating the insulin polypeptide and/or the linker, there was no embodiment based on the canine IgGA Fc fragment (SEQ ID NO: 28) with a low enough degree of aggregation and a high enough titer of the desired homodimer.

On the other hand, replacing the canine IgGA Fc fragment (SEQ ID NO: 28) with the canine IgGB Fc fragment (SEQ ID NO: 29) yielded a much less aggregated compound with a comparatively high titer of the desired homodimer. The insulin-Fc fusion protein configuration of SEQ ID NO: 41, comprising the insulin polypeptide of SEQ ID NO: 16, the linker of SEQ ID NO: 25 and the canine IgGB Fc fragment of SEQ ID NO: 29 had a protein yield of 80 mg/L and a % homodimer of 93% resulting in a homodimer titer of 74.7 mg/L, which surpassed the required homodimer titer of 40 mg/L, as illustrated in Example 20.

(SEQ ID NO: 41)
FVNQHLCGSDLVEALALVCGERGFFYTDPTGGGPRRGIVEQCCHSICSL

YQLENYCNGGGGAGGGGDCPKCPAPEMLGGPSVFIFPPKPKDTLLIART

PEVTCVVVDLDPEDPEVQISWFVDGKQMQTAKTQPREEQFNGTYRVVSV

LPIGHQDWLKGKQFTCKVNNKALPSPIERTISKARGQAHQPSVYVLPPS

REELSKNTVSLTCLIKDFFPPDIDVEWQSNGQQEPESKYRTTPPQLDED

GSYFLYSKLSVDKSRWQRGDTFICAVMHEALHNHYTQESLSHSPG

The preference for the canine IgGB Fc fragment over other canine Fc fragments was confirmed in embodiments containing the insulin polypeptide of SEQ ID NO: 16 and the peptide linker of SEQ ID NO: 25, with canine IgGC and IgGD as illustrated in Example 20. The insulin-Fc fusion protein configuration of SEQ ID NO: 43, comprising the insulin polypeptide of SEQ ID NO: 16, the peptide linker of SEQ ID NO: 25 and the canine IgGC Fc fragment of SEQ ID NO: 30 yielded no material at all. The insulin-Fc fusion protein configuration of SEQ ID NO: 45, comprising the insulin polypeptide of SEQ ID NO: 16, the peptide linker of SEQ ID NO: 25 and the canine IgGD Fc fragment of SEQ ID NO: 31 yielded a good protein yield of 134 mg/L, however the material was highly aggregated with a % homodimer of 12.3% and a homodimer titer of 16.5 mg/L, which is significantly less than the required homodimer titer of 40 mg/L. The results are shown in Table 2.

(SEQ ID NO: 43)
FVNQHLCGSDLVEALALVCGERGFFYTDPTGGGPRRGIVEQCCHSICSL

YQLENYCNGGGGAGGGGCNNCPCPGCGLLGGPSVFIFPPKPKDILVTAR

TPTVTCVVVDLDPENPEVQISWFVDSKQVQTANTQPREEQSNGTYRVVS

VLPIGHQDWLSGKQFKCKVNNKALPSPIEEIISKTPGQAHQPNVYVLPP

SRDEMSKNTVTLTCLVKDFFPPEIDVEWQSNGQQEPESKYRMTPPQLDE

DGSYFLYSKLSVDKSRWQRGDTFICAVMHEALHNHYTQISLSHSPG (SEQ ID NO: 45)
FVNQHLCGSDLVEALALVCGERGFFYTDPTGGGPRRGIVEQCCHSICSL

YQLENYCNGGGGAGGGGCISPCPVPESLGGPSVFIFPPKPKDILRITRT

PEITCVVLDLGREDPEVQISWFVDGKEVHTAKTQPREQQFNSTYRVVSV

LPIEHQDWLTGKEFKCRVNHIGLPSPIERTISKARGQAHQPSVYVLPPS

PKELSSSDTVTLTCLIKDFFPPEIDVEWQSNGQQEPESKYHTTAPQLDE

DGSYFLYSKLSVDKSRWQQGDTFTCAVMHEALQNHYTDLSLSHSPG

TABLE 2

Homodimer titers for insulin-Fc fusion protein configurations utilizing canine IgG Fc Fragments

| SEQ ID NO: | Canine IgG | Protein Yield (mg/L) | % Homodimer | Homodimer Titer (mg/L) |
| --- | --- | --- | --- | --- |
| SEQ ID NO: 33 | IgGA | 22 | 24% | 5.28 |
| SEQ ID NO: 35 | IgGA | 21 | 19% | 3.99 |
| SEQ ID NO: 37 | IgGA | 11 | Not tested | ≤11 |
| SEQ ID NO: 39 | IgGA | 18 | Not tested | ≤18 |

TABLE 2-continued

Homodimer titers for insulin-Fc fusion protein configurations utilizing canine IgG Fc Fragments

| SEQ ID NO: | Canine IgG | Protein Yield (mg/L) | % Homodimer | Homodimer Titer (mg/L) |
| --- | --- | --- | --- | --- |
| SEQ ID NO: 41 | IgGB | 80 | 93% | 74.4 |
| SEQ ID NO: 43 | IgGC | 0 | Not tested | 0 |
| SEQ ID NO: 45 | IgGD | 134 | 12% | 16.5 |

In vitro insulin receptor binding for the insulin-Fc fusion proteins of SEQ ID NO: 41 and SEQ ID NO: 45 was tested according to the procedure of Example 11. The insulin-Fc fusion protein of SEQ ID NO: 45 demonstrated an IC50 of greater than 5000 nM, as shown in Table 3, indicating that the compound was highly unlikely to show bioactivity in vivo. However, the insulin-Fc fusion protein of SEQ ID NO: 41 demonstrated an IC50 of 28 nM indicating that this sequence was likely to be bioactive in vivo.

TABLE 3

Homodimer titers for sequences utilizing native canine IgGB, IgGC, and IgGD Fc fragments

| SEQ ID NO: | IgG Fragment | Protein Yield (mg/L) | % Homo-dimer | Homodimer Titer (mg/L) | IR Binding, IC50 (nM) |
| --- | --- | --- | --- | --- | --- |
| SEQ ID NO: 33 | IgGA | 22 | 24% | 5.28 | 2,733 |
| SEQ ID NO: 41 | IgGB | 80 | 93% | 74.4 | 28 |
| SEQ ID NO: 43 | IgGC | 0 | Not tested | 0 | DNM* |
| SEQ ID NO: 45 | IgGD | 134 | 12% | 16.5 | >5000 |

*DNM = Did Not Measure

Given the promising homodimer titer and insulin receptor activity results shown in Table 3, the insulin-Fc fusion protein configuration of SEQ ID NO: 41, comprising the insulin polypeptide of SEQ ID NO: 16, the linker of SEQ ID NO: 25 and the canine IgGB Fc fragment (SEQ ID NO: 29) was bioactive in dogs, exhibiting glucose lowering bioactivity over multiple days (i.e., the NAOC value was greater than 150% FBGL·days·kg/mg).

The preference for insulin-Fc fusion protein configurations comprising the canine IgGB fragment was further evaluated using the insulin polypeptide of SEQ ID NO: 21 and the linker of SEQ ID NO: 27, both of which vary considerably from the insulin polypeptide of SEQ ID NO: 16 and the peptide linker of SEQ ID NO: 25.

(SEQ ID NO: 21)
FVNQHLCGSHLVEALELVCGERGFHYGGGGGSGGGGIVEQCCTSTCS

LDQLENYC

GGGGGQGGGGQGGGGQGGGGG (SEQ ID NO: 27)

Insulin-Fc fusion proteins containing the insulin polypeptide of SEQ ID NO: 21 and the peptide linker of SEQ ID NO: 27 were synthesized using Fc fragments from the canine IgGA (SEQ ID NO: 28), canine IgGB (SEQ ID NO: 29), canine IgGC (SEQ ID NO: 30), or canine IgGD (SEQ ID NO: 31) immunoglobulins.

Using the conventional purification method, only the insulin-Fc fusion configurations comprising canine IgGA (SEQ ID NO: 28) and canine IgGB (SEQ ID NO: 29) showed any appreciable protein yields. However, just like before, the insulin-Fc fusion configuration comprising canine IgGA (SEQ ID NO: 28) was highly aggregated and exhibited low levels of bioactivity, whereas the insulin-Fc fusion configuration comprising canine IgGB (SEQ ID NO: 29) exhibited a low degree of aggregation (i.e. high % homodimer), a high titer of the desired homodimer (i.e., a homodimer titer greater than 40 mg/L), and appreciable levels of long-duration glucose lowering bioactivity in dogs (i.e., the NAOC value was greater than 150% FBGL·days·kg/mg). Using an alternative purification method, the insulin-Fc fusion configuration comprising canine IgGC (SEQ ID NO: 30) was recovered with low degrees of aggregation, however this insulin-Fc fusion protein configuration was minimally bioactive in dogs (i.e., the NAOC value was less than 150% FBGL·days·kg/mg), presumably due to its low affinity for the FcRn receptor. Therefore, with respect to a dog-specific product, the canine IgGB (SEQ ID NO: 28) is the preferred Fc fragment for insulin-Fc fusion protein configurations used in dogs, regardless of the choice of insulin polypeptide or linker.

Insulin-Fc Fusion Proteins

Provided herein are insulin-Fc fusion proteins comprising an insulin polypeptide, an Fc fragment, and a linker between the insulin polypeptide and the Fc fragment. In embodiments, the insulin polypeptide comprises domains in the following orientation from N- to C-termini: (N-terminus)-B-chain-C-chain-A-chain-(C-terminus). In embodiments, the insulin polypeptide is located on the N-terminal side of the Fc fragment. In embodiments, the fusion protein comprises domains in the following orientation from N- to C-termini: (N-terminus)-insulin polypeptide-linker-Fc fragment-(C-terminus) (e.g., (N-terminus)-B-chain-C-chain-A-chain-linker-Fc fragment-(C-terminus)) as illustrated in FIG. 1.

The repeated dose subcutaneous bioactivity of the insulin-Fc fusion protein of SEQ ID NO: 41 was tested in dogs as per the method described in Example 15. N=3 animals were dosed subcutaneously at day 0, at day 35, and at day 42, and the % FBGL was measured for the 7-day window after each dose according to Example 15. The NAOC and NAOCR were calculated according to the procedure of Example 15 for each repeated subcutaneous injection. As illustrated in Table 4, repeated subcutaneous dosing in dogs unexpectedly revealed a significant decay in bioactivity by the third dose as measured by a significant decrease in the NAOCR (i.e., the NAOC for the third injection was only 0.40, or 40%, of the NAOC for the first injection).

TABLE 4

NAOC per dose and NAOCR for repeated doses of SEQ ID NO: 41

| Injection Number of SEQ ID NO: 41 | NAOC (% FBGL · days · kg/mg) | NAOCR (ratioed to Week 1) |
|---|---|---|
| 1 | 330 | 1.0 |
| 2 | 339 | 1.1 |
| 3 | 115 | 0.4 |

Given that the canine IgGB isotype interacts with the canine Fc(gamma) receptor with higher affinities than its canine IgGA counterpart, there may or may not be a risk of unwanted immunogenicity after repeated injections. One method for reducing the Fc(gamma) interaction involves deglycosylating or preventing the glycosylation of the Fc fragment during synthesis in the host cell. Each IgG fragment contains a conserved asparagine (N)-glycosylation site in the CH2 domain of each heavy chain of the Fc region.

Herein, the notation used to refer to the conserved N-glycosylation site is "cNg". One way to remove the attached glycan from a synthesized insulin-Fc fusion protein is to mutate the cNg site to prevent the attachment of glycans altogether during production in the host cell. Herein, the notation used to describe a cNg mutation is cNg-(substituted amino acid). For example, if the asparagine at the cNg site is mutated to serine, this mutation is notated as "cNg-S".

The absolute position of the cNg site from the N-terminus of the B-chain of the insulin-Fc fusion protein varies depending on the length of the insulin polypeptide, the length of the linker, and any omitted amino acids in the Fc fragment prior to the cNg site. Herein, the notation used to refer to the absolute position of the cNg site in a given insulin-Fc fusion protein sequence (as measured counting from the N-terminus of the B-chain of the insulin-Fc fusion protein) is "NB(number)". For example, if the cNg site is found at the 138th amino acid position as counted from the N-terminus of the B-chain, the absolute position of this site is referred to as cNg-NB138. As a further example, if the cNg site is found at the 138th amino acid position as counted from the N-terminus of the B-chain, and the asparagine at this site is mutated to serine, this mutation is noted as "cNg-NB138-S".

Deglycosylation of the Fc fragments of various insulin-Fc fusion protein configurations comprising the canine IgGB Fc fragment of SEQ ID NO: 29 were performed according to Example 25.

In an example, the insulin-Fc fusion protein of SEQ ID NO: 47 comprises the insulin polypeptide of SEQ ID NO: 16, the linker of SEQ ID NO: 25 and the canine IgGB Fc fragment (SEQ ID NO: 29) with cNg-S (underlined).

(SEQ ID NO: 47)
FVNQHLCGSDLVEALALVCGERGFFYTDPTGGGPRRGIVEQCCHSICSL

YQLENYCNGGGGAGGGGDCPKCPAPEMLGGPSVFIFPPKPKDTLLIART

PEVTCVVVDLDPEDPEVQISWFVDGKQMQTAKTQPREEQFSGTYRVVSV

LPIGHQDWLKGKQFTCKVNNKALPSPIERTISKARGQAHQPSVYVLPPS

REELSKNTVSLTCLIKDFFPPDIDVEWQSNGQQEPESKYRTTPPQLDED

GSYFLYSKLSVDKSRWQRGDTFICAVMHEALHNHYTQESLSHSPG

As illustrated in Table 5, the insulin-Fc fusion protein configuration of SEQ ID NO: 47 yielded acceptable homodimer titer and IR binding. In spite of mutating the cNg-NB138 site to S to reduce immunogenicity due to glycosylation, the bioactivity of the insulin-Fc fusion protein demonstrated a significant decay in bioactivity by the third dose as measured by a significant decrease in the NAOCR as illustrated in Example 27.

In an example, the insulin-Fc fusion protein configuration comprises the insulin polypeptide of SEQ ID NO: 24, where B10 is restored to H and A8 is restored to T in an attempt to eliminate anti-drug antibodies targeting the B10D and A8H sites on the insulin polypeptide. The insulin-Fc fusion protein configuration of SEQ ID NO: 49, comprises the insulin polypeptide of SEQ ID NO: 24, the linker of SEQ ID NO: 25 and the canine IgGB Fc fragment (SEQ ID NO: 29) with cNg-Q (B10, A8 and cNg-Q sites underlined).

(SEQ ID NO: 49)
FVNQHLCGSHLVEALALVCGERGFFYTDPTGGGPRRGIVEQCCTSICSL

YQLENYCNGGGGAGGGGDCPKCPAPEMLGGPSVFIFPPKPKDTLLIART

PEVTCVVVDLDPEDPEVQISWFVDGKQMQTAKTQPREEQFQGTYRVVSV

LPIGHQDWLKGKQFTCKVNNKALPSPIERTISKARGQAHQPSVYVLPPS

REELSKNTVSLTCLIKDFFPPDIDVEWQSNGQQEPESKYRTTPPQLDED

GSYFLYSKLSVDKSRWQRGDTFICAVMHEALHNHYTQESLSHSPG

As illustrated in Table 5, the insulin-Fc fusion protein configuration of SEQ ID NO: 49 did not yield acceptable homodimer titer or IR binding. Additionally, in spite of restoring the B10 and A8 immunogenic sites on the insulin-polypeptide and mutating cNg-NB138 site to Q to reduce immunogenicity due to glycosylation, the bioactivity of the insulin-Fc fusion protein demonstrated a significant decay in bioactivity by the third dose as measured by a significant decrease in the NAOCR as illustrated in Example 27.

In a further attempt to reduce unwanted immunogenicity, the first amino acid of the Fc fragment (in the hinge region), the aspartic acid (D), was eliminated. In a preferred embodiment, the insulin-Fc fusion protein configuration of SEQ ID NO: 51, comprises the insulin polypeptide of SEQ ID NO: 16, the linker of SEQ ID NO: 25 and the canine IgGB Fc fragment (SEQ ID NO: 29) with the aspartic acid (D) at the Fc hinge omitted (shown as "_" and the cNg site on the Fc fragment mutated to lysine (K). As shown in Table 5, the insulin-Fc fusion protein configuration of SEQ ID NO: 51 illustrated adequate homodimer titer and acceptable IR binding. Unexpectedly, even with the B10D and A8H immunogenic sites on the insulin-polypeptide, SEQ ID NO: 51 exhibited strong bioactivity in vivo, and no significant decay in bioactivity by the fourth dose, as measured by a significant decrease in the NAOCR.

(SEQ ID NO: 51)
FVNQHLCGSDLVEALALVCGERGFFYTDPTGGGPRRGIVEQCCHSICSL

YQLENYCNGGGGAGGGG_CPKCPAPEMLGGPSVFIFPPKPKDTLLIARTP

EVTCVVVDLDPEDPEVQISWFVDGKQMQTAKTQPREEQFKGTYRVVSVL

PIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDG

SYFLYSKLSVDKSRWQRGDTFICAVMHEALHNHYTQESLSHSPG

TABLE 5

Homodimer titers and IR binding for insulin-Fc fusion protein configurations utilizing canine IgGB Fc with cNg mutations

| SEQ ID NO: | cNg MUTATION | Protein Yield (mg/L) | % Homo-dimer | Homodimer Titer (mg/L) | IR Binding, IC50 (nM) |
|---|---|---|---|---|---|
| SEQ ID NO: 47 | S | 76.7 | 98.3% | 75.4 | 145 |
| SEQ ID NO: 49 | Q | 21.4 | 98.7% | 21.1 | >5000 |
| SEQ ID NO: 51 | K | 45.4 | 98.1% | 44.5 | 147 |

In the embodiment comprising the insulin-Fc fusion protein of SEQ ID NO: 51, the nucleic acid sequence (leader sequence underlined) is:

(SEQ ID NO: 52)
atggaatggagctgggtctttctcttcttcctgtcagtaacgactggtg tccactccttcgtgaaccagcacctgtgcggctccgacctggtggaagc tctggctctcgtgtgcggcgagcggggcttcttctacaccgatcccact ggaggcggtccacgcagaggcatcgtggaacagtgctgccactccatct gctccctgtaccagctggaaaactactgcaatggcggaggtggtgcagg aggcggtggatgccccaagtgccccgctcccgagatgctgggcggaccc agcgtgttcatcttccctcccaagcccaaggacacactgctgatcgcca ggacccccgaggtgacctgcgtggtggtggacctggatcccgaagaccc cgaggtgcagatcagctggttcgtggatggaaagcagatgcagaccgcc aagacccaaccccgggaagagcagttcaaaggcacctacagggtggtga gtgtgttgcccatcggccaccaggactggctgaaggggaagcaattcac atgcaaggttaataacaaggccctgcccagccccatcgagaggaccatc agcaaggccaggggccaggcccaccagccatctgtgtacgtgctgcccc catctagggaggaactgagcaagaacacagtcagccttacttgcctgat caaggacttcttcccaccggacatagacgtggagtggcagagtaacggc cagcaggagcccgagagcaagtataggaccacaccgccccaactggacg aggacggaagctacttcctctacagcaaattgagcgttgacaaaagcag gtggcagcgaggcgacaccttcatctgcgccgtgatgcacgaggctttg cataaccactacacccaggagagcctgtcccacagccccggatag.

FIG. 12 illustrates an alignment between the amino acid sequence of the insulin-Fc fusion protein of SEQ ID NO: 51 and its corresponding nucleic acid sequence of SEQ ID NO: 52.

In some embodiments, an insulin-Fc fusion protein described herein does not include a leader amino acid sequence at the N-terminus. In other embodiments, an insulin-Fc fusion protein described herein includes a leader sequence, e.g., at the N-terminus. An exemplary leader sequence includes the amino acid sequence MEWSWVFLFFLSVTTGVHS (SEQ ID NO: 54). In some embodiments, an insulin-Fc fusion protein described herein is encoded by a nucleic acid molecule comprising a leader sequence, e.g., for expression (e.g., recombinant expression) in cells (e.g., eukaryotic, e.g., mammalian cells). In certain embodiments, the leader sequence is cleaved off, e.g., in the cell culture, during expression. An exemplary nucleic acid sequence encoding a leader sequence includes the nucleic acid sequence:

(SEQ ID NO: 53)
atggaatggagctgggtctactcacacctgtcagtaacgactggtgtcc actcc.

Also disclosed herein are nucleic acid sequences (e.g., cDNA) encoding the insulin-Fc fusion proteins of SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 49.

In the embodiment comprising the insulin-Fc fusion protein of SEQ ID NO: 33, the nucleic acid sequence (leader sequence underlined) is:

(SEQ ID NO: 34)
<u>atggaatggagctgggtctttctcttcttcctgtcagtaacgactggtgt</u>
<u>ccactcct</u>tcgtgaaccagcacctgtgcggctccgacctggtggaagctc tggctctcgtgtgcggcgagcggggcttcttctacaccgatcccactgga ggcggtccacgcagaggcatcgtggaacagtgctgccactccatctgctc cctgtaccagctggaaaactactgcaatggcggaggtggtgcaggaggcg gtggacgctgcactgacacccctccatgccctgtgcccgagcccctgggt ggccccagcgtactgatcttcccaccgaaacccaaggacatcctgaggat caccCgcacccggaggtgacctgcgtggtgctggacctgggcagggagg accccgaagtgcaaatcagctggttcgtggacggaaaggaggtgcacacc gccaagacccaatcaagggagcagcagttcaacggcacctacagggtggt gagcgtgttgcccatagagcaccaggactggctgaccggcaaggagttca agtgccgcgtgaaccacattgatctccccagccccatcgagaggactatc tccaaggcccgagggagggcccacaagcccagtgtatacgtgctgccgcc ctctccgaaggaactgagctctagcgacaccgtgagcatcacctgcctga tcaaggacttctaccctcccgacatagacgtagagtggcagagcaacggc cagcaggagcccgaaaggaagcacaggatgacccCaccccaactggacga ggacggctcatactttctttatagcaagctgagtgtggacaagagcaggt ggcagcagggcgacccttttcacttgcgccgtaatgcacgagaccctgcag aatcactacaccgacctgtcactgagccatagccccggatag In the embodiment comprising the insulin-Fc fusion protein of SEQ ID NO: 35, the nucleic acid sequence (leader sequence underlined) is:

(SEQ ID NO: 36)
<u>atggaatggagctgggtctttctcttcttcctgtcagtaacgactggtgt</u>
<u>ccactcct</u>tcgtgaaccagcacctgtgcggctccgacctggtggaagctc tgtatctcgtgtgcggcgagcggggcttcttctacaccgatcccactgga ggcggtccacgcagaggcatcgtggaacagtgctgccactccatctgctc cctgtaccagctggaaaactactgcaatggcggaggtggttcaggaggcg gtggacgctgcactgacacccctccatgccctgtgcccgagcccctgggt ggccccagcgtactgatcttcccaccgaaacccaaggacatcctgaggat caccCgcacccggaggtgacctgcgtggtgctggacctgggcagggagg accccgaagtgcaaatcagctggttcgtggacggaaaggaggtgcacacc gccaagacccaatcaagggagcagcagttcaacggcacctacagggtggt gagcgtgttgcccatagagcaccaggactggctgaccggcaaggagttca agtgccgcgtgaaccacattgatctccccagccccatcgagaggactatc tccaaggcccgagggagggcccacaagcccagtgtatacgtgctgccgcc ctctccgaaggaactgagctctagcgacaccgtgagcatcacctgcctga tcaaggacttctaccctcccgacatagacgtagagtggcagagcaacggc cagcaggagcccgaaaggaagcacaggatgacccCaccccaactggacga ggacggctcatactttctttatagcaagctgagtgtggacaagagcaggt ggcagcagggcgacccttttcacttgcgccgtaatgcacgagaccctgcag aatcactacaccgacctgtcactgagccatagccccggatag In the embodiment comprising the insulin-Fc fusion protein of SEQ ID NO: 37, the nucleic acid sequence (leader sequence underlined) is:

(SEQ ID NO: 38)
<u>atggaatggagctgggtctttctcttcttcctgtcagtaacgactggtgt</u>
<u>ccactcct</u>tcgtgaaccagcacctgtgcggctcccacctggtggaagctc tgtatctcgtgtgcggcgagcggggcttcttctacaccCccaaggccgga ggtggacctcgacggggcatcgtggaacagtgctgcacctccatctgctc cctgtaccagctggaaaactactgcaatggcggaggtggttcaggaggcg gtggacgctgcactgacacccctccatgccctgtgcccgagcccctgggt ggccccagcgtactgatcttcccaccgaaacccaaggacatcctgaggat caccCgcacccggaggtgacctgcgtggtgctggacctgggcagggagg accccgaagtgcaaatcagctggttcgtggacggaaaggaggtgcacacc gccaagacccaatcaagggagcagcagttcaacggcacctacagggtggt gagcgtgttgcccatagagcaccaggactggctgaccggcaaggagttca agtgccgcgtgaaccacattgatctccccagccccatcgagaggactatc tccaaggcccgagggagggcccacaagcccagtgtatacgtgctgccgcc ctctccgaaggaactgagctctagcgacaccgtgagcatcacctgcctga tcaaggacttctaccctcccgacatagacgtagagtggcagagcaacggc cagcaggagcccgaaaggaagcacaggatgacccCaccccaactggacga ggacggctcatactttctttatagcaagctgagtgtggacaagagcaggt ggcagcagggcgacccttttcacttgcgccgtaatgcacgagaccctgcag aatcactacaccgacctgtcactgagccatagccccggatag In the embodiment comprising the insulin-Fc fusion protein of SEQ ID NO: 39, the nucleic acid sequence (leader sequence underlined) is:

(SEQ ID NO: 40)
<u>atggaatggagctgggtctttctcttcttcctgtcagtaacgactggtgt</u>
<u>ccactcct</u>tcgtgaaccagcacctgtgcggctcccacctggtggaagctc tgtatctcgtgtgcggcgagcggggcttcttctacaccCccaaggctgcc gcagcagctgccgctaaaggcatcgtggaacagtgctgcacctccatctg ctccctgtaccagctggaaaactactgcaatggcggaggtggttcaggag gcggtggacgctgcactgacacccctccatgccctgtgcccgagcccctg ggtggccccagcgtactgatcttcccaccgaaacccaaggacatcctgag gatcacccgcacccggaggtgacctgcgtggtgctggacctgggcaggg aggaccccgaagtgcaaatcagctggttcgtggacggaaaggaggtgcac accgccaagacccaatcaagggagcagcagttcaacggcacctacaggt ggtgagcgtgttgcccatagagcaccaggactggctgaccggcaaggagt tcaagtgccgcgtgaaccacattgatctccccagccccatcgagaggact -continued atctccaaggcccgagggagggcccacaagcccagtgtatacgtgctgcc gccctctccgaaggaactgagctctagcgacaccgtgagcatcacctgcc tgatcaaggacttctaccctcccgacatagacgtagagtggcagagcaac ggccagcaggagcccgaaaggaagcacaggatgaccccaccccaactgga cgaggacggctcatactttctttatagcaagctgagtgtggacaagagca ggtggcagcagggcgacccttcacttgcgccgtaatgcacgagaccctg cagaatcactacaccgacctgtcactgagccatagcccggatag In the embodiment comprising the insulin-Fc fusion protein of SEQ ID NO: 41, the nucleic acid sequence (leader sequence underlined) is:

(SEQ ID NO: 42)
<u>atggaatggagctgggtctttctcttcttcctgtcagtaacgactggtgt</u>
<u>ccactcct</u>tcgtgaaccagcacctgtgcggctccgacctggtggaagctc tggctctcgtgtgcggcgagcgggcttcttctacaccgatcccactgga ggcggtccacgcagaggcatcgtggaacagtgctgccactccatctgctc cctgtaccagctggaaaaactactgcaatggcggaggtggtgcaggaggcg gtggagactgccccaagtgccccgctcccgagatgctgggcggacccagc gtgttcatcttccctcccaagcccaaggacacactgctgatcgccaggac cccggaggtgacctgcgtggtggtggacctggatcccgaagaccccgagg tgcagatcagctggttcgtggatggaaagcagatgcagaccgccaagacc caaccccgggaagagcagttcaacggcacctacagggtggtgagtgtgtt gcccatcggccaccaggactggctgaaggggaagcaattcacatgcaagg ttaataacaaggccctgcccagccccatcgagaggaccatcagcaaggcc aggggccaggcccaccagccatctgtgtacgtgctgccccatctaggga ggaactgagcaagaacacagtcagccttacttgcctgatcaaggacttct tcccaccggacatagacgtggagtggcagagtaacggccagcaggagccc gagagcaagtataggaccacaccgccccaactggacgaggacggaagcta cttcctctacagcaaattgagcgttgacaaaagcaggtggcagcgaggcg acaccttcatctgcgccgtgatgcacgaggcttttgcataaccactacacc caggagagcctgtcccacagcccggatag In the embodiment comprising the insulin-Fc fusion protein of SEQ ID NO: 43, the nucleic acid sequence (leader sequence underlined) is:

(SEQ ID NO: 44)
<u>atggaatggagctgggtctactatatcctgtcagtaacgactggtgtcct</u>tcatcgtgaaccagcacctgtgcggctccgacctggtggaagctctggct ctcgtgtgcggcgagcgggcttcttctacaccgatcccactggaggcggtccacgcagaggcatcgtggaacagtgctgccactccatctgctccctgtac cagctggaaaaactactgcaatggcggaggtggtgcaggaggcggtggatgcaacaactgcccgtgtccgggatgcggcctcctgggcggaccgagcgt gacattaccctcctaagcccaaggacattctggtgaccgccaggaccccacggtgacctgcgtggtagtagatctcgatcccgaaaacccagaggtgca aatcagctggacgtggactctaagcaagtgcaaaccgccaacacgcaaccccgcgaggaacagagcaacggcacctacagggtggtgagcgtgctgcc catcgggcatcaggactggctgagcggcaagcagataaatgcaaggttaacaacaaggcactgcccagccccatcgaggagatcatcagcaagacccg ggacaggccccaccagcccaacgtgtacgtccacctccgagccgcgacgagatgagcaagaacaccgtgacgctgacctgtaggtgaaggacttcaccc acccgagatcgacgtggagtggcaaagcaatggccagcaggagcccgagagcaaataccaggatgaccccacccaactggatgaggatggcagctattt cctctacagcaaattgtccgtggacaaaagcaggtggcagaggggcgacaccacatctgcgccgtcatgcacgaggccatcacaatcactacacccaga tcagcctgagccactctcccggatag In the embodiment comprising the insulin-Fc fusion protein of SEQ ID NO: 45, the nucleic acid sequence (leader sequence underlined) is:

(SEQ ID NO: 46)
<u>atggaatggagctgggtctactatatcctgtcagtaacgactggtgtccactcct</u>cgtgaaccagcacctgtgcggctccgacctggtggaagctctggct ctcgtgtgcggcgagcgggcttcttctacaccgatcccactggaggcggtccacgcagaggcatcgtggaacagtgctgccactccatctgctccctgtac cagctggaaaaactactgcaatggcggaggtggtgcaggaggcggtggatgcatcagcccctgccccgtgccggagagcctgggtggccctagcgtgac atattccctcccaagcccaaggacatcctgaggatcaccaggaccccgagatcacctgtgtggtgctggatcaggcagggaagaccccgaagtccagat cagctggacgtggatggcaaggaggtgcacaccgccaagacccagccgagggagcagcagttcaactccacctacagggtggtgagcgtgctgcctatc gagcatcaggactggctgaccggcaaagagttcaagtgcagggtgaaccacatcggcctgcccagccccatcgaggaccatcagcaaagccagggg ccaggcccaccagcccagtgtgtacgtgatccccctagcccaaaggaactgagtagcagcgataccgtgaccctgacctgcctgatcaaggactttttccc gccagaaatagacgtggagtggcagagcaacggccagccggagcccgagagcaaataccacaccaccgcccctcaactggacgaggacgggagctac

```
acctgtatagcaagctgagcgttgacaagagcaggtggcaacagggcgacaccacctgcgccgtgatgcacgaagctctgcaaaaccactacaccga cctgtcactgagccatagcccggatag
```

In the embodiment comprising the insulin-Fc fusion protein of SEQ ID NO: 47, the nucleic acid sequence (leader sequence underlined) is:

(SEQ ID NO: 48)
```
aggaatggagctgggtctactatatcctgtcagtaacgactggtgtccttccacgtgaaccagcacctgtgcggctccgacctggtggaagctctggct ctcgtgtgcggcgagcgggcttcttctacaccgatcccactggaggcggtccacgcagaggcatcgtggaacagtgctgccactccatctgctccctgtac cagctggaaaactactgcaatggcggaggtggtgcaggaggcggtggagactgccccaagtgccccgctcccgagatgctgggcggacccagcgtgac atcaccctcccaagcccaaggacacactgctgatcgccaggaccccggaggtgacctgcgtggtggtggacctggatcccgaagaccccgaggtgcaga tcagctggttcgtggatggaaagcagatgcagaccgccaagacccaaccccgggaagagcagttcagcggcacctacagggtggtgagtgtgagcccat cggccaccaggactggctgaaggggaagcaattcacatgcaaggttaataacaaggccctgcccagcccatcgagaggaccatcagcaaggccaggg gccaggccaccagccatctgtgtacgtgctgcccccatctagggaggaactgagcaagaacacagtcagccttacttgcctgatcaaggacttcttcccac cggacatagacgtggagtggcagagtaacggccagcaggagcccgagagcaagtataggaccacaccgcccaactggacgaggacggaagctactt cctctacagcaaattgagcgttgacaaaagcaggtggcagcgaggcgacaccacatctgcgccgtgatgcacgaggctagcataaccactacacccagg agagcctgtcccacagcccggatag
```

In the embodiment comprising the insulin-Fc fusion protein of SEQ ID NO: 49, the nucleic acid sequence (leader sequence underlined) is:

(SEQ ID NO: 50)
```
atggaatggagctgggtctactatatcctgtcagtaacgactggtgtccactcatcgtgaaccagcacctgtgcggctcccacctggtggaagctctggct ctcgtgtgcggcgagcgggcttcttctacaccgatcccactggaggcggtccacgcagaggcatcgtggaacagtgctgcacctccatctgctccctgtac cagctggaaaactactgcaatggcggaggtggtgcaggaggcggtggagactgccccaagtgccccgctcccgagatgctgggcggacccagcgtgac atcaccctcccaagcccaaggacacactgctgatcgccaggaccccggaggtgacctgcgtggtggtggacctggatcccgaagaccccgaggtgcaga tcagctggttcgtggatggaaagcagatgcagaccgccaagacccaaccccgggaagagcagaccaaggcacctacagggtggtgagtgtgttgcccat cggccaccaggactggctgaaggggaagcaattcacatgcaaggttaataacaaggccctgcccagcccatcgagaggaccatcagcaaggccaggg gccaggccaccagccatctgtgtacgtgctgcccccatctagggaggaactgagcaagaacacagtcagccttacttgcctgatcaaggacttcttcccac cggacatagacgtggagtggcagagtaacggccagcaggagcccgagagcaagtataggaccacaccgcccaactggacgaggacggaagctactt cctctacagcaaattgagcgttgacaaaagcaggtggcagcgaggcgacaccacatctgcgccgtgatgcacgaggctagcataaccactacacccagg agagcctgtcccacagcccggatag
```

Insulin-Fc Fusion Protein Production

In embodiments, a fusion protein can be expressed by a cell as described in more detail in the Examples section.

Expression and Purification

In embodiments, an insulin-Fc fusion protein can be expressed recombinantly, e.g., in a eukaryotic cell, e.g., mammalian cell or non-mammalian cell. Exemplary mammalian cells used for expression include HEK cells (e.g., HEK293 cells) or CHO cells. CHO cells can be subdivided into various strains or subclasses, (e.g. CHO DG44, CHO-M, and CHO-K1), and some of these cell strains may be genetically engineered for optimal use with a particular type of nucleic acid molecule (e.g., a vector comprising DNA) or a particular cell growth media composition as described in the Examples section. In embodiments, cells are transfected with a nucleic acid molecule (e.g., vector) encoding the insulin-Fc fusion protein (e.g., where the entire insulin-Fc fusion protein is encoded by a single nucleic acid molecule). In embodiments, HEK293 cells are transfected with a vector that encodes for the insulin-Fc fusion protein, but only results in temporary expression of the insulin-Fc fusion protein for a period of time (e.g., 3 days, 4 days, 5, days, 7 days, 10 days, 12 days, 14 days, or more) before the host cell stops expressing appreciable levels of the insulin-Fc fusion protein (i.e., transient transfection). HEK293 cells that are transiently transfected with nucleic acid sequences encoding for insulin-Fc fusion proteins often allow for more rapid production of recombinant proteins which facilitates making and screening multiple insulin-Fc fusion protein candidates. In embodiments, CHO cells are transfected with a vector that is permanently incorporated into the host cell DNA and leads to consistent and permanent expression (i.e., stable transfection) of the insulin-Fc fusion protein as long as the cells are cultured appropriately. CHO cells and CHO cell lines that are stably transfected with nucleic acids encoding for insulin-Fc fusion proteins often take longer to develop, but they often produce higher protein yields and are more amenable to manufacturing low cost products (e.g., products for use in the veterinary pharmaceutical market). Cells and cell lines can be cultured using standard methods in the art.

In preferred embodiments, HEK cells comprising the cDNA sequence of with SEQ ID NO: 52 is used to express the insulin-Fc fusion protein of SEQ ID NO: 51. In preferred embodiments, CHO cells comprising any the cDNA sequence of SEQ ID NO: 52 is used to express the insulin-Fc fusion protein of SEQ ID NO: 51.

In some embodiments, the insulin-Fc fusion protein is purified or isolated from the cells (e.g., by lysis of the cells). In other embodiments, the insulin-Fc fusion protein is secreted by the cells and purified or isolated from the cell culture media in which the cells were grown. Purification of the insulin-Fc fusion protein can include using column chromatography (e.g., affinity chromatography) or using other separation methods based on differences in size, charge, and/or affinity for certain molecules. In embodiments, purification of the insulin-Fc fusion protein involves selecting or enriching for proteins containing an Fc fragment, e.g., by using Protein A beads or a Protein A column that cause proteins containing an Fc fragment to become bound with high affinity at neutral solution pH to the Protein A covalently conjugated to the Protein A beads. The bound insulin-Fc fusion protein may then be eluted from the Protein A beads by a change in a solution variable (e.g. a decrease in the solution pH). Other separation methods such as ion exchange chromatography and/or gel filtration chromatography can also be employed alternatively or additionally. In embodiments, purification of the insulin-Fc fusion protein further comprises filtering or centrifuging the protein preparation. In embodiments, further purification of the insulin-Fc fusion protein comprises diafiltration, ultrafiltration, and filtration through porous membranes of various sizes, as well as final formulation with excipients.

The purified insulin-Fc fusion protein can be characterized, e.g., for purity, protein yield, structure, and/or activity, using a variety of methods, e.g., absorbance at 280 nm (e.g., to determine protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to an anti-insulin antibody). Exemplary methods of characterization are also described in the Examples section.

In embodiments, the protein yield of an insulin-Fc fusion protein after production in transiently transfected HEK cells and protein A purification is greater than 5 mg/L, 10 mg/L, or 20 mg/L. In preferred embodiments, the protein yield of an insulin-Fc fusion protein after production in transiently transfected HEK cells and protein A purification is greater than 40 mg/L (e.g., greater than 60 mg/L, greater than 70 mg/L, greater than 80 mg/L, greater than 90 mg/L, greater than 100 mg/L). In embodiments, the % homodimer of an insulin-Fc fusion protein after production in transiently transfected HEK cells and protein A purification is greater than 70% (e.g., greater than 80%, greater than 85%, greater than 90%, greater than 95%, greater than 96%, greater than 97%, greater than 98%, greater than 99%). In embodiments, the homodimer titer of an insulin-Fc fusion protein after production in transiently transfected HEK cells and protein A purification, calculated as the product between the insulin-Fc fusion protein yield and the % homodimer is greater than 40 mg/L (e.g., greater than 50 mg/L, greater than 60 mg/L, greater than 70 mg/L, greater than 80 mg/L, greater than 90 mg/L, greater than 100 mg/L). Only candidates with a homodimer titer of greater than 40 mg/L were considered useful in the present invention, because experience has demonstrated that homodimer titers less than this level will not likely result in commercial production titers in CHO cells that meet the stringently low manufacturing cost requirements for veterinary products.

In embodiments, the protein yield of an insulin-Fc fusion protein after production in stably transfected CHO cells (e.g., CHO cell lines or CHO cell clones) and protein A purification is greater than 100 mg of insulin-Fc fusion protein per L (e.g. mg/L of culture media). In preferred embodiments, the protein yield of an insulin-Fc fusion protein after production in stably transfected CHO cells (e.g. CHO cell lines or CHO cell clones) and protein A purification is greater than 150 mg insulin-Fc fusion protein/L of culture media (e.g., greater than 200 mg/L, greater than 300 mg/L, greater than 400 mg/L, greater than 500 mg/L, greater than 600 mg/L or more). In embodiments, the % homodimer of an insulin-Fc fusion protein after production in stably transfected CHO cells (e.g. CHO cell lines or CHO cell clones) and protein A purification is greater than 70% (e.g., greater than 80%, greater than 85%, greater than 90%, greater than 95%, greater than 96%, greater than 97%, greater than 98%, greater than 99%). In embodiments, the homodimer titer of an insulin-Fc fusion protein after production in stably transfected CHO cells (e.g. CHO cell lines or CHO cell clones) and protein A purification, calculated as the product between the insulin-Fc fusion protein yield and the % homodimer is greater than 150 mg/L (e.g., greater than 200 mg/L, greater than 300 mg/L, greater than 400 mg/L, greater than 500 mg/L, greater than 600 mg/L or more).

Functional Features of Insulin-Fc Fusion Proteins

Described herein are methods for interacting with the insulin receptors to lower blood glucose in dogs, wherein the method comprises administering to a subject an insulin-Fc fusion protein, e.g., a fusion protein described herein. In some embodiments, the dog has been diagnosed with diabetes.

In embodiments, an insulin-Fc fusion protein described herein binds to the insulin receptor with an appreciable affinity as measured by the IC50 in the 4° C. IM-9 insulin receptor binding assay described in Example 11 (e.g. IC50 less than 5000 nM, IC50 less than 4000 nM, IC50 less than 3000 nM, IC50 less than 2500 nM). Based on experience, only compounds exhibiting insulin receptor activity IC50 values less than 5000 nM were deemed likely to exhibit bioactivity in the target species. Generally, higher affinity insulin receptor binding (i.e., lower IC50 values) is preferred. However, it is well-known that the clearance of insulin and insulin analogs (e.g., insulin polypeptides described herein) is governed primarily through binding to the insulin receptor followed by insulin receptor internalization and degradation within the cell. Therefore, insulin-Fc fusion proteins with too high of an insulin receptor binding affinity (i.e., too low of an IC50) may be cleared too quickly from circulation resulting in a lower than desired duration of glucose-lowering bioactivity in the target animal.

In embodiments, an insulin-Fc fusion protein described herein is capable of lowering glucose levels (e.g., blood glucose levels) after administration in a subject. In embodiments, the glucose lowering activity of the insulin-Fc fusion protein is greater than that of an insulin reference standard. In some embodiments, the duration of activity of the insulin-Fc fusion protein can be measured by a decrease, e.g., a statistically significant decrease, in fasting blood glucose relative to a pre-dose fasting blood glucose level. In embodiments, the duration of activity of the insulin-Fc fusion protein (e.g., the time during which there is a statistically significant decrease in fasting blood glucose level in a subject relative to a pre-dose level) is longer than about 2 hours. In embodiments, the duration of activity of the insulin-Fc fusion protein (e.g., the time during which there is a statistically significant decrease in blood glucose level in a subject relative to a pre-dose level) is longer than about 6 hours, 9 hours, 12 hours, 18 hours, 1 day, 1.5 days, 2 days, 2.5 days, 3 days, 4 days, 5 days, 6 days, 7 days, or longer. In embodiments, the insulin-Fc fusion protein is long-acting (e.g., has a long half-life, e.g., in serum).

In embodiments, the serum half-life of the insulin-Fc fusion protein in the dog is longer than that of an insulin reference standard or control formulation. In embodiments, the serum half-life of the insulin-Fc fusion protein (e.g., in the blood of a subject upon administration) in the dog is longer than about 2 hours. In embodiments, the serum half-life of the insulin-Fc fusion protein in the dog is about 0.5 days, 1 day, 2 days, or 2.5 days. In preferred embodiments, the serum half-life of the insulin-Fc fusion protein in the dog is about 3 days or longer.

In embodiments, the combination of potency and duration of bioactivity may be quantified by calculating the area over the percent fasting blood glucose (% FBGL) curve normalized to a given dose in mg/kg (NAOC) with units of % FBGL·days·kg/mg. In embodiments, the NAOC of the insulin-Fc fusion protein is greater than 150% FBGL·days·kg/mg (e.g. greater than 200% FBGL·days·kg/mg, greater than 250% FBGL·days·kg/mg or more). Again, based on experience, at NAOC values greater than 150% FBGL·days·kg/mg, the dose requirements in the target species will be sufficiently low so as to achieve an acceptable treatment cost. In embodiments, the NAOC of the insulin-Fc fusion protein must be maintained after repeated dosing in the target species (i.e., the ratio of the NAOC after the third dose to the NAOC after the first dose of the insulin-Fc fusion protein is greater than 0.50 (e.g., greater than 0.60, greater than 0.70. greater than 0.80, greater than 0.90, or more).

In some embodiments, the insulin-Fc fusion protein described herein binds to the Fc(gamma) receptor with an affinity that is lower than that of an insulin-Fc fusion protein reference standard as measured according to Example 12. In some embodiments, the ratio of the Fc(gamma) receptor affinity of the insulin-Fc fusion protein to that of an insulin-Fc fusion protein reference standard is less than 0.50 (e.g. less than 0.40, less than 0.30, less than 0.20).

Methods of Treatment and Characteristics of Subject Selection

Described herein are methods for treating canine diabetes, the methods comprising the administration of an insulin-Fc fusion protein (e.g., an insulin-Fc fusion protein described herein) to a subject.

In embodiments, a reference standard used in any method described herein comprises a reference treatment or reference therapy. In some embodiments, the reference comprises a standard of care agent for canine diabetes treatment. In some embodiments, the reference standard is a commercially available insulin or insulin analog. In some embodiments, the reference standard comprises a long-lasting insulin, intermediate-lasting insulin, short-lasting insulin, rapid-acting insulin, short-acting, intermediate-acting, long-acting insulin. In some embodiments, the reference standard comprises Vetsulin®, insulin NPH, insulin glargine (Lantus®), or recombinant human insulin.

In embodiments, a reference standard used in any method described herein includes an outcome, e.g., outcome described herein, of a canine diabetes therapy.

In embodiments, a reference standard is a level of a marker (e.g., blood glucose or fructosamine) in the subject prior to initiation of a therapy, e.g., an insulin-Fc fusion protein therapy described herein; where the subject has diabetes. In embodiments, the blood glucose level in a dog is greater than 200 mg/dL (e.g. greater than 250 mg/dL, 300 mg/dL, 350 mg/dL, 400 mg/dL or more) prior to initiation of therapy. In embodiments, the fructosamine level in a dog is greater than 250 micromol/L, 350 micromol/L (e.g. greater than 400 micromol/L, 450 micromol/L, 500 micromol/L, 550 micromol/L, 600 micromol/L, 650 micromol/L, 700 micromol/L, 750 micromol/L or more) prior to initiation of therapy. In embodiments, a reference standard is a measure of the presence of or the progression of or the severity of the disease. In embodiments, a reference standard is a measure of the presence of or the severity of the disease symptoms prior to initiation of a therapy, e.g., an insulin-Fc fusion protein therapy described herein, e.g., where the subject has diabetes.

Pharmaceutical Compositions and Routes of Administration

Provided herein are pharmaceutical compositions containing an insulin-Fc fusion protein described herein that can be used to lower blood glucose in dogs. The amount and concentration of the insulin-Fc fusion protein in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Formulations of the present disclosure include those suitable for parenteral administration. The phrases "parenteral administration" and "administered parenterally" as used herein means modes of administration other than enteral and topical administration, usually by intravenous or subcutaneous injection.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., polysorbate-20, Tween-20 or Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, the concentration of the insulin-Fc fusion protein in the aqueous carrier is about 3 mg/mL. In some embodiments, the concentration of the insulin-Fc fusion protein in the aqueous carrier is about 6 mg/mL. In some embodiments, the concentration of the insulin-Fc fusion protein in the aqueous carrier is about 8 mg/mL, 9 mg/mL, 10 mg/mL, 12 mg/mL, 15 mg/mL or more.

In some embodiments, the insulin-Fc fusion protein is administered as a bolus, infusion, or an intravenous push. In some embodiments, the fusion protein is administered through syringe injection, pump, pen, needle, or indwelling catheter. In some embodiments, the insulin-Fc fusion protein is administered by a subcutaneous bolus injection. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Dosages

Actual dosage levels of the insulin-Fc fusion protein can be varied so as to obtain an amount of the active ingredient that is effective to achieve the desired therapeutic response for a particular dog. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the subject being treated, and like factors well known in the medical arts.

In general, a suitable dose of an insulin-Fc fusion protein will be the amount that is the lowest dose effective to produce a therapeutic effect. Such an effective dose will generally depend upon the factors described above. Generally, intravenous and subcutaneous doses of the insulin-Fc fusion protein for a dog will range from about 0.001 to about 1 mg per kilogram (e.g. mg/kg) of body weight per day, e.g., about 0.001 to 1 mg/kg/day, about 0.01 to 0.1 mg/kg/day, about 0.1 to 1 mg/kg/day, or about 0.01 to 1 mg/kg/day. In still other embodiments, the fusion protein is administered at a dose between 0.025 and 4 mg per kilogram of body weight per week, e.g., between 0.025 and 0.5 mg/kg/week.

The present disclosure contemplates formulation of the insulin-Fc fusion protein in any of the aforementioned pharmaceutical compositions and preparations. Furthermore, the present disclosure contemplates administration via any of the foregoing routes of administration. One of skill in the art can select the appropriate formulation and route of administration based on the condition being treated and the overall health, age, and size of the patient being treated.

EXAMPLES

The present technology is further illustrated by the following Examples, which should not be construed as limiting in any way.

General Methods, Assays, and Materials

Example 1: Synthesis and Methods of Making an Insulin-Fe Fusion Protein in HEK293 Cells Insulin-Fc fusion proteins were synthesized as follows. A gene sequence of interest was constructed using proprietary software (LakePharma, Belmont, Calif.) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a suspension of HEK293 cells using the (LakePharma, Belmont, Calif.) standard operating procedure for transient transfection. After 20 hours, the cells were counted to determine the viability and viable cell count, and the titer was measured by FortéBio® Octet® (Pall FortéBio LLC, Fremont, Calif.). Additional readings were taken throughout the transient transfection production run. The culture was harvested on or after day 5.

Example 2: Synthesis and Methods of Making an Insulin-Fe Fusion Protein in HEK293 Cells Insulin-Fc fusion proteins are synthesized as follows. A gene sequence of interest is constructed using proprietary software (LakePharma, Belmont, Calif.) and is cloned into a high expression mammalian vector. HEK293 cells are seeded in a shake flask 24 hours before transfection and are grown using serum-free chemically defined media. A DNA expression construct that encodes the insulin-Fc fusion protein of interest is transiently transfected into a suspension of HEK293 cells using the (LakePharma, Belmont, Calif.) standard operating procedure for transient transfection. After 20 hours, the cells are counted to determine the viability and viable cell count, and the titer is measured by FortéBio® Octet® (Pall FortéBio LLC, Fremont, Calif.). Additional readings are taken throughout the transient transfection production run. The culture is harvested on or after day 5.

Example 3: Purification of an Insulin-Fe Fusion Protein

Purification of an insulin-Fc fusion protein was performed as follows. Conditioned media supernatants containing the secreted insulin-Fc fusion protein were harvested from the transiently or stably transfected HEK production runs and were clarified by centrifugation. The supernatant containing the desired insulin-Fc fusion protein was run over a Protein A or a Protein G column and eluted using a low pH gradient. Optionally, recovery of the insulin-Fc fusion proteins could be enhanced by reloading of the initial Protein A or Protein G column eluent again onto a second Protein A or Protein G column. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography (e.g. using an anion exchange bead resin or a cation exchange bead resin), gel filtration chromatography, or other methods was performed as necessary.

Example 4: Purification of an Insulin-Fe Fusion Protein

Purification of an insulin-Fc fusion protein is performed as follows. Conditioned media supernatants containing the secreted insulin-Fc fusion protein are harvested from the transiently or stably transfected HEK production runs and are clarified by centrifugation. The supernatant containing the desired insulin-Fc fusion protein is run over a Protein A or a Protein G column and eluted using a low pH gradient. Optionally, recovery of the insulin-Fc fusion proteins can be enhanced by reloading of the initial Protein A or Protein G column eluent again onto a second Protein A or Protein G column. Afterwards, the eluted fractions containing the desired protein are pooled and buffer exchanged into 200 mM HEPES, 100 mM NaCl, 50 mM NaOAc, pH 7.0 buffer. A final filtration step is performed using a 0.2 µm membrane filter. The final protein concentration is calculated from the solution optical density at 280 nm. Further optional purification by ion-exchange chromatography (e.g. using an anion exchange bead resin or a cation exchange bead resin), gel filtration chromatography, or other methods is performed as necessary.

Example 5: Structure Confirmation by Non-Reducing and Reducing CE-SDS

Capillary electrophoresis sodium dodecyl sulfate (CE-SDS) analysis was performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (e.g. using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 6: Structure Confirmation by Non-Reducing and Reducing CE-SDS

Capillary electrophoresis sodium dodecyl sulfate (CE-SDS) analysis is performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram is plotted. Under non-reducing conditions, the sample is run against known molecular weight (MW) protein standards, and the eluting peak represents the 'apparent' MW of the insulin-Fc fusion protein homodimer.

Under reducing conditions (e.g. using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 7: Sequence Identification by LC-MS with Glucan Removal

To obtain an accurate estimate of the insulin-Fc mass via mass spectroscopy (MS), the sample was first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution was first buffer exchanged into 0.1 M Tris, pH 8.0 buffer containing 5 mM EDTA using a Zeba desalting column (Pierce, ThermoFisher Scientific, Waltham, Mass.). 1.67 µL of PNGase F enzyme (Prozyme N-glycanase) was added to this solution in order to remove N-linked glycan present in the fusion protein (e.g., glycan linked to the side chain of the asparagine located at the cNg-N site), and the mixture was incubated at 37° C. overnight in an incubator. The sample was then analyzed via LC-MS (NovaBioassays, Woburn, Mass.) resulting in a molecular mass of the molecule which corresponds to the desired homodimer without the glycan. This mass was then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

Example 8: Sequence Identification by LC-MS with Glycan Removal

To obtain an accurate estimate of the insulin-Fc mass via mass spectroscopy (MS), the sample is first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, Mass.). 1.67 µL of PNGase F enzyme (Prozyme N-glycanase) is added to this solution in order to remove N-linked glycan present in the fusion protein (e.g., glycan linked to the side chain of the asparagine located at the cNg-N site), and the mixture is incubated at 37° C. overnight in an incubator. The sample is then analyzed via LC-MS (NovaBioassays, Woburn, Mass.) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

Example 9: % Homodimer by Size-Exclusion Chromatography

Size-exclusion chromatography (SEC-HPLC) of insulin-Fc fusion proteins was carried out using a Waters 2795HT HPLC (Waters Corporation, Milford, Mass.) connected to a 2998 Photodiode array at a wavelength of 280 nm. 100 µL or less of a sample containing an insulin-Fc fusion protein of interest was injected into a MAbPac SEC-1, 5 µm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g. multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained.

Example 10: % Homodimer by Size-Exclusion Chromatography

Size-exclusion chromatography (SEC-HPLC) of insulin-Fc fusion proteins is carried out using a Waters 2795HT HPLC (Waters Corporation, Milford, Mass.) connected to a 2998 Photodiode array at a wavelength of 280 nm. 100 μL or less of a sample containing an insulin-Fc fusion protein of interest is injected into a MAbPac SEC-1, 5 μm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g. multimers of insulin-Fc fusion protein homodimers) elute at earlier retention times, and the non-aggregated homodimers elute at later retention times. In separating the mixture of homodimers from aggregated multimeric homodimers via analytical SEC-HPLC, the purity of the insulin-Fc fusion protein solution in terms of the percentage of non-aggregated homodimer is ascertained.

Example 11: In Vitro IM-9 Insulin Receptor Binding of an Exemplary Insulin-Fc Fusion Protein at 4° C.

Human IM-9 cells (ATTC #CCL-159) that express human insulin receptor were cultured and maintained in complete RPMI 5% FBS medium at 70-80% confluency. Cultures of IM-9 cells were centrifuged at 250×g (~1000 rpm) for 10 min to pellet the cells. Cells were washed once with HBSS or PBS buffer, resuspended in cold FACS staining medium (HBSS/2 mM EDTA/0.1% Na-azide+4% horse serum) to a concentration of 8×106 cells/mL and kept on ice or 4° C. until test solutions were made. The insulin-Fc protein was diluted in FACS buffer in 1:3 serial dilutions as 2× concentrations in 1.2 mL tubes (approx. 60 μL volume of each dilution), and the solutions were kept cold on ice until ready for pipetting.

Biotinylated-RHI was diluted in FACS staining medium to a concentration of 1.25 μg/mL. 40 μL of the serially diluted test compound and 8 μL of 1.25 μg/mL Biotin-RHI were added into each well of a V bottom microtiter plate, mixed by slow vortexing, and placed on ice. 40 μL of an IM-9 cell suspension (8×106 cells/mL) was then added to each well by multichannel pipette, mixed again gently and incubated on ice for 30 min to allow competitive binding on the insulin receptor on IM-9 cells. Cells were then washed twice with 275 μL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells were then resuspended in 40 μL of FACS staining medium containing 1:100 diluted Streptavidin-PE (Life Technologies) for 20 min on ice. Cells were then washed once with 275 μL of ice-cold FACS buffer and finally fixed with 3% paraformaldehyde for 10 min at room temp. Cells were then washed once with 275 μL of ice-cold FACS buffer and resuspended in 250 μl of FACS buffer for analysis.

The V-bottom plates containing cells were then analyzed on a Guava 8-HT flow cytometer (Millipore). Biotinylated-RHI binding to insulin receptor was quantitated by the median fluorescence intensity (MFI) of the cells on the FACS FL-2 channel for each concentration of the test compound. Control wells were labeled only with biotinylated-RHI and were used to calculate the percent (%) inhibition resulting from each test compound concentration. The % inhibition by test compounds of biotinylated-RHI binding on IM-9 cells was plotted against log concentrations of the test compound, and the resulting IC50 values were calculated using GraphPad Prism (GraphPad Software, La Jolla, Calif.) for the test compounds. Lower IC50 values of the test compound therefore indicate greater levels of biotinylated-RHI inhibition at lower concentrations indicating stronger binding of the insulin-Fc fusion protein to the insulin receptor. A control compound, such as unlabeled recombinant human insulin (RHI) was also used as an internal standard to generate an RHI IC50 against which a given compound IC50 could be ratioed (IC50(compound)/IC50(RHI)). Lower IC50 ratios have more similar binding to RHI (stronger binding to insulin receptor), while higher IC50 ratios have weaker binding to the insulin receptor relative to RHI.

Example 12: In Vitro Fc(Gamma) Receptor I Binding Affinity Assay

The binding of insulin-Fc fusion proteins to the Fc(gamma) receptor I at pH 7.4 was conducted using an ELISA assay as follows. Since canine Fc(gamma) receptor I was not commercially available, human Fc(gamma) receptor I (i.e., rhFc(gamma) receptor I) was used as a surrogate mammalian receptor. Insulin-Fc compounds were diluted to 10 μg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated rhFc(gamma) receptor I (recombinant human Fc(gamma)R-I; R&D Systems) were prepared in PBST/10% Superblock buffer from 6000 ng/mL to 8.2 ng/mL and loaded at 100 μL/well onto the microplate strips coated with insulin-Fc fusion protein. The microtiter plate was incubated for 1 hour at room temperature after which the microplate strips were washed 5 times with PBST and then loaded with 100 μL/well of streptavidin-HRP diluted 1:10000 in PBST/10% Superblock buffer. After incubating for 45 min, the microplate strips were washed again 5 times with PBST. TMB was added to reveal the bound Fc(gamma) receptor I proteins and stopped with ELISA stop reagent (Boston Bioproducts). The plate was read in an ELISA plate reader at 450 nm, and the OD values (proportional to the binding of rhFc(gamma) receptor I to insulin-Fc protein) were plotted against log concentrations of rhFc(gamma) receptor I added to each well to generate binding curves using GraphPad Prism software.

Example 13: Generalized Procedure for Determination of In Vivo Pharmacodynamics (PD) after Single Administration of Insulin Fc-Fusion Proteins in Dogs Insulin-Fc fusion proteins were assessed for their effects on fasting blood glucose levels as follows. N=1, 2, 3 or more healthy, antibody-naïve, dogs weighing approximately 10-15 kg were used, one for each insulin-Fc fusion protein. Dogs were also observed twice daily for signs of anaphylaxis, lethargy, distress, pain, etc., and, optionally for some compounds, treatment was continued for an additional three weekly subcutaneous injections or more to observe if the glucose lowering capability of the compounds lessened over time, a key sign of potential induction of neutralizing anti-drug antibodies. On day 0, the dogs received a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-

0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 mM and at 1, 2, 3, 4, 5, 6 and 7 days post injection.

For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from day 0 to day 7 were plotted to assess the bioactivity of a given insulin-Fc fusion protein.

Example 14: Generalized Procedure for Determination of In Vivo Pharmacodynamics (PD) after Single Administration of Insulin Fc-Fusion Proteins in Dogs Insulin-Fc fusion proteins are assessed for their effects on fasting blood glucose levels as follows. N=1, 2, 3 or more healthy, antibody-naïve, dogs weighing approximately 10-15 kg are used, one for each insulin-Fc fusion protein. Dogs are also observed twice daily for signs of anaphylaxis, lethargy, distress, pain, etc., and, optionally for some compounds, treatment is continued for an additional three weekly subcutaneous injections or more to observe if the glucose lowering capability of the compounds lessened over time, a key sign of potential induction of neutralizing anti-drug antibodies. On day 0, the dogs receive a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood is collected from a suitable vein immediately prior to injection and at 15, 30, 45, 60, 120, 240, 360, and 480 min and at 1, 2, 3, 4, 5, 6 and 7 days post injection.

For each time point, a minimum of 1 mL of whole blood is collected. A glucose level reading is immediately determined using a glucose meter (ACCU-CHEK® Aviva Plus), which requires approximately one drop of blood. Average % fasting blood glucose levels (% FBGL) from day 0 to day 7 are plotted to assess the bioactivity of a given insulin-Fc fusion protein.

Example 15: Generalized Procedure for Determination of In Vivo Pharmacodynamics (PD) after Repeated Administration of Insulin-Fc Fusion Proteins in Canines Insulin-Fc fusion proteins were assessed for their effects on blood glucose levels over repeated injections as follows. Healthy, antibody-naïve, dogs weighing approximately between 5 and 20 kg were used, and each animal was administered doses of an insulin-Fc fusion protein. Animals were observed twice daily for signs of anaphylaxis, lethargy, distress, pain, and other negative side effects, and optionally for some compounds, treatment was continued for up to an additional two to five subcutaneous injections to observe if the glucose lowering capability of the compounds decreased over time, indicating the possible presence of neutralizing anti-drug antibodies in vivo. On day 0, the animals received a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood was collected from a suitable vein immediately prior to injection and at 15, 30, 45, 60, 120, 240, 360, and 480 min and at 1, 2, 3, 4, 5, 6 and 7 days post injection.

Subsequent subcutaneous injections were given no more frequently than once-weekly, and in some cases the injections were given at different intervals based on the pharmacodynamics of a given insulin-Fc fusion protein formulation. Subsequent injections for each insulin-Fc fusion protein were adjusted to higher or lower doses, depending on the demonstrated pharmacodynamics of the insulin-Fc fusion protein. For instance, if the dose of a first injection on day 0 was found to be ineffective at lowering blood glucose, the subsequent dose levels of injected insulin-Fc fusion protein were adjusted upward. In a similar manner, if the dose of a first injection on day 0 was found to lower glucose in too strong a manner, then subsequent dose levels of injected insulin-Fc fusion protein were adjusted downward. It was also found that interim doses or final doses could be adjusted in a similar manner as needed. For each dose, blood was collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from throughout the study were plotted against time which allows the bioactivity of a fusion protein to be determined.

To determine the bioactivity of each dose, an area-over-the-curve (AOC) analysis was conducted as follows. After constructing the % FBGL versus time data, the data was then entered into data analysis software (GraphPad Prism, GraphPad Software, San Diego Calif.). The software was used to first conduct an area-under-the curve analysis (AUC) to integrate the area under the % FBGL vs. time curve for each dose. To convert the AUC data into the desired AOC data, the following equation was used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL·days, gives the following for AOC: AOC=(100% FBGL×7 days)−(500% FBGL·days)=200% FBGL·days. The analysis can be performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose is calculated as follows: NAOC=AOC/D with units of % FBGL·days·kg/mg; where D is the actual dose injected into the animal in mg/kg. NAOC values may be calculated for each injection in a series of injections for a given animal and may be averaged across a group of animals receiving the same insulin-Fc fusion protein formulation.

The NAOC ratio (NAOCR) may also be calculated for each injection in a series of injections for a given animal by taking the NAOC values for each injection (e.g. injections 1, 2, 3, . . . N) and dividing each NAOC for a given injection by the NAOC from injection 1 as follows: NAOCR=(NAOC (Nth injection)/NAOC(injection 1)). By evaluating the NAOCR of a given insulin-Fc homodimer fusion protein formulation for the Nth injection in a series of injections, it is possible to determine whether the in vivo glucose lowering activity of a given insulin-Fc fusion protein has substantially retained its bioactivity over a series of N doses (e.g., NAOCR for the Nth dose of greater than 0.5) or whether the in vivo glucose lowering activity of a given insulin-Fc fusion protein has lost a substantial portion of its potency (e.g., NAOCR of the Nth dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection is greater than 0.5 (i.e., the NAOCR of the third subcutaneous injection is greater than 0.5).

Example 16: Generalized Procedure for Determination of In Vivo Pharmacodynamics (PD) after Repeated Administration of Insulin-Fc Fusion Proteins in Canines Insulin-Fc fusion proteins are assessed for their effects on blood glucose levels over repeated injections as follows. Healthy, antibody-naïve, dogs weighing approximately between 5 and 20 kg are used, and each dog is administered doses of an insulin-Fc fusion protein. Dogs are observed twice daily for signs of anaphylaxis, lethargy, distress, pain, and other negative side effects, and optionally for some compounds, treatment is continued for up to an additional two to five subcutaneous injections to observe if the glucose lowering capability of the compounds decreases over time, indicating the possible presence of neutralizing anti-drug antibodies in vivo. On day 0, the animals receive a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On day 0, blood is collected from a suitable vein immediately prior to injection and at 15, 30, 45, 60, 120, 240, 360, and 480 min and at 1, 2, 3, 4, 5, 6 and 7 days post injection.

Subsequent subcutaneous injections are given no more frequently than once-weekly, and in some cases the injections are given at different intervals based on the pharmacodynamics of a given insulin-Fc fusion protein formulation. Subsequent injections for each insulin-Fc fusion protein are adjusted to higher or lower doses, depending on the demonstrated pharmacodynamics of the insulin-Fc fusion protein. For instance, if the dose of a first injection on day 0 is found to be ineffective at lowering blood glucose, the subsequent dose levels of injected insulin-Fc fusion protein are adjusted upward. In a similar manner, if the dose of a first injection on day 0 was found to lower glucose in too strong a manner, then subsequent dose levels of injected insulin-Fc fusion protein are adjusted downward. Interim doses or final doses can be adjusted in a similar manner as needed. For each dose, blood is collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood is collected. A glucose level reading is immediately determined using a glucose meter (ACCU-CHEK® Aviva Plus), which requires approximately one drop of blood. Average % fasting blood glucose levels (% FBGL) from throughout the study are plotted against time which allows the bioactivity of a fusion protein to be determined.

To determine the bioactivity of each dose, an area-over-the-curve (AOC) analysis is conducted as follows. After constructing the % FBGL versus time data, the data is then entered into data analysis software (GraphPad Prism, GraphPad Software, San Diego Calif.). The software is used to first conduct an area-under-the curve analysis (AUC) to integrate the area under the % FBGL vs. time curve for each dose. To convert the AUC data into the desired AOC data, the following equation is used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL·days, gives the following for AOC: AOC=(100% FBGL×7 days)−(500% FBGL·days)=200% FBGL·days. The analysis can be performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose is calculated as follows: NAOC=AOC/D with units of % FBGL·days·kg/mg; where D is the actual dose injected into the animal in mg/kg. NAOC values may be calculated for each injection in a series of injections for a given animal and may be averaged across a group of animals receiving the same insulin-Fc fusion protein formulation.

The NAOC ratio (NAOCR) may also be calculated for each injection in a series of injections for a given animal by taking the NAOC values for each injection (e.g. injections 1, 2, 3, . . . N) and dividing each NAOC for a given injection by the NAOC from injection 1 as follows: NAOCR=(NAOC (Nth injection)/NAOC(injection 1)). By evaluating the NAOCR of a given insulin-Fc homodimer fusion protein formulation for the Nth injection in a series of injections, it is possible to determine whether the in vivo glucose lowering activity of a given insulin-Fc fusion protein has substantially retained its bioactivity over a series of N doses (e.g., NAOCR for the Nth dose of greater than 0.5) or whether the in vivo glucose lowering activity of a given insulin-Fc fusion protein has lost a substantial portion of its potency (e.g., NAOCR of the Nth dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection is greater than 0.5 (i.e., the NAOCR of the third subcutaneous injection is greater than 0.5).

Example 17: Assay Protocol for Measuring Anti-Drug Antibodies in Canine Serum Maxisorp ELISA Plates (Nunc) are Coated with the Insulin-Fc Fusion Protein of Interest Diluted in coating buffer (pH=9.6 Carbonate-Biocarbonate buffer) at 10 µg/mL overnight at 4° C. for measuring ADAs against the test compound. For measuring ADAs against the insulin portion of the insulin-Fc fusion protein containing an Fc fragment of canine IgG origin, plates are coated with purified insulin at 30 µg/mL in coating buffer. Plates are then washed 5× with PBST (PBS+0.05% Tween 20) and blocked for at least 1 hour (or overnight) with SuperBlock blocking solution (ThermoFisher, Waltham Mass.). For calculating the ADAs in canine IgG units, strips are directly coated with 1:2 serial dilutions of canine IgG (Jackson Immunoresearch Laboratories, West Grove Pa.) in pH=9.6 Carb-Biocarb coating buffer at concentrations between 300-4.69 ng/ml overnight at 4° C. and used to create a 7-point pseudo-standard curve. The standards strip plates are also washed and blocked with SuperBlock blocking solution for at least 1 hour (or overnight).

Test serum samples are diluted to greater than or equal to 1:100 (typically tested as 1:200) in PBST/SB/20% HS sample dilution buffer (PBS+0.1% Tween 20+10% SuperBlock+20% horse serum) and added to the insulin-Fc fusion protein coated (or RHI coated) strips at 100 µL/well in duplicate. Duplicate strips of canine IgG coated standard strips are also added to each plate and filled with PBST/SB (PBS+0.1% Tween 20+10% SuperBlock) buffer at 100 µL/well. Plates are incubated for 1 hour at RT and then washed 5× with PBST. For detection of ADAs, HRP-conjugated Goat anti-feline IgG F(ab')2 (anti-feline IgG F(ab')2 reagent is cross-reacted to canine antibodies; Jackson Immunoresearch Laboratories, West Grove Pa.), which is diluted in PBST/SB to 1:10000 and added at 100 µL/well to both sample and standard wells and incubated for 45 minutes at RT in dark. Plates are washed 5× with PBST and then one time with deionized water and then developed by adding 100 µL/well TMB substrate (Invitrogen, ThermoFisher Scientific, Waltham Mass.) for 15-20 minutes at room temperature in the dark. Color development is then stopped by addition of 100 µL/well of ELISA Stop Solution (Boston Bioproducts) and the absorbance is read at 450 nm using a SpectraMax plate reader within 30 minutes. The anti-drug antibody concentration is determined by interpolating the OD values in the 4-PL pseudo-standard curve using SoftMax Pro Software (Molecular Devices, San Jose Calif.).

To demonstrate the specificity of the detected ADAs, an "inhibition" assay is carried out. In the drug inhibition ADA assay, serum samples are diluted 1:100 in PBST/SB/20% HS buffer and mixed with an equal volume of 300 µg/mL of the relevant therapeutic compound (final sample dilution at 1:200 and final inhibitory compound at 150 µg/mL) and incubated for 30-40 minutes at room temperature to allow anti-drug antibodies to bind the free inhibitor (i.e., the therapeutic compound). After pre-incubation, the samples are added to insulin-Fc fusion protein coated (or RHI coated) strips at 100 µL/well in duplicate. Samples diluted 1:200 in PBST/SB/20% HS buffer without the inhibitory compound are also tested in the sample plates along with duplicate strips of canine IgG coated standards. Remaining steps of the assay procedure are carried out as described above. The ADAs measured in the drug-inhibited wells are matched with the non-inhibited ADA concentrations to assess the specificity of the ADAs. If significant inhibition of ADA signals is observed in the drug-inhibited wells, this means the ADAs are specific to the therapeutic compound.

Example 18: Assay Procedure for Immunogenic Epitope Identification

Maxisorp ELISA microplates (Nunc) are coated with a library of insulin-Fc fusion protein homodimer compounds with known amino acid sequences, and the coated plates are blocked in a similar manner as described in the anti-drug antibody ELISA assay Example 17, except that each compound in the library is coated on a separate individual strip of ELISA microplate wells. The compounds in the library comprise a range of insulin-Fc fusion proteins with different insulin polypeptide amino acid compositions, including various B-chain, C-chain, and A-chain amino acid mutations, different linker compositions, and different Fc fragment compositions, including some of human origin. Separately, some plate strip wells are directly coated with 1:2 serial dilutions of canine IgG (Jackson Immunoresearch Laboratories, West Grove Pa.) for calculating the anti-drug antibodies (ADA) in canine IgG units, respectively, as described in Example 17.

Serum obtained from individual dogs receiving repeated doses of an insulin-Fc fusion protein is first screened on the anti-drug antibody ELISA assay (Example 17). Serum samples demonstrating moderate or high positivity (e.g. moderate or high titers of antibodies) on the assay of Example 17 are serially diluted (1:200 to 1:8000) in PBST/SB/20% HS sample dilution buffer (PBS+0.1% Tween 20+10% SuperBlock+20% horse serum) and added to the plates coated with the library of insulin-Fc fusion protein compounds for 1 hour at RT. Following incubation, the plates are washed 5 times with PBST. For detection of canine antibodies capable of cross-reacting to the coated compound library, HRP conjugated goat anti-feline IgG F(ab')2 (Jackson Immunoresearch Laboratories, West Grove Pa.), which is cross-reactive to canine IgGs, is diluted in PBST/SB to 1:10000 and added at 100 µL/well to both sample and standard wells and incubated for 45 min at RT in the dark. Plates are washed 5 times with PBST, once with deionized water, and developed by the adding 100 µL/well TMB substrate (Invitrogen, ThermoFisher Scientific, Waltham Mass.) for 15-20 min at RT in the dark. Color development is then stopped by addition of 100 µL/well of ELISA Stop Solution (Boston Bioproducts, Ashland Mass.) and absorbance is read at 450 nm using a SpectraMax plate reader within 30 min Anti-compound cross-reactive antibody concentrations present in the serum samples are determined by interpolating the OD values in the 4-PL pseudo-standard curve against the directly coated canine IgG antibody controls using SoftMax Pro Software (Molecular Devices, San Jose Calif.).

By correlating the resulting antibody concentrations from the assay with the known amino acid compositions of the coated insulin-Fc fusion protein library, one can determine whether particular amino acid mutations or epitopes are responsible for causing none, some, most, or all of the total antibody signal on the assay, indicating no binding, weak binding, or strong binding to various insulin-Fc fusion protein homodimers. The mutations or epitopes responsible for moderate or strong binding are herein referred to as immunogenic "hot spots".

Example 19: Design Process for Obtaining Insulin-Fe Fusion Proteins with High Homodimer Titers and Acceptable Levels of Acute and Repeated Dose Bioactivity in the Target Species The process for meeting the design goals described in the Detailed Description of the Invention comprised the following steps. First, the insulin polypeptide of SEQ ID NO: 15 or SEQ ID NO: 8 was combined with a species-specific Fc fragment of a particular IgG isotype and a linker such that the resulting insulin-Fc fusion protein was most likely to yield a long-acting bioactivity product with minimal immunogenicity (e.g., a species-specific IgG isotype was chosen with minimal Fc(gamma) receptor I binding). The DNA sequence coding for the desired fusion protein was prepared, cloned into a vector (LakePharma, San Carlos, Calif.), and the vector was then used to transiently transfect HEK cells according to the procedure described in Example 1. The insulin-Fc fusion protein was then purified according to Examples 3 and the overall protein yield and % homodimer measured according to Example 9. Only candidates with a homodimer titer of greater than 40 mg/L were considered acceptable, because titers less than this level are not likely to result in commercial production titers that meet the stringently low manufacturing cost requirements for veterinary products. Selected insulin-Fc fusion proteins were then screened for indicators of bioactivity through in vitro insulin receptor binding studies as described in Example 11. Based on experience, only compounds that exhibited IR activity IC50 values less than 5000 nM were deemed likely to exhibit bioactivity in the target species. Although the in vitro IR IC50 value is a useful qualitative screening tool, it utilizes human IM-9 cells which express the human insulin receptor and therefore it may not capture some of the small differences in affinity between the canine IR and the human IR. Furthermore, factors other than insulin receptor binding may influence a compound’s bioactivity in vivo (e.g., affinity for canine FcRn to allow for extended pharmacokinetic elimination half-lives in vivo). Therefore, selected insulin-Fc fusion proteins that were acceptable from a manufacturing and IR activity IC50 value standpoint were further screened for bioactivity in the animal of interest (e.g., dog or cat) to screen out any materials with less than the desired potency and/or duration of bioactivity (e.g., NAOC of less than 150% FBGL·days·kg/mg). Again, based on experience, at NAOC values of greater than 150% FBGL·days·kg/mg, the dose requirements in the target species will be sufficiently low so as to reach an acceptable treatment cost. Lastly, an additional evaluation criterion was added which is mentioned rarely if ever in the art. As discussed in more detail in the Examples below, many insulin-Fc fusion protein embodiments that exhibit acceptable NAOC levels in the target species after the first dose, unexpectedly fail to maintain that level of bioactivity after repeated doses. Furthermore, in most cases the reduction in repeated dose bioactivity in the target species is correlated with the development of neutralizing anti-drug antibodies. This propensity to generate anti-drug antibodies and the failure to maintain activity render such insulin-Fc fusion proteins impractical for use in treating a chronic disease such as canine diabetes. Therefore, only the insulin-Fc fusions proteins exhibiting acceptable levels of repeated dose bioactivity (e.g., NAOCR values greater than 0.50 for the third dose relative to the first dose) with minimal levels of anti-drug antibodies were deemed acceptable for use in the present invention.

Results—Insulin-Fc Fusion Proteins Comprising a Canine Fc Fragment

Example 20: Canine Insulin-Fe Fusion Protein Configurations Comprising the Canine Fc IgGA, IgGC and IgGD Isotypes An attempt was made to produce insulin-Fc fusion proteins comprising the insulin polypeptide sequences of SEQ ID NO: 15, SEQ ID NO: 16, SEQ ID NO: 23, and SEQ ID NO: 22, and the Fc fragment of the canine IgGA isotype (SEQ ID NO: 28), the canine IgGC isotype (SEQ ID NO: 30) or the canine IgGD isotype (SEQ ID NO: 31) using the peptide linker of SEQ ID NO: 26 or SEQ ID NO: 25. The full amino acid sequences for the resulting insulin-Fc fusion protein configurations are as follows:

(SEQ ID NO: 33)

```
FVNQHLCGSDLVEALALVCGERGFFYTDPTGGGPRRGIVEQCCHSICSLYQLENYCNGGGGAGGG
GRCTDTPPCPVPEPLGGPSVLIFPPKPKDILRITRTPEVTCVVLDLGREDPEVQISWFVDGKEVHTAK
TQSREQQFNGTYRVVSVLPIEHQDWLTGKEFKCRVNHIDLPSPIERTISKARGRAHKPSVYVLPPSPK
ELSSSDTVSITCLIKDFYPPDIDVEWQSNGQQEPERKHRMTPPQLDEDGSYFLYSKLSVDKSRWQQG
DPFTCAVMHETLQNHYTDLSLSHSPG
```

(SEQ ID NO: 35)

```
FVNQHLCGSDLVEALYLVCGERGFFYTDPTGGGPRRGIVEQCCHSICSLYQLENYCNGGGGSGGGG
RCTDTPPCPVPEPLGGPSVLIFPPKPKDILRITRTPEVTCVVLDLGREDPEVQISWFVDGKEVHTAKT
QSREQQFNGTYRVVSVLPIEHQDWLTGKEFKCRVNHIDLPSPIERTISKARGRAHKPSVYVLPPSPKE
LSSSDTVSITCLIKDFYPPDIDVEWQSNGQQEPERKHRMTPPQLDEDGSYFLYSKLSVDKSRWQQG
DPFTCAVMHETLQNHYTDLSLSHSPG
```

(SEQ ID NO: 37)
FVNQHLCGSHLVEALYLVCGERGFFYTPKAGGGPRRGIVEQCCTSICSLYQLENYCNGGGGSGGGG
RCTDTPPCPVPEPLGGPSVLIFPPKPKDILRITRTPEVTCVVLDLGREDPEVQISWFVDGKEVHTAKT
QSREQQFNGTYRVVSVLPIEHQDWLTGKEFKCRVNHIDLPSPIERTISKARGRAHKPSVYVLPPSPKE
LSSSDTVSITCLIKDFYPPDIDVEWQSNGQQEPERKHRMTPPQLDEDGSYFLYSKLSVDKSRWQQG
DPFTCAVMHETLQNHYTDLSLSHSPG (SEQ ID NO: 39)
FVNQHLCGSHLVEALYLVCGERGFFYTPKAAAAAAAKGIVEQCCTSICSLYQLENYCNGGGGSGG
GGRCTDTPPCPVPEPLGGPSVLIFPPKPKDILRITRTPEVTCVVLDLGREDPEVQISWFVDGKEVHTA
KTQSREQQFNGTYRVVSVLPIEHQDWLTGKEFKCRVNHIDLPSPIERTISKARGRAHKPSVYVLPPSP
KELSSSDTVSITCLIKDFYPPDIDVEWQSNGQQEPERKHRMTPPQLDEDGSYFLYSKLSVDKSRWQQ
GDPFTCAVMHETLQNHYTDLSLSHSPG The insulin-Fc fusion protein configuration of SEQ ID NO: 43, comprising the insulin polypeptide of SEQ ID NO: 16, the peptide linker of SEQ ID NO: 25 and the canine IgGC Fc fragment of SEQ ID NO: 30 yielded no material at all. The insulin-Fc fusion protein configuration of SEQ ID NO: 45, comprising the insulin polypeptide of SEQ ID NO: 16, the peptide linker of SEQ ID NO: 25 and the canine IgGD Fc fragment of SEQ ID NO: 31 yielded a good protein yield of 134 mg/L, however the material was highly aggregated with a % homodimer of 12.3% and a homodimer titer of 16.5 mg/L, which is significantly less than the required homodimer titer of 40 mg/L.

(SEQ ID NO: 43)
FVNQHLCGSDLVEALALVCGERGFFYTDPTGGGPRRGIVEQCCHSICSLYQLENYCNGGGGAGGGG
CNNCPCPGCGLLGGPSVFIFPPKPKDILVTARTPTVTCVVVDLDPENPEVQISWFVDSKQVQTANT
QPREEQSNGTYRVVSVLPIGHQDWLSGKQFKCKVNNKALPSPIEEIISKTPGQAHQPNVYVLPPSR
DEMSKNTVTLTCLVKDFFPPEIDVEWQSNGQQEPESKYRMTPPQLDEDGSYFLYSKLSVDKSRWQR
GDTFICAVMHEALHNHYTQISLSHSPG (SEQ ID NO: 45)
FVNQHLCGSDLVEALALVCGERGFFYTDPTGGGPRRGIVEQCCHSICSLYQLENYCNGGGGAGGGGC
ISPCPVPESLGGPSVFIFPPKPKDILRITRTPEITCVVLDLGREDPEVQISWFVDGKEVHTAKTQPRE
QQFNSTYRVVSVLPIEHQDWLTGKEFKCRVNHIGLPSPIERTISKARGQAHQPSVYVLPPSPKELSSS
DTVTLTCLIKDFFPPEIDVEWQSNGQPEPESKYHTTAPQLDEDGSYFLYSKLSVDKSRWQQGDTFTC
AVMHEALQNHYTDLSLSHSPG

The insulin-Fc fusion protein configurations of SEQ ID NO: 33, SEQ ID NO: 35, SEQ ID NO: 37, SEQ ID NO: 39, SEQ ID NO: 43 and SEQ ID NO: 45 were synthesized in HEK cells according to Example 1 and purified according to Example 3. The structure of the insulin-Fc fusion protein was confirmed according to Example 5 by non-reducing and reducing CE-SDS, and the sequence was further identified by LC-MS with glycan removal according to Example 7. The % homodimer was measured by size-exclusion chromatography according to Example 9. The results are given in Table 6. In summary, despite mutating the insulin polypeptide and/or the linker, there was no embodiment based on the canine IgGA Fc fragment (SEQ ID NO: 28) with a low enough degree of aggregation and a high enough titer of the desired homodimer.

TABLE 6

Homodimer titers for insulin-Fc fusion protein configurations utilizing canine IgG Fc Fragments

| SEQ ID NO: | Canine IgG | Protein Yield (mg/L) | % Homodimer | Homodimer Titer (mg/L) |
| --- | --- | --- | --- | --- |
| SEQ ID NO: 33 | IgGA | 22 | 24% | 5.28 |
| SEQ ID NO: 35 | IgGA | 21 | 19% | 3.99 |
| SEQ ID NO: 37 | IgGA | 11 | Not tested | ≤11 |
| SEQ ID NO: 39 | IgGA | 18 | Not tested | ≤18 |

TABLE 6-continued

Homodimer titers for insulin-Fc fusion protein configurations utilizing canine IgG Fc Fragments

| SEQ ID NO: | Canine IgG | Protein Yield (mg/L) | % Homodimer | Homodimer Titer (mg/L) |
| --- | --- | --- | --- | --- |
| SEQ ID NO: 43 | IgGC | 0 | Not tested | 0 |
| SEQ ID NO: 45 | IgGD | 134 | 12% | 16.5 |

Example 21: Canine Insulin-Fc Fusion Protein Configurations Comprising the Canine Fc IgGB Isotype On the other hand, replacing the canine IgGA Fc fragment (SEQ ID NO: 28) with the canine IgGB Fc fragment (SEQ ID NO: 29) yielded a much less aggregated compound with a comparatively high titer of the desired homodimer. The insulin-Fc fusion protein configuration of SEQ ID NO: 41, comprising the insulin polypeptide of SEQ ID NO: 16, the linker of SEQ ID NO: 25 and the canine IgGB Fc fragment of SEQ ID NO: 29 had a protein yield of 80 mg/L and a % homodimer of 93% resulting in a homodimer titer of 74.7 mg/L, which surpassed the required homodimer titer of 40 mg/L.

(SEQ ID NO: 41)
FVNQHLCGSDLVEALALVCGERGFFYTDPTGGGPRRGIVEQCCHSICSLYQLENYCNGGGGAGGG

GDCPKCPAPEMLGGPSVFIFPPKPKDTLLIARTPEVTCVVVDLDPEDPEVQISWFVDGKQMQTAKT

QPREEQFNGTYRVVSVLPIGHQDWLKGKQFTCKVNNKALPSPIERTISKARGQAHQPSVYVLPPSRE

ELSKNTVSLTCLIKDFFPPDIDVEWQSNGQQEPESKYRTTPPQLDEDGSYFLYSKLSVDKSRWQRGD

TFICAVMHEALHNHYTQESLSHSPG

Example 22: In Vitro IM-9 Insulin Receptor Binding of an Exemplary Insulin-Fc Fusion Protein at 4° C.

In vitro insulin receptor binding for the insulin-Fc fusion protein configurations of SEQ ID NO:25 (IgGA), SEQ ID NO: 41 (IgGB), SEQ ID NO: 43 (IgGC) and SEQ ID NO: 45 (IgGD) were tested according to the procedure of Example 11. As shown in Table 7, the insulin-Fc fusion protein of SEQ ID NO: 33 demonstrated in IR binding IC50 of 2733 and the insulin-Fc fusion protein of SEQ ID NO: 45 demonstrated an IR binding IC50 of greater than 5000 nM, indicating that neither insulin-Fc fusion protein configuration was highly unlikely to show bioactivity in vivo. The insulin-Fc fusion protein of SEQ ID NO: 43 had no yield and so the IR binding IC50 was not measure. However, the insulin-Fc fusion protein of SEQ ID NO: 41 demonstrated an IC50 of 28 nM indicating that this sequence was likely to be bioactive in vivo.

TABLE 7

Homodimer titers for sequences utilizing native canine IgGB, IgGC, and IgGD Fc fragments

| SEQ ID NO: | IgG Fragment | Protein Yield (mg/L) | % Homo-dimer | Homodimer Titer (mg/L) | IR Binding, IC50 (nM) |
|---|---|---|---|---|---|
| SEQ ID NO: 33 | IgGA | 22 | 24% | 5.28 | 2,733 |
| SEQ ID NO: 41 | IgGB | 80 | 93% | 74.4 | 28 |
| SEQ ID NO: 43 | IgGC | 0 | Not tested | 0 | DNM* |
| SEQ ID NO: 45 | IgGD | 134 | 12% | 16.5 | >5000 |

*DNM = Did Not Measure

Figure 5:
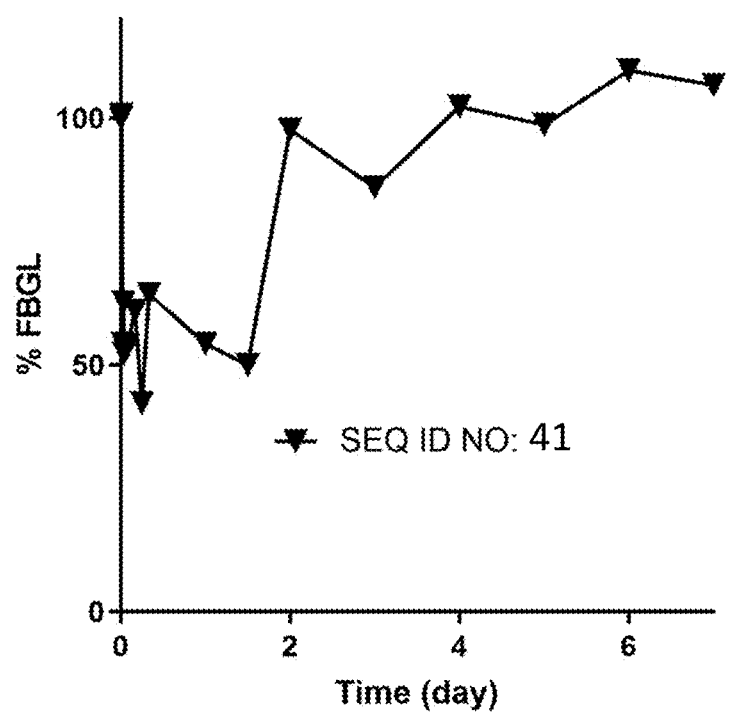
FIG. 5 shows average % fasting blood glucose levels from Day 0 to Day 7 for N=3 dogs dosed intravenously on Day 0 at 0.2 mg/kg with the homodimer of SEQ ID NO: 41.
Figure 6:
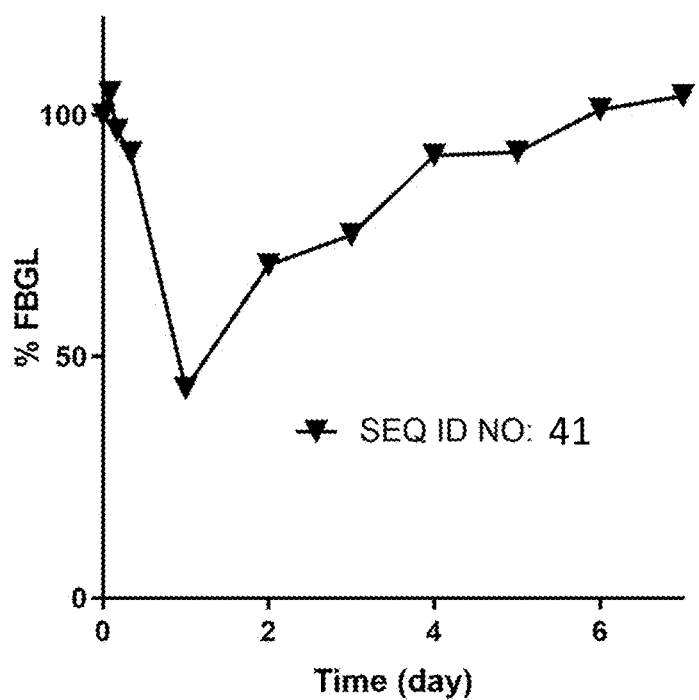
FIG. 6 shows average % fasting blood glucose levels from Day 0 to Day 7 for N=6 dogs dosed subcutaneously on Day 0 at 0.33 mg/kg with the homodimer of SEQ ID NO: 41.

Example 23: In Vivo Efficacy of an Insulin-Fc Fusion Protein Comprising the Insulin Polypeptide of SEQ ID NO: 16 with a Canine IgGB Isotype Fc Fragment Given the promising homodimer titer and insulin receptor activity results in Examples 17a and 17b, the insulin-Fc fusion protein of SEQ ID NO: 41 was tested for in vivo bioactivity according to Example 13 following an intravenous injection in each of N=3 healthy, antibody-naïve, beagle dogs weighing approximately 10 kg. In a separate experiment, the compound was administered subcutaneously to N=3 naïve beagle dogs. FIG. 5 shows the % FBGL versus time for a single intravenous administration of the insulin-Fc fusion protein of SEQ ID NO: 41, and FIG. 6 shows the % FBGL vs. time for a single subcutaneous administration of the insulin-Fc fusion protein of SEQ ID NO: 41, both of which demonstrate that the insulin-Fc fusion protein of SEQ ID NO: 41 is significantly bioactive in dogs.

Figure 2:
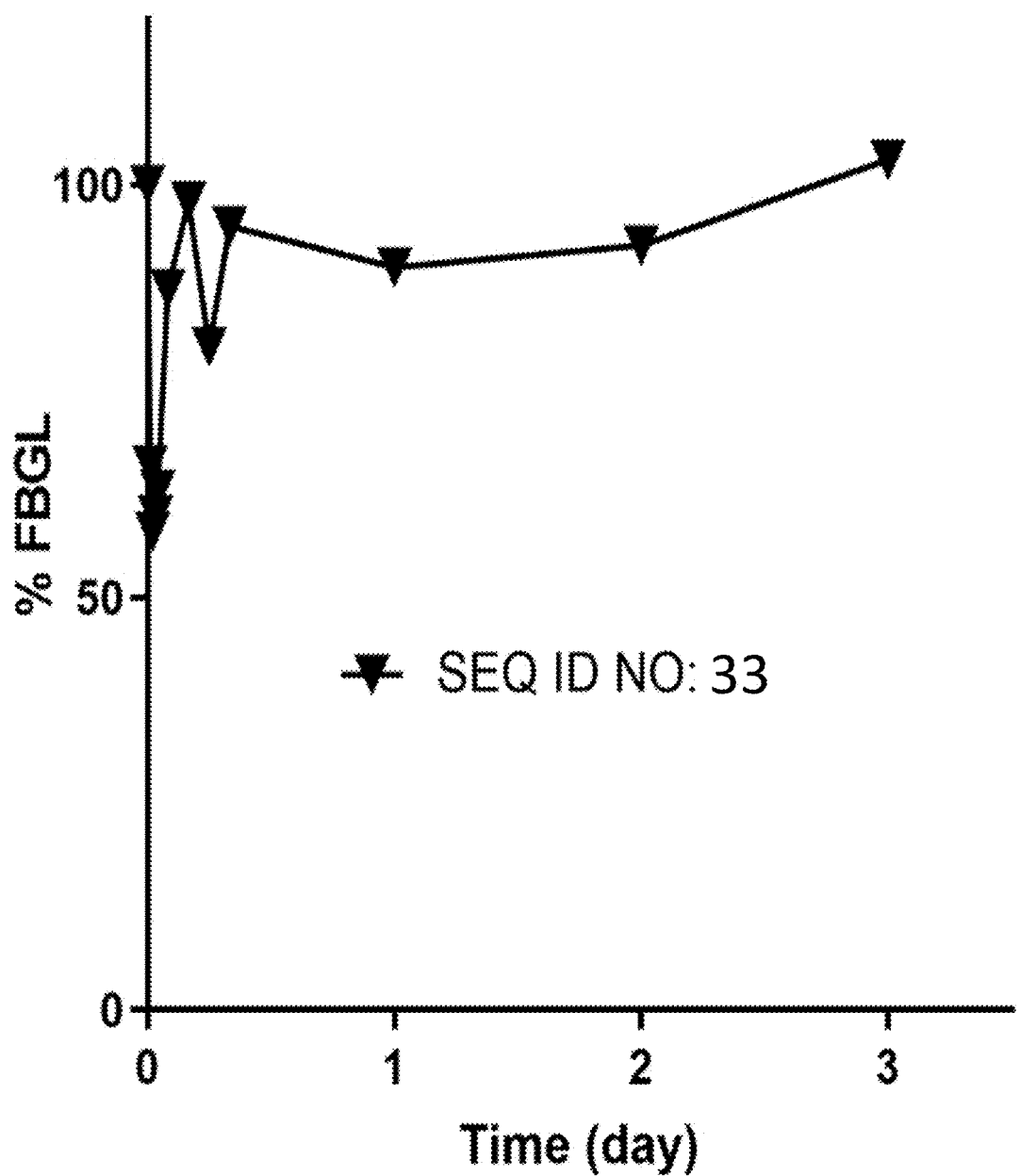
FIG. 2 shows average % fasting blood glucose levels from Day 0 to Day 3 for N=3 dogs dosed intravenously on Day 0 at 0.2 mg/kg with the homodimer of SEQ ID NO: 33.
Figure 8:
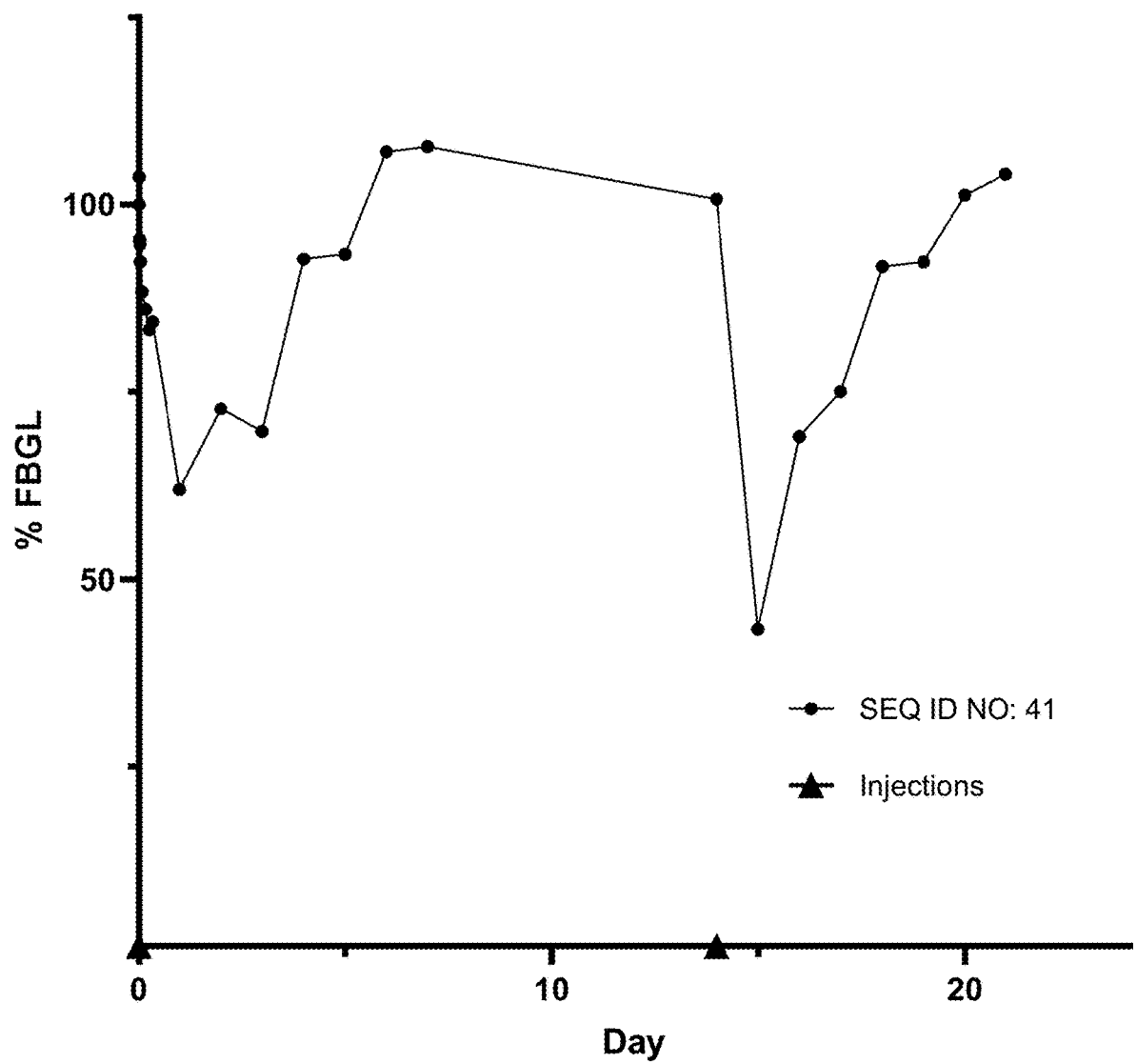
FIG. 8 shows % fasting blood glucose levels from Day 0 to Day 35 for N=1 dog dosed subcutaneously on Day 0, Day 14 and Day 21 with the homodimer of SEQ ID NO: 41.

The NAOC was calculated according to the procedure of Example 15 to determine the relative bioactivity and duration of action of the insulin-Fc fusion protein. The NAOC of the insulin-Fc fusion protein of SEQ ID NO: 41 injected intravenously was 399% FBGL·days·kg/mg which was 3.8 times the NAOC of the insulin-Fc fusion protein of SEQ ID NO: 33 injected intravenously, illustrating significantly increased bioactivity for the insulin-Fc fusion protein comprising the canine IgGB Fc fragment versus the insulin-Fc fusion protein comprising the canine IgGA Fc fragment. The in vivo bioactivity of SEQ ID NO: 33 is illustrated in FIG. 2. The NAOC of the insulin-Fc fusion protein of SEQ ID NO: 41 injected subcutaneously was 366% FBGL·days·kg/mg, demonstrating a level of bioactivity via subcutaneous administration that is similar to that obtained via intravenous administration. The in vivo bioactivity of SEQ ID NO: 41 across two doses is illustrated in FIG. 8.

Example 24: In Vivo Immunogenicity Screening After Repeated Subcutaneous Doses of the Insulin-Fc Fusion Protein Comprising the Insulin Polypeptide of SEQ ID NO: 41 with a Canine IgGB Isotype Fc Fragment Next, the repeated dose subcutaneous bioactivity of the insulin-Fc fusion protein of SEQ ID NO: 41 was tested in dogs as per the method described in Example 15. N=3 animals were dosed subcutaneously at day 0, at day 35, and at day 42, and the % FBGL was measured for the 7-day window after each dose according to Example 15. The NAOC and NAOCR were calculated according to the procedure of Example 15 for each repeated subcutaneous injection. As illustrated in Table 8, repeated subcutaneous dosing in dogs unexpectedly revealed a significant decay in bioactivity by the third dose as measured by a significant decrease in the NAOCR (i.e., the NAOC for the third injection was only 0.40, or 40%, of the NAOC for the first injection).

TABLE 8

NAOC per dose and NAOCR for repeated doses of SEQ ID NO: 42

| Injection Number of SEQ ID NO: 41 | NAOC (% FBGL · days · kg/mg) | NAOCR (ratioed to Week 1) |
|---|---|---|
| 1 | 330 | 1.0 |
| 2 | 339 | 1.1 |
| 3 | 115 | 0.4 |

Figure 7:
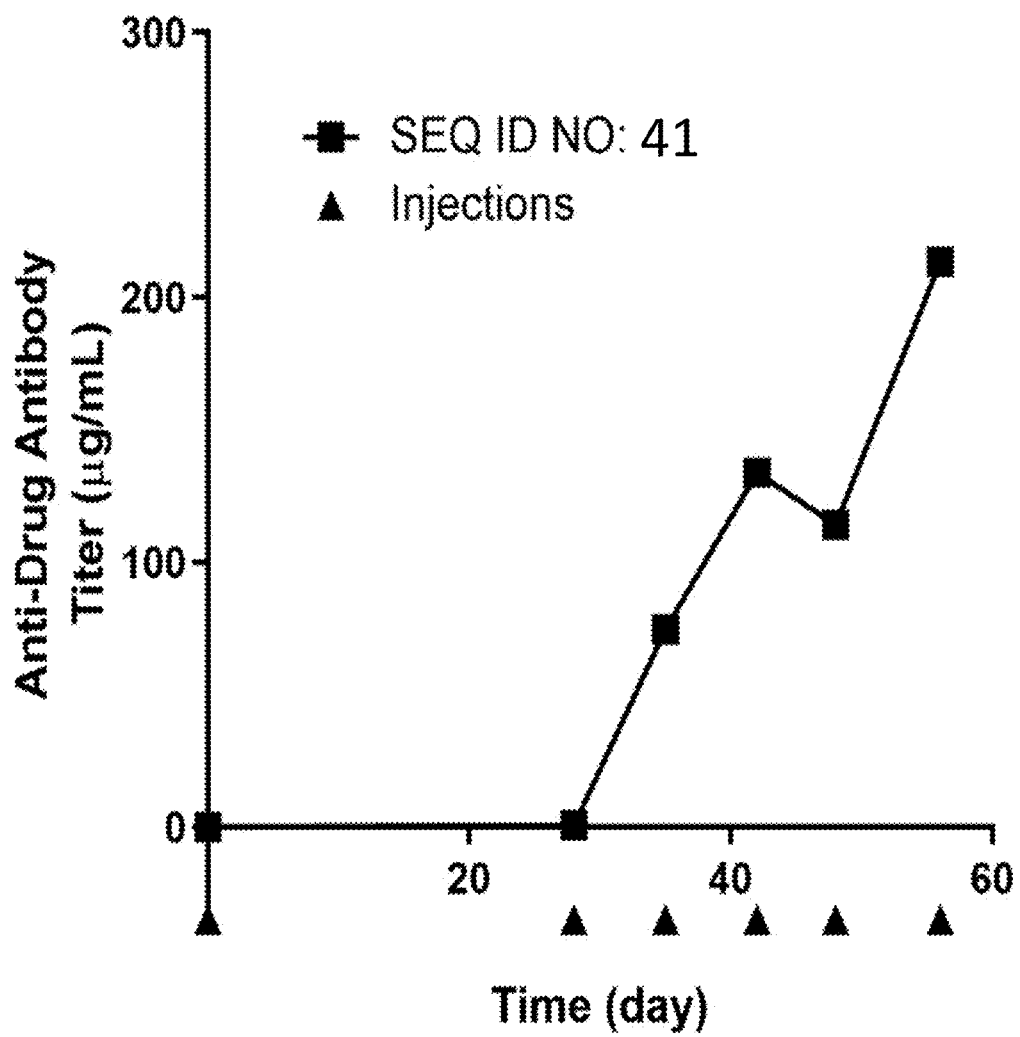
FIG. 7 shows the average anti-drug antibody titer (μg/mL) for N=3 dogs dosed subcutaneously on Day 0 (0.30 mg/kg), Day 28 (0.33 mg/kg), Day 35 (0.33 mg/kg), Day 42 (0.50 mg/kg), Day 49 (1.00 mg/kg) and Day 56 (1.00 mg/kg) with the homodimer of SEQ ID NO: 41.

Without being bound to any particular explanation, it was postulated that the cause of the significant reduction in bioactivity of the insulin-Fc fusion protein of SEQ ID NO: 41 after the third repeated subcutaneous dose in dogs was due to the development of anti-drug antibodies that neutralized its biological activity. Anti-drug antibodies may be directed against the insulin polypeptide, linker, or Fc-fragment portions of an insulin-Fc fusion protein. The immunogenic response manifests as interactions between antigen presenting cells, T-helper cells, B-cells, and their associated cytokines, which may lead to the production of endogenous antibodies against the drug (e.g. anti-drug antibodies). Binding antibodies are all isotypes capable of binding the insulin-Fc fusion protein, and these may be detected in an immunoassay as described in Example 17. Neutralizing antibodies that inhibit functional activity of the insulin-Fc fusion protein are generally directed against an epitope that is required for bioactivity. To assess whether this was the case, serum that was collected prior to the administration of each dose and at the end of the experiment described in Examples 11 was tested to quantify the levels of anti-drug antibodies according to Example 17. As shown in FIG. 7, levels of anti-drug antibodies did indeed increase with multiple subcutaneous administrations of the compound, indicating that the generation of neutralizing anti-drug antibodies were the likely cause for the reduction in the NAOCR after the third injection of the insulin Fc-fusion protein of SEQ ID NO: 41.

Example 25: Non-Glycosylated Insulin-Fe Fusion Protein Comprising the Insulin Polypeptide of SEQ ID NO: 16 with Canine IgGB Isotype Fc Fragments to Reduce the Potential Risk of Immunogenicity As shown in Example 21, Example 22 and Example 23, the insulin-Fc fusion protein of SEQ ID NO: 41 showed acceptable % homodimer content, homodimer titer, and bioactivity in dogs; however, its use for a chronic disease such as diabetes is compromised by the reduction in bioactivity and generation of anti-drug antibodies (Example 24) with repeated subcutaneous dosing. Without being bound to any particular theory, one possible cause of the generation of anti-drug antibodies and the reduction in bioactivity is the increased interaction of the canine IgGB Fc fragment with various receptors of the canine immune system (e.g. Fc(gamma) receptors, e.g. Fc(gamma)RI). Nevertheless, the canine IgGB isotype was the only one of the four canine IgG isotypes that, when used for the Fc fragment, resulted in an insulin-Fc fusion protein meeting the manufacturability and single-dose bioactivity design goals (Example 19). As described in the Detailed Description of the Invention, one method for reducing the Fc(gamma) interaction involves mutating the Fc fragment cNg site to prevent glycosylation during synthesis in the host cell.

Therefore, cNg site mutations were made to the Fc fragment region of SEQ ID NO: 41 to reduce the binding affinity of the Fc fragment for Fc(gamma) receptors in vivo, as measured by binding in an in vitro human Fc(gamma)RI assay described in Example 12. Verification of the lack of glycan were performed using the LC-MS method of Example 7, but with omission of the PNGase F treatment step. The position of the cNg site in the insulin-Fc fusion protein of SEQ ID NO: 41 is cNg-NB139. Mutations to SEQ ID NO: 41 included SEQ ID NO: 47 comprising a mutation of cNg-NB139-S, SEQ ID NO: 49 comprising a mutation of cNg-NB139-Q together with reverting to the native B10H and ABT, and SEQ ID NO: 51 comprising removal of the aspartic acid at the N-terminus of the Fc fragment (des hinge D) a mutation of cNg-NB138-K (due to the des hinge D mutation, the cNg site for SEQ ID NO: 51 is NB138 instead of NB139). The full amino acid sequences of the cNg-mutated insulin-Fc fusion proteins are listed below (with the cNg position underlined) and the resulting sequence alignments are shown in FIG. 4 (Clustal Omega):

(SEQ ID NO: 47)
FVNQHLCGSDLVEALALVCGERGFFYTDPTGGGPRRGIVEQCCHSICSLYQLENYCNGGGGAGGG

GDCPKCPAPEMLGGPSVFIFPPKPKDTLLIARTPEVTCVVVDLDPEDPEVQISWFVDGKQMQTAKT

QPREEQFSGTYRVVSVLPIGHQDWLKGKQFTCKVNNKALPSPIERTISKARGQAHQPSVYVLPPSRE

ELSKNTVSLTCLIKDFFPPDIDVEWQSNGQQEPESKYRTTPPQLDEDGSYFLYSKLSVDKSRWQRGD

TFICAVMHEALHNHYTQESLSHSPG (SEQ ID NO: 49)
FVNQHLCGSHLVEALALVCGERGFFYTDPTGGGPRRGIVEQCCTSICSLYQLENYCNGGGGAGGGG

DCPKCPAPEMLGGPSVFIFPPKPKDTLLIARTPEVTCVVVDLDPEDPEVQISWFVDGKQMQTAKTQ

PREEQFQGTYRVVSVLPIGHQDWLKGKQFTCKVNNKALPSPIERTISKARGQAHQPSVYVLPPSRE

ELSKNTVSLTCLIKDFFPPDIDVEWQSNGQQEPESKYRTTPPQLDEDGSYFLYSKLSVDKSRWQRG

DTFICAVMHEALHNHYTQESLSHSPG (SEQ ID NO: 51)
FVNQHLCGSDLVEALALVCGERGFFYTDPTGGGPRRGIVEQCCHSICSLYQLENYCNGGGGAGGGG

CPKCPAPEMLGGPSVFIFPPKPKDTLLIARTPEVTCVVVDLDPEDPEVQISWFVDGKQMQTAKTQP

REEQFKGTYRVVSVLPIGHQDWLKGKQFTCKVNNKALPSPIERTISKARGQAHQPSVYVLPPSREE

LSKNTVSLTCLIKDFFPPDIDVEWQSNGQQEPESKYRTTPPQLDEDGSYFLYSKLSVDKSRWQRGD

TFICAVMHEALHNHYTQESLSHSPG

The insulin-Fc fusion proteins were manufactured in HEK293 cells according to Example 1 and purified using a Protein A column according to Example 3. The structures of the insulin-Fc fusion proteins were confirmed according to Example 5 by non-reducing and reducing CE-SDS, and the sequences were further identified by LC-MS with glycan removal according to Example 7. The % homodimer was measured by size-exclusion chromatography according to Example 9. As shown in Table 9, the homodimer titers of the insulin-Fc fusion proteins of SEQ ID NO: 47, SEQ ID NO: 49 and SEQ ID NO: 51 met the design goal for homodimer titer.

Example 26: Screening of Canine Serum Containing Anti-Drug Antibodies and Identification of Potential Immunogenic Epitopes at the B10D and A8H Positions of the Insulin Polypeptide It was hypothesized, therefore, that the insulin polypeptide of SEQ ID NO: 16 may unexpectedly contain specific epitopes (i.e., immunogenic "hot spots") against which the dog's immune system is directed. Therefore, the binding specificity of the antibodies present in the serum samples described in Example 17 were evaluated according to the general procedure of Example 18. The analysis of the antibody-containing serum samples from the repeated dosing of the insulin-Fc fusion protein of SEQ ID NO: 41 (Example 24) against the coated insulin-Fc fusion protein library demonstrated that there were unexpectedly two primary "hot spots" present within the insulin polypeptide sequence of SEQ ID NO: 16: the aspartic acid mutation at the 10th position from the N-terminus of the B-chain (i.e., B10), and, separately, the histidine mutation at the 8th position from the N-terminal end of the A-chain (i.e., A8). The results suggest that insulin-Fc fusion proteins comprising insulin polypeptide amino acid compositions containing these two particular amino acid mutations are likely to be immunogenic in dogs and therefore likely to give rise to anti-drug antibodies that neutralize the bioactivity after repeated injections. The insulin-Fc fusion protein configurations of SEQ ID NO: 47 and SEQ ID NO: 51 however met the design requirements for IR binding IC50, while the insulin-Fc fusion protein configuration of SEQ ID NO: 49 (where the B10D and A8H mutations were restored to the native B10H and A8T) demonstrated an IR binding IC50 or >5000 nM, indicating that this insulin-Fc fusion protein configuration was highly unlikely to be bioactive in vivo. This indicated that the B10H and A8T mutations in these insulin-Fc fusion protein configurations appeared to be necessary to achieve in vivo bioactivity.

TABLE 9

Homodimer titers and IR binding for insulin-Fc fusion protein configurations utilizing canine IgGB Fc with cNg mutations

| SEQ ID NO: | cNg MUTATION | Protein Yield (mg/L) | % Homo-dimer | Homodimer Titer (mg/L) | IR Binding, IC50 (nM) |
|---|---|---|---|---|---|
| SEQ ID NO: 47 | S | 76.7 | 98.3% | 75.4 | 145 |
| SEQ ID NO: 49 | Q | 21.4 | 98.7% | 21.1 | >5000 |
| SEQ ID NO: 51 | K | 45.4 | 98.1% | 44.5 | 147 |

Figure 9:
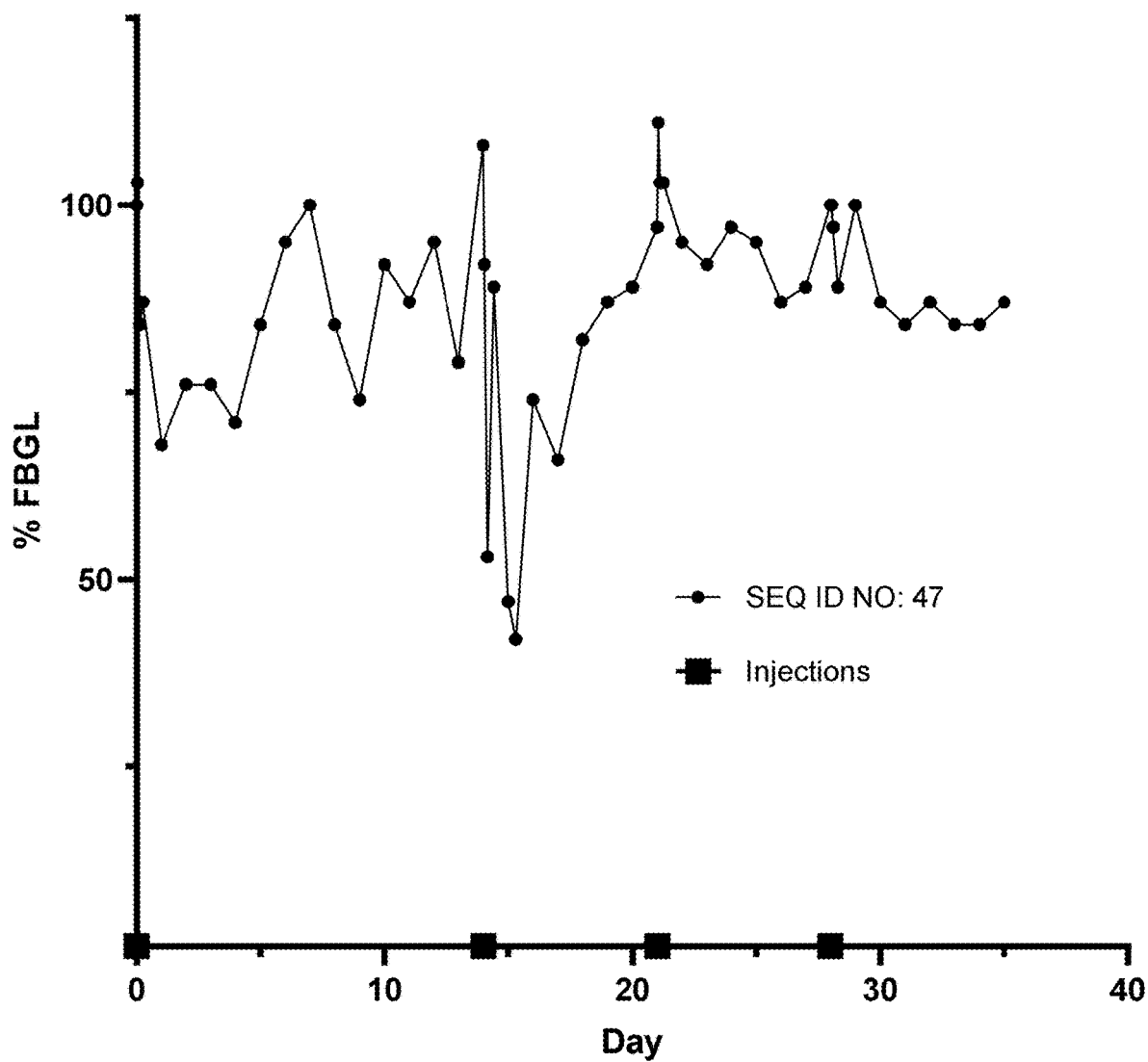
FIG. 9 shows % fasting blood glucose levels from Day 0 to Day 40 for N=1 dog dosed subcutaneously on Day 0, Day 7, Day 14 and Day 21 with the homodimer of SEQ ID NO: 47.

Example 27: Evaluation of In Vivo Bioactivity and Immunogenicity of Non-Glycosylated Insulin-Fc Fusion Protein Configurations of with cNg Mutations of the Canine IgGB Isotype Fc Fragment To determine if the insulin-Fc fusion protein of SEQ ID NO: 47, containing the cNg-S mutation, improved the repeated dose bioactivity performance in dogs, the compound was administered subcutaneously to N=1 dog on day 0, day 14, day 21 and on day 28 according to the procedure of Example 15. The % FBGL across these doses for SEQ ID NO: 47 is illustrated in FIG. 9. When the dog's % FBGL dropped too low, the dog was given food to raise the blood glucose to a safe level. The NAOC for the first injection measured over the first 7 days following the injection was 403% FBGL·days·kg/mg, showing that the insulin-Fc fusion protein of SEQ ID NO: 47 was satisfactorily bioactive in vivo. The NAOC and NAOCR were also measured for each subsequent dose according to the general procedure of Example 15, calculated from the time the dose was administered until just before the next dose was administered. The NAOC and the NAOCR shown in Table 10 illustrate that the insulin-Fc fusion protein of SEQ ID NO: 47 exhibited an NAOCR that decreased significantly on doses 2 and 3 of a three dose regimen. Therefore, the insulin-Fc fusion protein of SEQ ID NO: 47, containing the cNg-S mutation, was unable to demonstrate repeated dose bioactivity in dogs.

TABLE 10

NAOC per dose for repeated doses of SEQ ID NO: 47

| Injection Number of SEQ ID NO: 47 | NAOC (% FBGL · days · kg/mg) | NAOCR |
|---|---|---|
| 1 | 403 | 1.0 |
| 2 | 508 | 0.3 |
| 3 | 128 | 0.32 |

To determine if the insulin-Fc fusion protein of SEQ ID NO: 49, containing the cNg-Q mutation, improved the repeated dose bioactivity performance in dogs, the compound was administered subcutaneously to N=1 dog on day 0 and on day 28 according to the procedure of Example 15. The % FBGL across these doses for SEQ ID NO: 49 is illustrated in FIG. 9. When the dog's % FBGL dropped too low, the dog was given food to raise the blood glucose to a safe level. The NAOC for the first injection measured over the first 7 days following the injection was 24.2% FBGL·days·kg/mg, showing that the insulin-Fc fusion protein of SEQ ID NO: 49 did not show satisfactory bioactive in vivo. The NAOC and NAOCR were also measured for the subsequent dose according to the general procedure of Example 15, calculated from the time the dose was administered until just before the next dose was administered. The NAOC and the NAOCR shown in Table 11 illustrate that the insulin-Fc fusion protein of SEQ ID NO: 49 exhibited 0 NAOC and NAOCR for the second dose. Therefore, the insulin-Fc fusion protein of SEQ ID NO: 49, containing the cNg-S mutation, was unable to demonstrate repeated dose bioactivity in dogs.

TABLE 11

NAOC per dose for repeated doses of SEQ ID NO: 49

| Injection Number of SEQ ID NO: 49 | NAOC (% FBGL · days · kg/mg) | NAOCR |
|---|---|---|
| 1 | 403 | 1.0 |
| 2 | 0 | 0.0 |

Figure 10:
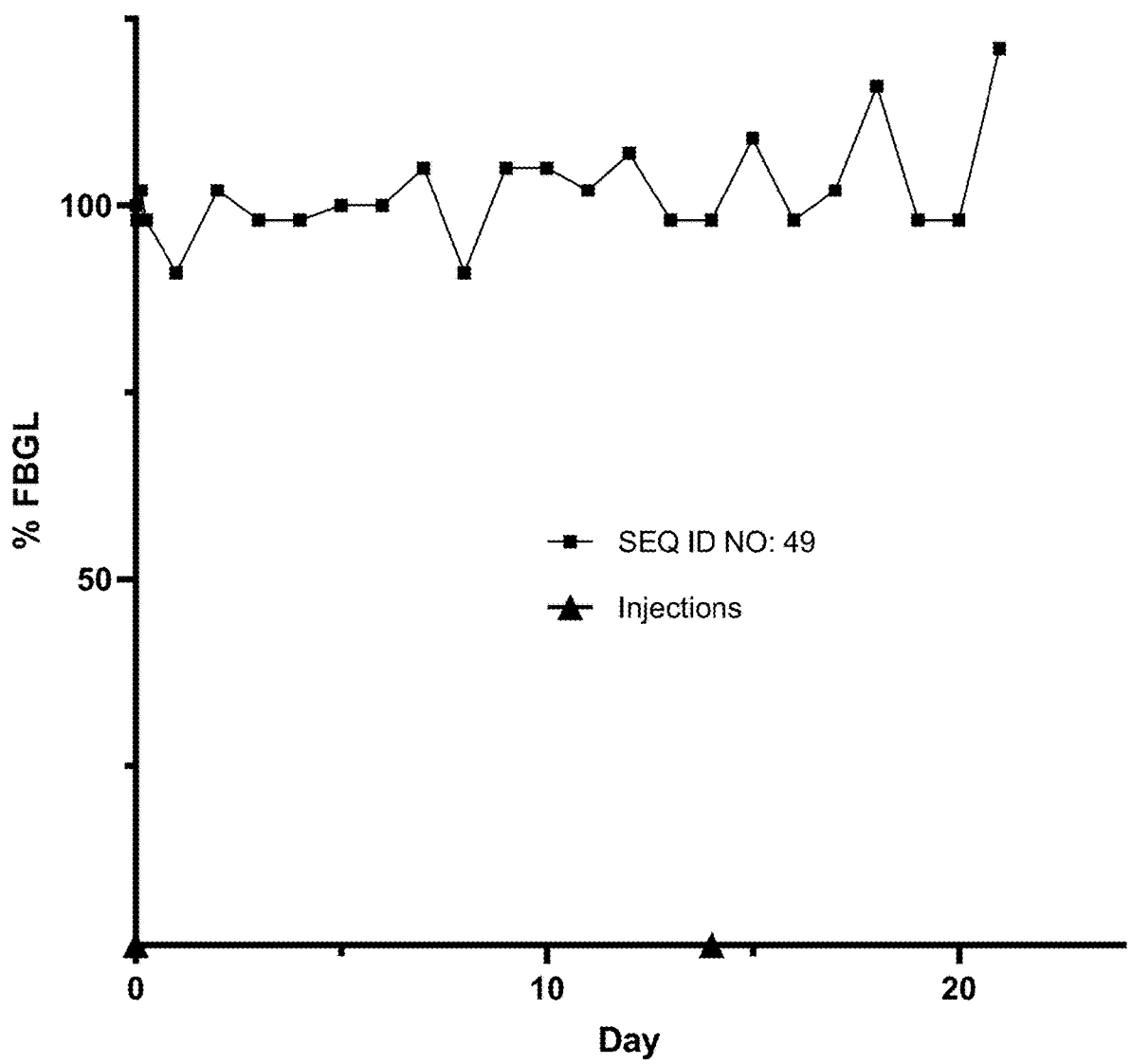
FIG. 10 shows % fasting blood glucose levels from Day 0 to Day 35 for N=1 dog dosed subcutaneously on Day 0, Day 7, Day 14 and Day 21 with the homodimer of SEQ ID NO: 49.
Figure 11:
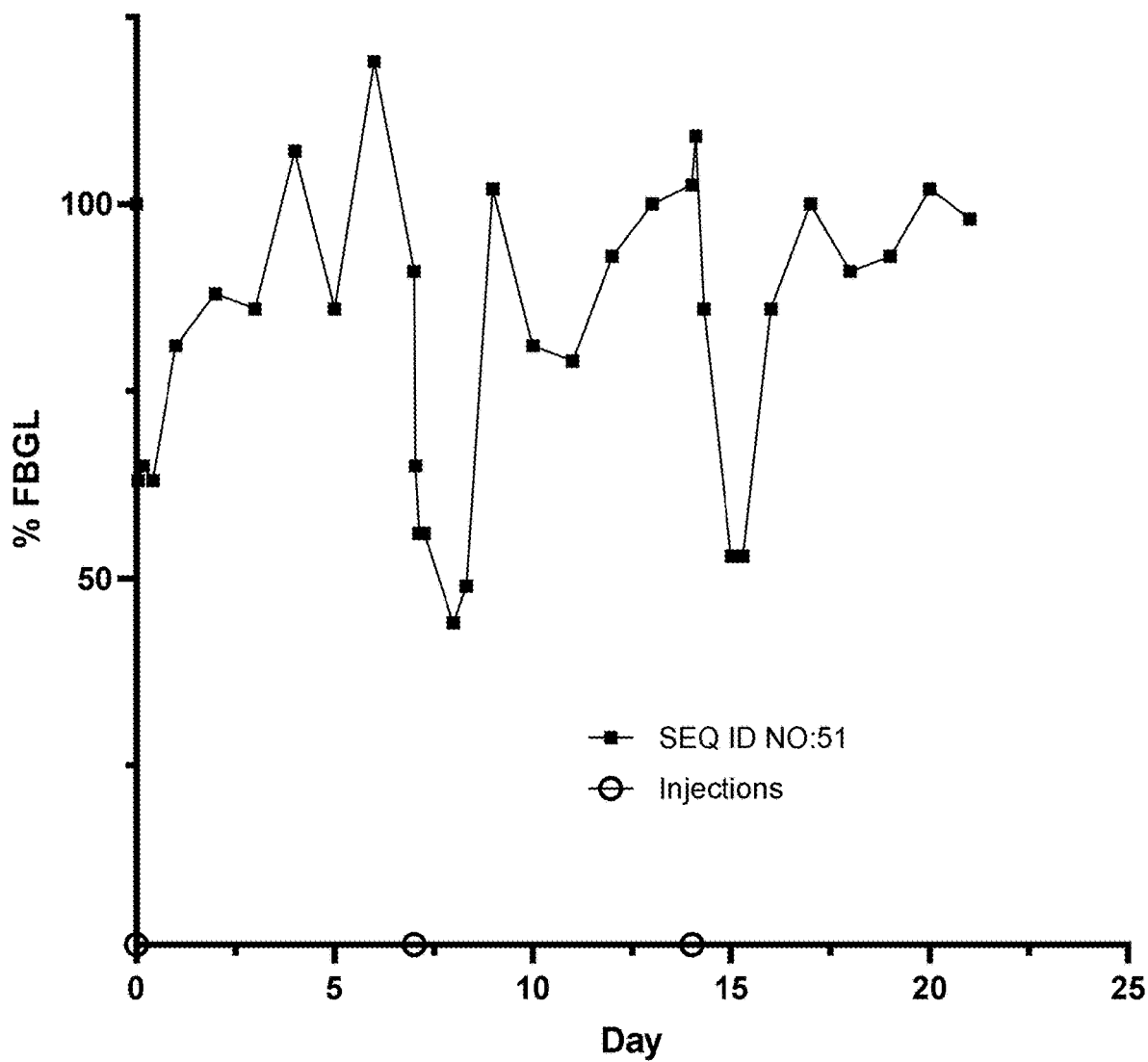
FIG. 11 shows % fasting blood glucose levels from Day 0 to Day 40 for N=1 dog dosed subcutaneously on Day 0, Day 7, Day 14 and Day 21 with the homodimer of SEQ ID NO: 51.

To determine if the insulin-Fc fusion protein of SEQ ID NO: 51, containing the cNg-K mutation together with the des hinge D omission (the Fc fragment of SEQ ID NO: 32) improved the repeated dose bioactivity performance in dogs, the compound was administered subcutaneously to N=1 dog on day 0, day 7, and day 14 according to the procedure of Example 15. The % FBGL across these doses for SEQ ID NO: 51 is illustrated in FIG. 10. When the dog's % FBGL dropped too low, the dog was given food to raise the blood glucose to a safe level. The NAOC for the first injection was 178% FBGL·days·kg/mg, showing that the insulin-Fc fusion protein of SEQ ID NO: 51 was satisfactorily bioactive in vivo. The NAOC and NAOCR were also measured for each subsequent dose according to the general procedure of Example 15, calculated from the time the dose was administered until just before the next dose was administered. The NAOC and the NAOCR shown in Table 12 illustrate that the insulin-Fc fusion protein configuration of SEQ ID NO: 51 maintains an NAOCR greater than 0.6 throughout the three doses. Therefore, unexpectedly, the insulin-Fc fusion protein of SEQ ID NO: 51, containing the cNg-K mutation with des hinge D, was the only non-glycosylated mutant of the insulin-Fc fusion protein of SEQ ID NO: 41 resulting in significantly improved repeated dose bioactivity in dogs.

TABLE 12

NAOC per dose for repeated doses of SEQ ID NO: 51

| Injection Number of SEQ ID NO: 51 | NAOC (% FBGL · days · kg/mg) | NAOCR |
|---|---|---|
| 1 | 178 | 1.0 |
| 2 | 382 | 2.2 |
| 3 | 238 | 1.3 |

Example 28: Evaluation of In Vivo Bioactivity and Immunogenicity of the Insulin-Fc Fusion Protein Configurations with the Fc Fragment of SEQ ID NO: 32

Based on the results from Example 27, insulin-Fc fusion protein configurations with the Fc fragment of SEQ ID NO: 32 and insulin polypeptide combinations based on the B-Chain, C-Chain and A-Chain sequences of Table 1 are evaluated for in vivo bioactivity and immunogenicity.

The insulin-Fc fusion protein configurations comprising insulin polypeptide combinations of Table 1 are manufactured in HEK293 cells according to Example 2 and purified using a Protein A column according to Example 4. The structures are confirmed according to Example 6 by non-reducing and reducing CE-SDS, and the sequences are further identified by LC-MS with glycan removal according to Example 8. The % homodimers are measured by size-exclusion chromatography according to Example 10. The in vivo bioactivity after a single dose of the insulin-Fc fusion protein configuration being tested is measured according to Example 14 and the in vivo bioactivity is measured after repeated doses according to Example 16.

It is expected that the insulin-Fc fusion protein configurations with the Fc fragment of SEQ ID NO: 32 and insulin polypeptide combinations based on the B-Chain, C-Chain and A-Chain sequences of Table 1 will exhibit acceptable homodimer titer and sustained bioactivity in vivo after repeated doses. That is, the NAOC and the NAOCR for each of the insulin-Fc fusion protein configurations based on the B-Chain, C-Chain and A-Chain sequences of Table 1 maintain an NAOCR greater than 0.6 over at least three doses.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising,"

"contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

We claim:

1. A fusion protein comprising an insulin polypeptide and an Fc fragment, wherein the insulin polypeptide and the Fc fragment are connected by a peptide linker, wherein the Fc fragment comprises the following sequence:

(SEQ ID NO: 32)
CPKCPAPEMLGGPSVFIFPPKPKDTLLIARTPEVTCVVVDLDPEDPEV

QISWFVDGKQMQTAKTQPREEQFKGTYRVVSVLPIGHQDWLKGKQFTC

KVNNKALPSPIERTISKARGQAHQPSVYVLPPSREELSKNTVSLTCLI

KDFFPPDIDVEWQSNGQQEPESKYRTTPPQLDEDGSYFLYSKLSVDKS

RWQRGDTFICAVMHEALHNHYTQESLSHSPG and wherein the insulin polypeptide comprises the following sequence:

(SEQ ID NO: 16)
FVNQHLCGSDLVEALALVCGERGFFYTDPTGGGPRRGIVEQCCHSI

CSLYQLENYCN.

2. The fusion protein of claim 1, comprising domains in the following orientation from N- to C-terminus: (N-terminus)-insulin polypeptide-linker-Fc fragment-(C-terminus).

3. The fusion protein of claim 1, wherein the insulin polypeptide and the Fc fragment are connected by a peptide linker comprising the following sequence:
GGGGAGGGG (SEQ ID NO: 25).

4. The fusion protein of claim 1, wherein the fusion protein is a homodimer.

5. The fusion protein of claim 4, wherein the percentage homodimer of the fusion protein is greater than 90%.

6. The fusion protein of claim 5, wherein the fusion protein is made using one of HEK293 or CHO cells, and the resulting homodimer titer after purification using Protein A beads or a Protein A column is greater than 40 mg/L.

7. The fusion protein of claim 1, wherein the insulin receptor IC50 for the fusion protein is less than or equal to 5000 nM.

8. The fusion protein of claim 1, wherein the serum half-life of the fusion protein in the blood or serum of a target animal upon administration is longer than about 3 days.

9. The fusion protein of claim 8, wherein the time during which there is a statistically significant decrease in blood glucose level in the target animal relative to a pre-dose level is longer than one of 2 hours, 6 hours, 9 hours, 12 hours, 18 hours, 1 day, 1.5 days, 2 days, 2.5 days, 3 days, 4 days, 5 days, 6 days, 7 days, or longer.

10. The fusion protein of claim 8, wherein the Normalized Area Over the Curve (NAOC) after a first subcutaneous injection is greater than 150% Fasting Blood Glucose Level (FBGL)·days·kg/mg.

11. The fusion protein of claim 10, wherein the ratio of the NAOC after the third weekly subcutaneous injection of the fusion protein in a target animal that is a dog to the NAOC after the first subcutaneous injection of the fusion protein in the dog is greater than 0.50.

12. The fusion protein of claim 1, wherein the fusion protein is formulated as a pharmaceutical composition.

13. The pharmaceutical composition of claim 12, wherein the fusion protein is present in the pharmaceutical composition at a concentration of about 3 mg/mL or greater.

14. The pharmaceutical composition of claim 13, wherein the composition is suitable for subcutaneous administration.

15. A method for lowering the blood glucose level of a target animal, the method comprising administering a physiologically effective amount of the fusion protein of claim 1 or a pharmaceutical composition thereof to the target animal.

16. The method of claim 15, wherein the target animal is a dog diagnosed with diabetes.

17. The method of claim 15, wherein the fusion protein is administered subcutaneously.

18. The method of claim 15, wherein the fusion protein is administered daily, twice weekly, or once weekly to the target animal.

19. The method of claim 15, wherein the fusion protein is administered once weekly to the target animal at a dose between 0.025 and 0.5 mg/kg/week.

20. A fusion protein comprising an inulin polypeptide linked to an Fc fragment, wherein the fusion protein comprises the following sequence:

```
(SEQ ID NO: 51)
FVNQHLCGSDLVEALALVCGERGFFYTDPTGGGPRRGIVEQCCHSICS

LYQLENYCNGGGGAGGGGCPKCPAPEMLGGPSVFIFPPKPKDTLLIAR

TPEVTCVVVDLDPEDPEVQISWFVDGKQMQTAKTQPREEQFKGTYRVV

SVLPIGHQDWLKGKQFTCKVNNKALPSPIERTISKARGQAHQPSVYVL

PPSREELSKNTVSLTCLIKDFFPPDIDVEWQSNGQQEPESKYRTTPPQ

LDEDGSYFLYSKLSVDKSRWQRGDTFICAVMHEALHNHYTQESLS

HSPG.
```

* * * * *

```
                              SEQUENCE LISTING

<160> NUMBER OF SEQ ID NOS: 54

<210> SEQ ID NO 1
<211> LENGTH: 30
<212> TYPE: PRT
<213> ORGANISM: Artificial Sequence
<220> FEATURE:
<223> OTHER INFORMATION: Human Insulin B-Chain

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 2
<211> LENGTH: 21
<212> TYPE: PRT
<213> ORGANISM: Artificial Sequence
<220> FEATURE:
<223> OTHER INFORMATION: Human Insulin A-Chain

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 86
<212> TYPE: PRT
<213> ORGANISM: Artificial Sequence
<220> FEATURE:
<223> OTHER INFORMATION: Human ProInsulin

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 4
<211> LENGTH: 30
<212> TYPE: PRT
<213> ORGANISM: Artificial Sequence
<220> FEATURE:
<223> OTHER INFORMATION: Insulin B-chain Analog

<400> SEQUENCE: 4
```

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Insulin B-chain Analog

<400> SEQUENCE: 5

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Insulin B-chain Analog
<220> FEATURE:
<221> NAME/KEY: XaaXaa
<222> LOCATION: (28)..(29)
<223> OTHER INFORMATION: XaaXaa is PR, PE, PA, DP, EP, AP, DK, EK, ER,
      AK, or AR

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Pro Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Insulin B-chain Analog

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 8
<211> LENGTH: 6
<212> TYPE: PRT
<213> ORGANISM: Artificial Sequence
<220> FEATURE:
<223> OTHER INFORMATION: C-Chain

<400> SEQUENCE: 8

Gly Gly Gly Pro Arg Arg
1               5

<210> SEQ ID NO 9
<211> LENGTH: 9
<212> TYPE: PRT
<213> ORGANISM: Artificial Sequence
<220> FEATURE:
<223> OTHER INFORMATION: C-Chain Consensus 1
```

```
<220> FEATURE:
<221> NAME/KEY: Xaa
<222> LOCATION: (1)..(1)
<223> OTHER INFORMATION: Xaa is E or absent
<220> FEATURE:
<221> NAME/KEY: Xaa
<222> LOCATION: (2)..(2)
<223> OTHER INFORMATION: Xaa is E or absent
<220> FEATURE:
<221> NAME/KEY: Xaa
<222> LOCATION: (3)..(3)
<223> OTHER INFORMATION: Xaa is E, G or absent
<220> FEATURE:
<221> NAME/KEY: Xaa
<222> LOCATION: (4)..(4)
<223> OTHER INFORMATION: Xaa is G, E, A, or absent
<220> FEATURE:
<221> NAME/KEY: Xaa
<222> LOCATION: (5)..(5)
<223> OTHER INFORMATION: Xaa is G, E, A, F, or D
<220> FEATURE:
<221> NAME/KEY: Xaa
<222> LOCATION: (6)..(6)
<223> OTHER INFORMATION: Xaa is G, E, or A
<220> FEATURE:
<221> NAME/KEY: Xaa
<222> LOCATION: (7)..(7)
<223> OTHER INFORMATION: Xaa is P or A

<400> SEQUENCE: 9

Xaa Xaa Xaa Xaa Xaa Xaa Xaa Arg Arg
1               5

<210> SEQ ID NO 10
<211> LENGTH: 6
<212> TYPE: PRT
<213> ORGANISM: Artificial Sequence
<220> FEATURE:
<223> OTHER INFORMATION: C-Chain Consensus 2
<220> FEATURE:
<221> NAME/KEY: Xaa
<222> LOCATION: (2)..(2)
<223> OTHER INFORMATION: Xaa is E or A
<220> FEATURE:
<221> NAME/KEY: Xaa
<222> LOCATION: (3)..(3)
<223> OTHER INFORMATION: Xaa is G or A
<220> FEATURE:
<221> NAME/KEY: Xaa
<222> LOCATION: (4)..(4)
<223> OTHER INFORMATION: Xaa is A or P
<220> FEATURE:
<221> NAME/KEY: Xaa
<222> LOCATION: (5)..(5)
<223> OTHER INFORMATION: Xaa is A or R

<400> SEQUENCE: 10

Glu Xaa Xaa Xaa Xaa Ala
1               5

<210> SEQ ID NO 11
<211> LENGTH: 5
<212> TYPE: PRT
<213> ORGANISM: Artificial Sequence
<220> FEATURE:
<223> OTHER INFORMATION: C-Chain Consensus 3
<220> FEATURE:
<221> NAME/KEY: Xaa
<222> LOCATION: (1)..(1)
<223> OTHER INFORMATION: Xaa is E or absent
<220> FEATURE:
<221> NAME/KEY: Xaa
<222> LOCATION: (2)..(2)
<223> OTHER INFORMATION: Xaa is E or A
```

```
<400> SEQUENCE: 11

Xaa Xaa Gly Pro Arg
1               5

<210> SEQ ID NO 12
<211> LENGTH: 6
<212> TYPE: PRT
<213> ORGANISM: Artificial Sequence
<220> FEATURE:
<223> OTHER INFORMATION: C-Chain Consensus 4
<220> FEATURE:
<221> NAME/KEY: Xaa
<222> LOCATION: (1)..(1)
<223> OTHER INFORMATION: Xaa is E or absent
<220> FEATURE:
<221> NAME/KEY: Xaa
<222> LOCATION: (4)..(4)
<223> OTHER INFORMATION: Xaa A or P
<220> FEATURE:
<221> NAME/KEY: Xaa
<222> LOCATION: (5)..(5)
<223> OTHER INFORMATION: Xaa is A or R
<220> FEATURE:
<221> NAME/KEY: Xaa
<222> LOCATION: (6)..(6)
<223> OTHER INFORMATION: Xaa is A or R

<400> SEQUENCE: 12

Xaa Glu Gly Xaa Xaa Xaa
1               5

<210> SEQ ID NO 13
<211> LENGTH: 21
<212> TYPE: PRT
<213> ORGANISM: Artificial Sequence
<220> FEATURE:
<223> OTHER INFORMATION: Insulin A-chain Analog
<220> FEATURE:
<221> NAME/KEY: Xaa
<222> LOCATION: (8)..(8)
<223> OTHER INFORMATION: Xaa is T, H, S, E or A
<220> FEATURE:
<221> NAME/KEY: Xaa
<222> LOCATION: (14)..(14)
<223> OTHER INFORMATION: Xaa is any amino acid other than P

<400> SEQUENCE: 13

Gly Ile Val Glu Gln Cys Cys Xaa Ser Ile Cys Ser Leu Xaa Gln Leu
1               5                   10                  15

Glu Asn Tyr Cys Asn
            20

<210> SEQ ID NO 14
<211> LENGTH: 21
<212> TYPE: PRT
<213> ORGANISM: Artificial Sequence
<220> FEATURE:
<223> OTHER INFORMATION: Insulin A-chain Analog

<400> SEQUENCE: 14

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 15
<211> LENGTH: 57
<212> TYPE: PRT
<213> ORGANISM: Artificial Sequence
```

<220> FEATURE:
<223> OTHER INFORMATION: Insulin Polypeptide

<400> SEQUENCE: 15

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55

<210> SEQ ID NO 16
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 16

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55

<210> SEQ ID NO 17
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
    50                  55

<210> SEQ ID NO 18
<211> LENGTH: 58
<212> TYPE: PRT
<213> ORGANISM: Artificial Sequence
<220> FEATURE:
<223> OTHER INFORMATION: Insulin Polypeptide

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Ala Pro Arg Arg Gly Ile Val Glu Gln Cys Cys His Ser Ile Cys
        35                  40                  45

Ser Leu Glu Gln Leu Glu Asn Tyr Cys Asn
    50                  55

<210> SEQ ID NO 19
<211> LENGTH: 59
<212> TYPE: PRT
<213> ORGANISM: Artificial Sequence
<220> FEATURE:
<223> OTHER INFORMATION: Insulin Polypeptide

<400> SEQUENCE: 19

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Ala Ala Pro Arg Arg Gly Ile Val Glu Gln Cys Cys His Ser Ile
        35                  40                  45

Cys Ser Leu Glu Gln Leu Glu Asn Tyr Cys Asn
    50                  55

<210> SEQ ID NO 20
<211> LENGTH: 60
<212> TYPE: PRT
<213> ORGANISM: Artificial Sequence
<220> FEATURE:
<223> OTHER INFORMATION: Insulin Polypeptide

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Ala Ala Ala Pro Arg Arg Gly Ile Val Glu Gln Cys Cys His Ser
        35                  40                  45

Ile Cys Ser Leu Glu Gln Leu Glu Asn Tyr Cys Asn
    50                  55                  60

<210> SEQ ID NO 21
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 21

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Insulin Polypeptide

<400> SEQUENCE: 22

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Ala
            20                  25                  30

Ala Ala Ala Lys Gly Ile Val Glu Gln Cys Cys Thr Ser Ile Cys
        35                  40                  45

Ser Leu Tyr Gln Leu Glu Asn Tyr Cys Asn
    50                  55
```

<210> SEQ ID NO 23
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 23

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn
    50                  55
```

<210> SEQ ID NO 24
<211> LENGTH: 57
<212> TYPE: PRT
<213> ORGANISM: Artificial Sequence
<220> FEATURE:
<223> OTHER INFORMATION: Insulin Polypeptide

<400> SEQUENCE: 24

```
Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn
    50                  55
```

<210> SEQ ID NO 25
<211> LENGTH: 9
<212> TYPE: PRT
<213> ORGANISM: Artificial Sequence
<220> FEATURE:
<223> OTHER INFORMATION: Linker

<400> SEQUENCE: 25

```
Gly Gly Gly Gly Ala Gly Gly Gly Gly
1               5
```

<210> SEQ ID NO 26
<211> LENGTH: 9
<212> TYPE: PRT
<213> ORGANISM: Artificial Sequence
<220> FEATURE:
<223> OTHER INFORMATION: Linker

<400> SEQUENCE: 26

Gly Gly Gly Gly Ser Gly Gly Gly Gly
1               5

<210> SEQ ID NO 27
<211> LENGTH: 21
<212> TYPE: PRT
<213> ORGANISM: Artificial Sequence
<220> FEATURE:
<223> OTHER INFORMATION: Linker

<400> SEQUENCE: 27

Gly Gly Gly Gly Gly Gln Gly Gly Gly Gln Gly Gly Gly Gln
1               5                   10                  15

Gly Gly Gly Gly Gly
            20

<210> SEQ ID NO 28
<211> LENGTH: 228
<212> TYPE: PRT
<213> ORGANISM: Artificial Sequence
<220> FEATURE:
<223> OTHER INFORMATION: FC Fragment

<400> SEQUENCE: 28

Arg Cys Thr Asp Thr Pro Pro Cys Pro Val Pro Glu Pro Leu Gly Gly
1               5                   10                  15

Pro Ser Val Leu Ile Phe Pro Pro Lys Pro Lys Asp Ile Leu Arg Ile
                20                  25                  30

Thr Arg Thr Pro Glu Val Thr Cys Val Val Leu Asp Leu Gly Arg Glu
            35                  40                  45

Asp Pro Glu Val Gln Ile Ser Trp Phe Val Asp Gly Lys Glu Val His
        50                  55                  60

Thr Ala Lys Thr Gln Ser Arg Glu Gln Gln Phe Asn Gly Thr Tyr Arg
65                  70                  75                  80

Val Val Ser Val Leu Pro Ile Glu His Gln Asp Trp Leu Thr Gly Lys
                85                  90                  95

Glu Phe Lys Cys Arg Val Asn His Ile Asp Leu Pro Ser Pro Ile Glu
                100                 105                 110

Arg Thr Ile Ser Lys Ala Arg Gly Arg Ala His Lys Pro Ser Val Tyr
            115                 120                 125

Val Leu Pro Pro Ser Pro Lys Glu Leu Ser Ser Ser Asp Thr Val Ser
        130                 135                 140

Ile Thr Cys Leu Ile Lys Asp Phe Tyr Pro Pro Asp Ile Asp Val Glu
145                 150                 155                 160

Trp Gln Ser Asn Gly Gln Gln Glu Pro Glu Arg Lys His Arg Met Thr
                165                 170                 175

Pro Pro Gln Leu Asp Glu Asp Gly Ser Tyr Phe Leu Tyr Ser Lys Leu
            180                 185                 190

Ser Val Asp Lys Ser Arg Trp Gln Gln Gly Asp Pro Phe Thr Cys Ala
        195                 200                 205

Val Met His Glu Thr Leu Gln Asn His Tyr Thr Asp Leu Ser Leu Ser
    210                 215                 220

His Ser Pro Gly
225

<210> SEQ ID NO 29
<211> LENGTH: 224
<212> TYPE: PRT

<213> ORGANISM: Artificial Sequence
<220> FEATURE:
<223> OTHER INFORMATION: FC Fragment

<400> SEQUENCE: 29

```
Asp Cys Pro Lys Cys Pro Ala Pro Glu Met Leu Gly Gly Pro Ser Val
1               5                   10                  15

Phe Ile Phe Pro Pro Lys Pro Lys Asp Thr Leu Leu Ile Ala Arg Thr
                20                  25                  30

Pro Glu Val Thr Cys Val Val Asp Leu Asp Pro Glu Asp Pro Glu
            35                  40                  45

Val Gln Ile Ser Trp Phe Val Asp Gly Lys Gln Met Gln Thr Ala Lys
    50                  55                  60

Thr Gln Pro Arg Glu Glu Gln Phe Asn Gly Thr Tyr Arg Val Val Ser
65              70                  75                  80

Val Leu Pro Ile Gly His Gln Asp Trp Leu Lys Gly Lys Gln Phe Thr
                85                  90                  95

Cys Lys Val Asn Asn Lys Ala Leu Pro Ser Pro Ile Glu Arg Thr Ile
            100                 105                 110

Ser Lys Ala Arg Gly Gln Ala His Gln Pro Ser Val Tyr Val Leu Pro
        115                 120                 125

Pro Ser Arg Glu Glu Leu Ser Lys Asn Thr Val Ser Leu Thr Cys Leu
    130                 135                 140

Ile Lys Asp Phe Phe Pro Pro Asp Ile Asp Val Glu Trp Gln Ser Asn
145                 150                 155                 160

Gly Gln Gln Glu Pro Glu Ser Lys Tyr Arg Thr Thr Pro Pro Gln Leu
                165                 170                 175

Asp Glu Asp Gly Ser Tyr Phe Leu Tyr Ser Lys Leu Ser Val Asp Lys
            180                 185                 190

Ser Arg Trp Gln Arg Gly Asp Thr Phe Ile Cys Ala Val Met His Glu
        195                 200                 205

Ala Leu His Asn His Tyr Thr Gln Glu Ser Leu Ser His Ser Pro Gly
    210                 215                 220
```

<210> SEQ ID NO 30
<211> LENGTH: 225
<212> TYPE: PRT
<213> ORGANISM: Artificial Sequence
<220> FEATURE:
<223> OTHER INFORMATION: FC Fragment

<400> SEQUENCE: 30

```
Cys Asn Asn Cys Pro Cys Pro Gly Cys Gly Leu Leu Gly Gly Pro Ser
1               5                   10                  15

Val Phe Ile Phe Pro Pro Lys Pro Lys Asp Ile Leu Val Thr Ala Arg
                20                  25                  30

Thr Pro Thr Val Thr Cys Val Val Asp Leu Asp Pro Glu Asn Pro
            35                  40                  45

Glu Val Gln Ile Ser Trp Phe Val Asp Ser Lys Gln Val Gln Thr Ala
    50                  55                  60

Asn Thr Gln Pro Arg Glu Glu Gln Ser Asn Gly Thr Tyr Arg Val Val
65              70                  75                  80

Ser Val Leu Pro Ile Gly His Gln Asp Trp Leu Ser Gly Lys Gln Phe
                85                  90                  95

Lys Cys Lys Val Asn Asn Lys Ala Leu Pro Ser Pro Ile Glu Glu Ile
            100                 105                 110
```

```
Ile Ser Lys Thr Pro Gly Gln Ala His Gln Pro Asn Val Tyr Val Leu
        115                 120                 125

Pro Pro Ser Arg Asp Glu Met Ser Lys Asn Thr Val Thr Leu Thr Cys
130                 135                 140

Leu Val Lys Asp Phe Phe Pro Glu Ile Asp Val Glu Trp Gln Ser
145                 150                 155                 160

Asn Gly Gln Gln Glu Pro Glu Ser Lys Tyr Arg Met Thr Pro Pro Gln
                165                 170                 175

Leu Asp Glu Asp Gly Ser Tyr Phe Leu Tyr Ser Lys Leu Ser Val Asp
                180                 185                 190

Lys Ser Arg Trp Gln Arg Gly Asp Thr Phe Ile Cys Ala Val Met His
                195                 200                 205

Glu Ala Leu His Asn His Tyr Thr Gln Ile Ser Leu Ser His Ser Pro
        210                 215                 220

Gly
225

<210> SEQ ID NO 31
<211> LENGTH: 225
<212> TYPE: PRT
<213> ORGANISM: Artificial Sequence
<220> FEATURE:
<223> OTHER INFORMATION: FC Fragment

<400> SEQUENCE: 31

Cys Ile Ser Pro Cys Pro Val Pro Glu Ser Leu Gly Gly Pro Ser Val
1               5                   10                  15

Phe Ile Phe Pro Pro Lys Pro Lys Asp Ile Leu Arg Ile Thr Arg Thr
                20                  25                  30

Pro Glu Ile Thr Cys Val Val Leu Asp Leu Gly Arg Glu Asp Pro Glu
            35                  40                  45

Val Gln Ile Ser Trp Phe Val Asp Gly Lys Glu Val His Thr Ala Lys
    50                  55                  60

Thr Gln Pro Arg Glu Gln Gln Phe Asn Ser Thr Tyr Arg Val Val Ser
65                  70                  75                  80

Val Leu Pro Ile Glu His Gln Asp Trp Leu Thr Gly Lys Glu Phe Lys
                85                  90                  95

Cys Arg Val Asn His Ile Gly Leu Pro Ser Pro Ile Glu Arg Thr Ile
            100                 105                 110

Ser Lys Ala Arg Gly Gln Ala His Gln Pro Ser Val Tyr Val Leu Pro
    115                 120                 125

Pro Ser Pro Lys Glu Leu Ser Ser Ser Asp Thr Val Thr Leu Thr Cys
130                 135                 140

Leu Ile Lys Asp Phe Phe Pro Glu Ile Asp Val Glu Trp Gln Ser
145                 150                 155                 160

Asn Gly Gln Pro Glu Pro Glu Ser Lys Tyr His Thr Thr Ala Pro Gln
                165                 170                 175

Leu Asp Glu Asp Gly Ser Tyr Phe Leu Tyr Ser Lys Leu Ser Val Asp
                180                 185                 190

Lys Ser Arg Trp Gln Gln Gly Asp Thr Phe Thr Cys Ala Val Met His
                195                 200                 205

Glu Ala Leu Gln Asn His Tyr Thr Asp Leu Ser Leu Ser His Ser Pro
        210                 215                 220

Gly
225
```

<210> SEQ ID NO 32
<211> LENGTH: 223
<212> TYPE: PRT
<213> ORGANISM: Artificial Sequence
<220> FEATURE:
<223> OTHER INFORMATION: FC Fragment

<400> SEQUENCE: 32

Cys Pro Lys Cys Pro Ala Pro Glu Met Leu Gly Gly Pro Ser Val Phe
1               5                   10                  15

Ile Phe Pro Pro Lys Pro Lys Asp Thr Leu Leu Ile Ala Arg Thr Pro
            20                  25                  30

Glu Val Thr Cys Val Val Val Asp Leu Asp Pro Glu Asp Pro Glu Val
        35                  40                  45

Gln Ile Ser Trp Phe Val Asp Gly Lys Gln Met Gln Thr Ala Lys Thr
    50                  55                  60

Gln Pro Arg Glu Glu Gln Phe Lys Gly Thr Tyr Arg Val Val Ser Val
65                  70                  75                  80

Leu Pro Ile Gly His Gln Asp Trp Leu Lys Gly Lys Gln Phe Thr Cys
                85                  90                  95

Lys Val Asn Asn Lys Ala Leu Pro Ser Pro Ile Glu Arg Thr Ile Ser
            100                 105                 110

Lys Ala Arg Gly Gln Ala His Gln Pro Ser Val Tyr Val Leu Pro Pro
        115                 120                 125

Ser Arg Glu Glu Leu Ser Lys Asn Thr Val Ser Leu Thr Cys Leu Ile
    130                 135                 140

Lys Asp Phe Phe Pro Pro Asp Ile Asp Val Glu Trp Gln Ser Asn Gly
145                 150                 155                 160

Gln Gln Glu Pro Glu Ser Lys Tyr Arg Thr Thr Pro Pro Gln Leu Asp
                165                 170                 175

Glu Asp Gly Ser Tyr Phe Leu Tyr Ser Lys Leu Ser Val Asp Lys Ser
            180                 185                 190

Arg Trp Gln Arg Gly Asp Thr Phe Ile Cys Ala Val Met His Glu Ala
        195                 200                 205

Leu His Asn His Tyr Thr Gln Glu Ser Leu Ser His Ser Pro Gly
    210                 215                 220

<210> SEQ ID NO 33
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 33

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

```
Arg Ile Thr Arg Thr Pro Glu Val Thr Cys Val Val Leu Asp Leu Gly
            100                 105                 110
Arg Glu Asp Pro Glu Val Gln Ile Ser Trp Phe Val Asp Gly Lys Glu
        115                 120                 125
Val His Thr Ala Lys Thr Gln Ser Arg Glu Gln Gln Phe Asn Gly Thr
    130                 135                 140
Tyr Arg Val Val Ser Val Leu Pro Ile Glu His Gln Asp Trp Leu Thr
145                 150                 155                 160
Gly Lys Glu Phe Lys Cys Arg Val Asn His Ile Asp Leu Pro Ser Pro
                165                 170                 175
Ile Glu Arg Thr Ile Ser Lys Ala Arg Gly Arg Ala His Lys Pro Ser
            180                 185                 190
Val Tyr Val Leu Pro Pro Ser Pro Lys Glu Leu Ser Ser Ser Asp Thr
        195                 200                 205
Val Ser Ile Thr Cys Leu Ile Lys Asp Phe Tyr Pro Pro Asp Ile Asp
    210                 215                 220
Val Glu Trp Gln Ser Asn Gly Gln Gln Glu Pro Glu Arg Lys His Arg
225                 230                 235                 240
Met Thr Pro Pro Gln Leu Asp Glu Asp Gly Ser Tyr Phe Leu Tyr Ser
                245                 250                 255
Lys Leu Ser Val Asp Lys Ser Arg Trp Gln Gln Gly Asp Pro Phe Thr
            260                 265                 270
Cys Ala Val Met His Glu Thr Leu Gln Asn His Tyr Thr Asp Leu Ser
        275                 280                 285
Leu Ser His Ser Pro Gly
    290

<210> SEQ ID NO 34
<211> LENGTH: 942
<212> TYPE: DNA
<213> ORGANISM: Artificial Sequence
<220> FEATURE:
<223> OTHER INFORMATION: cDNA for Insulin-Fc Fusion Protein

<400> SEQUENCE: 34
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggacgctg cactgacacc cctccatgcc ctgtgcccga gcccctgggt     300
ggccccagcg tactgatctt ccaccgaaaa cccaaggaca tcctgaggat cacccgcacc     360
ccggaggtga cctgcgtggt gctggacctg ggcagggagg accccgaagt gcaaatcagc     420
tggttcgtgg acggaaagga ggtgcacacc gccaagaccc aatcaaggga gcagcagttc     480
aacggcacct acagggtggt gagcgtgttg cccatagagc accaggactg gctgaccggc     540
aaggagttca gtgccgcgt gaaccacatt gatctcccca gccccatcga ggactatc      600
tccaaggccc gagggagggc cacaagccc agtgtatacg tgctgccgcc ctctccgaag     660
gaactgagct ctagcgacac cgtgagcatc acctgcctga tcaaggactt ctaccctccc     720
gacatagacg tagagtggca gagcaacggc cagcaggagc ccgaaaggaa gcacaggatg     780
accccacccc aactgacga ggacggctca tactttcttt atagcaagct gagtgtggac     840
aagagcaggt ggcagcaggg cgacccttc acttgcgccg taatgcacga gaccctgcag     900
```
aatcactaca ccgacctgtc actgagccat agccccggat ag                                942

<210> SEQ ID NO 35
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 35

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ser Gly Gly
    50                  55                  60

Gly Gly Arg Cys Thr Asp Thr Pro Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190

Val Tyr Val Leu Pro Pro Ser Pro Lys Glu Leu Ser Ser Ser Asp Thr
        195                 200                 205

Val Ser Ile Thr Cys Leu Ile Lys Asp Phe Tyr Pro Pro Asp Ile Asp
    210                 215                 220

Val Glu Trp Gln Ser Asn Gly Gln Gln Glu Pro Glu Arg Lys His Arg
225                 230                 235                 240

Met Thr Pro Pro Gln Leu Asp Glu Asp Gly Ser Tyr Phe Leu Tyr Ser
                245                 250                 255

Lys Leu Ser Val Asp Lys Ser Arg Trp Gln Gln Gly Asp Pro Phe Thr
            260                 265                 270

Cys Ala Val Met His Glu Thr Leu Gln Asn His Tyr Thr Asp Leu Ser
        275                 280                 285

Leu Ser His Ser Pro Gly
    290

<210> SEQ ID NO 36
<211> LENGTH: 942
<212> TYPE: DNA
<213> ORGANISM: Artificial Sequence
<220> FEATURE:
<223> OTHER INFORMATION: cDNA for Insulin-Fc Fusion Protein

<400> SEQUENCE: 36

```
atggaatgga gctgggtctt tctcttcttc ctgtcagtaa cgactggtgt ccactccttc    60
gtgaaccagc acctgtgcgg ctccgacctg gtggaagctc tgtatctcgt gtgcggcgag   120
cggggcttct tctacaccga tcccactgga ggcggtccac gcagaggcat cgtggaacag   180
tgctgccact ccatctgctc cctgtaccag ctggaaaact actgcaatgg cggaggtggt   240
tcaggaggcg gtggacgctg cactgacacc ctccatgcc ctgtgcccga gcccctgggt   300
ggccccagcg tactgatctt cccaccgaaa cccaaggaca tcctgaggat cacccgcacc   360
ccggaggtga cctgcgtggt gctggacctg gcagggagg accccgaagt gcaaatcagc   420
tggttcgtgg acggaaagga ggtgcacacc gccaagaccc aatcaaggga gcagcagttc   480
aacggcacct acagggtggt gagcgtgttg cccatagagc accaggactg gctgaccggc   540
aaggagttca gtgccgcgt gaaccacatt gatctcccca gccccatcga ggactatc    600 tccaaggccc gagggagggc ccacaagccc agtgtatacg tgctgccgcc ctctccgaag   660
gaactgagct ctagcgacac cgtgagcatc acctgcctga tcaaggactt ctaccctccc   720
gacatagacg tagagtggca gagcaacggc cagcaggagc ccgaaaggaa gcacaggatg   780
accccacccc aactggacga ggacggctca tactttcttt atagcaagct gagtgtggac   840
aagagcaggt ggcagcaggg cgaccctttc acttgcgccg taatgcacga gaccctgcag   900
aatcactaca ccgacctgtc actgagccat agccccggat ag                     942
```

<210> SEQ ID NO 37
<211> LENGTH: 294
<212> TYPE: PRT
<213> ORGANISM: Artificial Sequence
<220> FEATURE:
<223> OTHER INFORMATION: Insulin-Fc Fusion Protein

<400> SEQUENCE: 37

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn Gly Gly Gly Ser Gly Gly
    50                  55                  60

Gly Gly Arg Cys Thr Asp Thr Pro Cys Pro Val Pro Glu Pro Leu
65                  70                  75                  80

Gly Gly Pro Ser Val Leu Ile Phe Pro Pro Lys Pro Lys Asp Ile Leu
                85                  90                  95

Arg Ile Thr Arg Thr Pro Glu Val Thr Cys Val Val Leu Asp Leu Gly
            100                 105                 110

Arg Glu Asp Pro Glu Val Gln Ile Ser Trp Phe Val Asp Gly Lys Glu
        115                 120                 125

Val His Thr Ala Lys Thr Gln Ser Arg Glu Gln Gln Phe Asn Gly Thr
    130                 135                 140

Tyr Arg Val Val Ser Val Leu Pro Ile Glu His Gln Asp Trp Leu Thr
145                 150                 155                 160

Gly Lys Glu Phe Lys Cys Arg Val Asn His Ile Asp Leu Pro Ser Pro
                165                 170                 175

Ile Glu Arg Thr Ile Ser Lys Ala Arg Gly Arg Ala His Lys Pro Ser
            180                 185                 190
```

```
Val Tyr Val Leu Pro Pro Ser Pro Lys Glu Leu Ser Ser Ser Asp Thr
        195                 200                 205
Val Ser Ile Thr Cys Leu Ile Lys Asp Phe Tyr Pro Pro Asp Ile Asp
    210                 215                 220
Val Glu Trp Gln Ser Asn Gly Gln Gln Glu Pro Glu Arg Lys His Arg
225                 230                 235                 240
Met Thr Pro Pro Gln Leu Asp Glu Asp Gly Ser Tyr Phe Leu Tyr Ser
                245                 250                 255
Lys Leu Ser Val Asp Lys Ser Arg Trp Gln Gln Gly Asp Pro Phe Thr
            260                 265                 270
Cys Ala Val Met His Glu Thr Leu Gln Asn His Tyr Thr Asp Leu Ser
        275                 280                 285
Leu Ser His Ser Pro Gly
    290
```

<210> SEQ ID NO 38
<211> LENGTH: 942
<212> TYPE: DNA
<213> ORGANISM: Artificial Sequence
<220> FEATURE:
<223> OTHER INFORMATION: cDNA for Insulin-Fc Fusion Protein

<400> SEQUENCE: 38

| | | | | | |
|---|---|---|---|---|---|
| atggaatgga | gctgggtctt | tctcttcttc | ctgtcagtaa | cgactggtgt | ccactccttc | 60 |
| gtgaaccagc | acctgtgcgg | ctcccacctg | gtggaagctc | tgtatctcgt | gtgcggcgag | 120 |
| cggggcttct | tctacacccc | caaggccgga | ggtggacctc | gacggggcat | cgtgaacag | 180 |
| tgctgcacct | ccatctgctc | cctgtaccag | ctggaaaact | actgcaatgg | cggaggtggt | 240 |
| tcaggaggcg | gtggacgctg | cactgacacc | cctccatgcc | ctgtgcccga | gcccctgggt | 300 |
| ggccccagcg | tactgatctt | cccaccgaaa | cccaaggaca | tcctgaggat | cacccgcacc | 360 |
| ccggaggtga | cctgcgtggt | gctggacctg | ggcaggagg | accccgaagt | gcaaatcagc | 420 |
| tggttcgtgg | acggaaagga | ggtgcacacc | gccaagaccc | aatcaaggga | gcagcagttc | 480 |
| aacggcacct | acagggtggt | gagcgtgttg | cccatagagc | accaggactg | gctgaccggc | 540 |
| aaggagttca | agtgccgcgt | gaaccacatt | gatctcccca | gccccatcga | gaggactatc | 600 |
| tccaaggccc | gagggagggc | ccacaagccc | agtgtatacg | tgctgccgcc | ctctccgaag | 660 |
| gaactgagct | ctagcgacac | cgtgagcatc | acctgcctga | tcaaggactt | ctaccctccc | 720 |
| gacatagacg | tagagtggca | gagcaacggc | cagcaggagc | ccgaaaggaa | gcacaggatg | 780 |
| accccaccc | aactggacga | ggacggctca | tactttcttt | atagcaagct | gagtgtggac | 840 |
| aagagcaggt | ggcagcaggg | cgacccttc | acttgcgccg | taatgcacga | gaccctgcag | 900 |
| aatcactaca | ccgacctgtc | actgagccat | agccccggat | ag | | 942 |

<210> SEQ ID NO 39
<211> LENGTH: 295
<212> TYPE: PRT
<213> ORGANISM: Artificial Sequence
<220> FEATURE:
<223> OTHER INFORMATION: Insulin-Fc Fusion Protein

<400> SEQUENCE: 39

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Ala Ala Ala
            20                  25                  30
```

```
Ala Ala Ala Ala Lys Gly Ile Val Glu Gln Cys Cys Thr Ser Ile Cys
             35                  40                  45
Ser Leu Tyr Gln Leu Glu Asn Tyr Cys Asn Gly Gly Gly Ser Gly
 50                  55                  60
Gly Gly Gly Arg Cys Thr Asp Thr Pro Pro Cys Pro Val Pro Glu Pro
 65                  70                  75                  80
Leu Gly Gly Pro Ser Val Leu Ile Phe Pro Pro Lys Pro Lys Asp Ile
                 85                  90                  95
Leu Arg Ile Thr Arg Thr Pro Glu Val Thr Cys Val Val Leu Asp Leu
            100                 105                 110
Gly Arg Glu Asp Pro Glu Val Gln Ile Ser Trp Phe Val Asp Gly Lys
            115                 120                 125
Glu Val His Thr Ala Lys Thr Gln Ser Arg Glu Gln Gln Phe Asn Gly
            130                 135                 140
Thr Tyr Arg Val Val Ser Val Leu Pro Ile Glu His Gln Asp Trp Leu
145                 150                 155                 160
Thr Gly Lys Glu Phe Lys Cys Arg Val Asn His Ile Asp Leu Pro Ser
                165                 170                 175
Pro Ile Glu Arg Thr Ile Ser Lys Ala Arg Gly Arg Ala His Lys Pro
            180                 185                 190
Ser Val Tyr Val Leu Pro Pro Ser Pro Lys Glu Leu Ser Ser Ser Asp
            195                 200                 205
Thr Val Ser Ile Thr Cys Leu Ile Lys Asp Phe Tyr Pro Pro Asp Ile
210                 215                 220
Asp Val Glu Trp Gln Ser Asn Gly Gln Gln Glu Pro Glu Arg Lys His
225                 230                 235                 240
Arg Met Thr Pro Pro Gln Leu Asp Glu Asp Gly Ser Tyr Phe Leu Tyr
                245                 250                 255
Ser Lys Leu Ser Val Asp Lys Ser Arg Trp Gln Gln Gly Asp Pro Phe
            260                 265                 270
Thr Cys Ala Val Met His Glu Thr Leu Gln Asn His Tyr Thr Asp Leu
            275                 280                 285
Ser Leu Ser His Ser Pro Gly
            290                 295
```

<210> SEQ ID NO 40
<211> LENGTH: 945
<212> TYPE: DNA
<213> ORGANISM: Artificial Sequence
<220> FEATURE:
<223> OTHER INFORMATION: cDNA for Insulin-Fc Fusion Protein

<400> SEQUENCE: 40

```
atggaatgga gctgggtctt tctcttcttc ctgtcagtaa cgactggtgt ccactccttc      60
gtgaaccagc acctgtgcgg ctcccacctg gtggaagctc tgtatctcgt gtgcggcgag     120
cggggcttct tctacacccc caaggctgcc gcagcagctg ccgctaaagg catcgtggaa     180
cagtgctgca cctccatctg ctccctgtac agctggaaaa actactgcaa tggcggaggt     240
ggttcaggag gcggtggacg ctgcactgac acccctccat gccctgtgcc cgagcccctg     300
ggtggcccca gcgtactgat cttcccaccg aaacccaagg acatcctgag gatcacccgc     360
accccggagg tgacctgcgt ggtgctggac ctgggcaggg aggaccccga agtgcaaatc     420
agctggttcg tggacggaaa ggaggtgcac accgccaaga cccaatcaag ggagcagcag     480
ttcaacggca cctacagggt ggtgagcgtg ttgcccatag agcaccagga ctggctgacc     540
```

```
ggcaaggagt tcaagtgccg cgtgaaccac attgatctcc ccagcccat cgagaggact    600 atctccaagg cccgagggag ggcccacaag cccagtgtat acgtgctgcc gccctctccg    660
aaggaactga gctctagcga caccgtgagc atcacctgcc tgatcaagga cttctaccct    720
cccgacatag acgtagagtg gcagagcaac ggccagcagg agcccgaaag gaagcacagg    780 atgacccac cccaactgga cgaggacggc tcatactttc tttatagcaa gctgagtgtg    840
gacaagagca ggtggcagca gggcgaccct ttcacttgcg ccgtaatgca cgagaccctg    900
cagaatcact acaccgacct gtcactgagc catagccccg gatag                    945
```

<210> SEQ ID NO 41
<211> LENGTH: 290
<212> TYPE: PRT
<213> ORGANISM: Artificial Sequence
<220> FEATURE:
<223> OTHER INFORMATION: Insulin-FC Fusion Protein

<400> SEQUENCE: 41

```
Phe Val Asn Gln His Leu Cys Gly Ser Asp Leu Val Glu Ala Leu Ala
  1               5                  10                  15

Leu Val Cys Gly Glu Arg Gly Phe Phe Tyr Thr Asp Pro Thr Gly Gly
             20                  25                  30

Gly Pro Arg Arg Gly Ile Val Glu Gln Cys Cys His Ser Ile Cys Ser
         35                  40                  45

Leu Tyr Gln Leu Glu Asn Tyr Cys Asn Gly Gly Gly Ala Gly Gly
     50                  55                  60

Gly Gly Asp Cys Pro Lys Cys Pro Ala Pro Glu Met Leu Gly Gly Pro
 65                  70                  75                  80

Ser Val Phe Ile Phe Pro Pro Lys Pro Lys Asp Thr Leu Leu Ile Ala
                 85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Asn Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
```

<210> SEQ ID NO 42
<211> LENGTH: 930
<212> TYPE: DNA
<213> ORGANISM: Artificial Sequence
<220> FEATURE:
<223> OTHER INFORMATION: cDNA for Insulin-Fc Fusion Protein

<400> SEQUENCE: 42

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggagactg ccccaagtgc ccgctcccg agatgctggg cggacccagc      300
gtgttcatct ccctcccaa gcccaaggac acactgctga tcgccaggac cccggaggtg      360
acctgcgtgg tggtggacct ggatcccgaa gaccccgagg tgcagatcag ctggttcgtg      420
gatggaaagc agatgcagac cgccaagacc caaccccggg aagagcagtt caacggcacc      480
tacagggtgg tgagtgtgtt gcccatcggc accaggact ggctgaaggg gaagcaattc      540
acatgcaagg ttaataacaa ggccctgccc agccccatcg agaggaccat cagcaaggcc      600
aggggccagg cccaccagcc atctgtgtac gtgctgcccc catctaggga ggaactgagc      660
aagaacacag tcagccttac ttgcctgatc aaggacttct tcccaccgga catagacgtg      720
gagtggcaga gtaacggcca gcaggagccc gagagcaagt ataggaccac ccgccccaa      780
ctggacgagg acggaagcta cttcctctac agcaaattga gcgttgacaa aagcaggtgg      840
cagcgaggcg acaccttcat ctgcgccgtg atgcacgagg cttt gcataa ccactacacc      900
caggagagcc tgtcccacag ccccggatag                                       930
```

<210> SEQ ID NO 43
<211> LENGTH: 291
<212> TYPE: PRT
<213> ORGANISM: Artificial Sequence
<220> FEATURE:
<223> OTHER INFORMATION: Insulin-Fc Fusion Protein

<400> SEQUENCE: 43

```
Phe Val Asn Gln His Leu Cys Gly Ser Asp Leu Val Glu Ala Leu Ala
  1               5                  10                  15

Leu Val Cys Gly Glu Arg Gly Phe Phe Tyr Thr Asp Pro Thr Gly Gly
             20                  25                  30

Gly Pro Arg Arg Gly Ile Val Glu Gln Cys Cys His Ser Ile Cys Ser
         35                  40                  45

Leu Tyr Gln Leu Glu Asn Tyr Cys Asn Gly Gly Gly Ala Gly Gly
     50                  55                  60

Gly Gly Cys Asn Asn Cys Pro Cys Pro Gly Cys Gly Leu Leu Gly Gly
 65                  70                  75                  80

Pro Ser Val Phe Ile Phe Pro Pro Lys Pro Lys Asp Ile Leu Val Thr
                 85                  90                  95

Ala Arg Thr Pro Thr Val Thr Cys Val Val Asp Leu Asp Pro Glu
            100                 105                 110

Asn Pro Glu Val Gln Ile Ser Trp Phe Val Asp Ser Lys Gln Val Gln
        115                 120                 125

Thr Ala Asn Thr Gln Pro Arg Glu Glu Gln Ser Asn Gly Thr Tyr Arg
```

```
                130                 135                 140
Val Val Ser Val Leu Pro Ile Gly His Gln Asp Trp Leu Ser Gly Lys
145                 150                 155                 160

Gln Phe Lys Cys Lys Val Asn Asn Lys Ala Leu Pro Ser Pro Ile Glu
                165                 170                 175

Glu Ile Ile Ser Lys Thr Pro Gly Gln Ala His Gln Pro Asn Val Tyr
                180                 185                 190

Val Leu Pro Pro Ser Arg Asp Glu Met Ser Lys Asn Thr Val Thr Leu
                195                 200                 205

Thr Cys Leu Val Lys Asp Phe Phe Pro Glu Ile Asp Val Glu Trp
        210                 215                 220

Gln Ser Asn Gly Gln Gln Glu Pro Glu Ser Lys Tyr Arg Met Thr Pro
225                 230                 235                 240

Pro Gln Leu Asp Glu Asp Gly Ser Tyr Phe Leu Tyr Ser Lys Leu Ser
                245                 250                 255

Val Asp Lys Ser Arg Trp Gln Arg Gly Asp Thr Phe Ile Cys Ala Val
                260                 265                 270

Met His Glu Ala Leu His Asn His Tyr Thr Gln Ile Ser Leu Ser His
                275                 280                 285

Ser Pro Gly
    290

<210> SEQ ID NO 44
<211> LENGTH: 933
<212> TYPE: DNA
<213> ORGANISM: Artificial Sequence
<220> FEATURE:
<223> OTHER INFORMATION: cDNA for Insulin-Fc Fusion Protein

<400> SEQUENCE: 44
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggatgcaa caactgcccg tgtccgggat gcggcctcct gggcggaccg     300
agcgtgttca ttttcccctcc taagcccaag gacattctgg tgaccgccag gaccccacg     360 gtgacctgcg tggtagtaga tctcgatccc gaaaacccag aggtgcaaat cagctggttc     420
gtggactcta gcaagtgca aaccgccaac acgcaaccc gcgaggaaca gagcaacggc     480
acctacaggg tggtgagcgt gctgcccatc gggcatcagg actggctgag cggcaagcag     540
tttaaatgca aggttaacaa caaggcactg cccagcccca tcgaggagat catcagcaag     600
acccccggga caggcccacca gcccaacgtg tacgtccttc ctccgagccg cgacgagatg     660
agcaagaaca ccgtgacgct gacctgtttg gtgaaggact cttcccacc cgagatcgac     720 gtggagtggc aaagcaatgg ccagcaggag cccgagagca aatacaggat gaccccaccc     780
caactggatg aggatggcag ctatttcctc tacagcaaat gtccgtgga caaaagcagg     840 tggcagaggg gcgacacctt catctgcgcc gtcatgcacg aggcccttca caatcactac     900
acccagatca gcctgagcca ctctcccgga tag                                  933

<210> SEQ ID NO 45
<211> LENGTH: 291
<212> TYPE: PRT
<213> ORGANISM: Artificial Sequence
```

<220> FEATURE:
<223> OTHER INFORMATION: Insulin-Fc Fusion Protein

<400> SEQUENCE: 45

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Cys Ile Ser Pro Cys Pro Val Pro Glu Ser Leu Gly Gly Pro
65              70                  75                  80

Ser Val Phe Ile Phe Pro Pro Lys Pro Lys Asp Ile Leu Arg Ile Thr
                85                  90                  95

Arg Thr Pro Glu Ile Thr Cys Val Val Leu Asp Leu Gly Arg Glu Asp
            100                 105                 110

Pro Glu Val Gln Ile Ser Trp Phe Val Asp Gly Lys Glu Val His Thr
        115                 120                 125

Ala Lys Thr Gln Pro Arg Glu Gln Gln Phe Asn Ser Thr Tyr Arg Val
    130                 135                 140

Val Ser Val Leu Pro Ile Glu His Gln Asp Trp Leu Thr Gly Lys Glu
145                 150                 155                 160

Phe Lys Cys Arg Val Asn His Ile Gly Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Pro Lys Glu Leu Ser Ser Ser Asp Thr Val Thr Leu
        195                 200                 205

Thr Cys Leu Ile Lys Asp Phe Phe Pro Pro Glu Ile Asp Val Glu Trp
    210                 215                 220

Gln Ser Asn Gly Gln Pro Glu Pro Glu Ser Lys Tyr His Thr Thr Ala
225                 230                 235                 240

Pro Gln Leu Asp Glu Asp Gly Ser Tyr Phe Leu Tyr Ser Lys Leu Ser
                245                 250                 255

Val Asp Lys Ser Arg Trp Gln Gln Gly Asp Thr Phe Thr Cys Ala Val
            260                 265                 270

Met His Glu Ala Leu Gln Asn His Tyr Thr Asp Leu Ser Leu Ser His
        275                 280                 285

Ser Pro Gly
    290
```

<210> SEQ ID NO 46
<211> LENGTH: 933
<212> TYPE: DNA
<213> ORGANISM: Artificial Sequence
<220> FEATURE:
<223> OTHER INFORMATION: cDNA for Insulin-Fc Fusion Protein

<400> SEQUENCE: 46

```
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct ctacaccga tcccactgga ggcggtccac gcagaggcat cgtgaacag       180 tgctgccact ccatctgctc cctgtaccag ctggaaaact actgcaatgg cggaggtggt    240
```

```
gcaggaggcg gtggatgcat cagcccctgc ccgtgccgg agagcctggg tggccctagc    300
gtgttcatat tccctcccaa gcccaaggac atcctgagga tcaccaggac cccgagatc    360 acctgtgtgg tgctggatct tggcagggaa gaccccgaag tccagatcag ctggttcgtg    420
gatggcaagg aggtgcacac cgccaagacc cagccgaggg agcagcagtt caactccacc    480
tacagggtgg tgagcgtgct gcctatcgag catcaggact ggctgaccgg caaagagttc    540
aagtgcaggg tgaaccacat cggcctgccc agcccatcg agaggaccat cagcaaagcc    600
aggggccagg cccaccagcc cagtgtgtac gtgcttcccc ctagcccaaa ggaactgagt    660
agcagcgata ccgtgaccct gacctgcctg atcaaggact ttttcccgcc agaaatagac    720
gtggagtggc agagcaacgg ccagccggag cccgagagca ataccacac caccgcccct    780 caactggacg aggacgggag ctacttcctg tatagcaagc tgagcgttga caagagcagg    840
tggcaacagg gcgacacctt cacctgcgcc gtgatgcacg aagctctgca aaaccactac    900
accgacctgt cactgagcca tagcccccgga tag                                933
```

`<210>` SEQ ID NO 47
`<211>` LENGTH: 290
`<212>` TYPE: PRT
`<213>` ORGANISM: Artificial Sequence
`<220>` FEATURE:
`<223>` OTHER INFORMATION: Insulin-Fc Fusion Protein

`<400>` SEQUENCE: 47

```
Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80

Ser Val Phe Ile Phe Pro Pro Lys Pro Lys Asp Thr Leu Leu Ile Ala
                85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
        115                 120                 125

Ala Lys Thr Gln Pro Arg Glu Glu Gln Phe Ser Gly Thr Tyr Arg Val
    130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
                165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Thr Val Ser Leu Thr
        195                 200                 205

Cys Leu Ile Lys Asp Phe Phe Pro Pro Asp Ile Asp Val Glu Trp Gln
    210                 215                 220

Ser Asn Gly Gln Gln Glu Pro Glu Ser Lys Tyr Arg Thr Thr Pro Pro
225                 230                 235                 240
```

```
Gln Leu Asp Glu Asp Gly Ser Tyr Phe Leu Tyr Ser Lys Leu Ser Val
                245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
        275                 280                 285

Pro Gly
    290

<210> SEQ ID NO 48
<211> LENGTH: 930
<212> TYPE: DNA
<213> ORGANISM: Artificial Sequence
<220> FEATURE:
<223> OTHER INFORMATION: cDNA for Insulin-Fc Fusion Protein

<400> SEQUENCE: 48
atggaatgga gctgggtctt tctcttcttc ctgtcagtaa cgactggtgt ccactccttc      60
gtgaaccagc acctgtgcgg ctccgacctg gtggaagctc tggctctcgt gtgcggcgag     120
cggggcttct tctacaccga tcccactgga ggcggtccac gcagaggcat cgtggaacag     180
tgctgccact ccatctgctc cctgtaccag ctggaaaact actgcaatgg cggaggtggt     240
gcaggaggcg gtggagactg ccccaagtgc cccgctcccg agatgctggg cggacccagc     300
gtgttcatct tccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt cagcggcacc     480
tacagggtgg tgagtgtgtt gcccatcggc accaggact ggctgaaggg gaagcaattc     540
acatgcaagg ttaataacaa ggccctgccc agccccatcg agaggaccat cagcaaggcc     600
aggggccagg cccaccagcc atctgtgtac gtgctgcccc catctaggga ggaactgagc     660
aagaacacag tcagccttac ttgcctgatc aaggacttct tcccaccgga catagacgtg     720
gagtggcaga gtaacggcca gcaggagccc gagagcaagt ataggaccac accgccccaa     780
ctggacgagg acggaagcta cttcctctac agcaaattga gcgttgacaa agcaggtgg     840 cagcgaggcg acaccttcat ctgcgccgtg atgcacgagg ctttgcataa ccactacacc     900
caggagagcc tgtcccacag ccccggatag                                      930

<210> SEQ ID NO 49
<211> LENGTH: 290
<212> TYPE: PRT
<213> ORGANISM: Artificial Sequence
<220> FEATURE:
<223> OTHER INFORMATION: Insulin-Fc Fusion Protein

<400> SEQUENCE: 49

Phe Val Asn Gln His Leu Cys Gly Ser His Leu Val Glu Ala Leu Ala
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn Gly Gly Gly Ala Gly Gly
    50                  55                  60

Gly Gly Asp Cys Pro Lys Cys Pro Ala Pro Glu Met Leu Gly Gly Pro
65                  70                  75                  80
```

Ser Val Phe Ile Phe Pro Pro Lys Pro Lys Asp Thr Leu Leu Ile Ala
            85                  90                  95

Arg Thr Pro Glu Val Thr Cys Val Val Val Asp Leu Asp Pro Glu Asp
            100                 105                 110

Pro Glu Val Gln Ile Ser Trp Phe Val Asp Gly Lys Gln Met Gln Thr
            115                 120                 125

Ala Lys Thr Gln Pro Arg Glu Glu Gln Phe Gln Gly Thr Tyr Arg Val
            130                 135                 140

Val Ser Val Leu Pro Ile Gly His Gln Asp Trp Leu Lys Gly Lys Gln
145                 150                 155                 160

Phe Thr Cys Lys Val Asn Asn Lys Ala Leu Pro Ser Pro Ile Glu Arg
            165                 170                 175

Thr Ile Ser Lys Ala Arg Gly Gln Ala His Gln Pro Ser Val Tyr Val
            180                 185                 190

Leu Pro Pro Ser Arg Glu Glu Leu Ser Lys Asn Thr Val Ser Leu Thr
            195                 200                 205

Cys Leu Ile Lys Asp Phe Phe Pro Pro Asp Ile Asp Val Glu Trp Gln
            210                 215                 220

Ser Asn Gly Gln Gln Glu Pro Glu Ser Lys Tyr Arg Thr Thr Pro Pro
225                 230                 235                 240

Gln Leu Asp Glu Asp Gly Ser Tyr Phe Leu Tyr Ser Lys Leu Ser Val
            245                 250                 255

Asp Lys Ser Arg Trp Gln Arg Gly Asp Thr Phe Ile Cys Ala Val Met
            260                 265                 270

His Glu Ala Leu His Asn His Tyr Thr Gln Glu Ser Leu Ser His Ser
            275                 280                 285

Pro Gly
    290

<210> SEQ ID NO 50
<211> LENGTH: 930
<212> TYPE: DNA
<213> ORGANISM: Artificial Sequence
<220> FEATURE:
<223> OTHER INFORMATION: cDNA for Insulin-Fc Fusion Protein

<400> SEQUENCE: 50 atgaatgga gctgggtctt tctcttcttc ctgtcagtaa cgactggtgt ccactccttc        60
gtgaaccagc acctgtgcgg ctcccacctg gtggaagctc tggctctcgt gtgcggcgag      120
cggggcttct tctacaccga tcccactgga ggcggtccac gcagaggcat cgtgaacag       180 tgctgcacct ccatctgctc cctgtaccag ctggaaaact actgcaatgg cggaggtggt      240
gcaggaggcg gtgagactg ccccaagtgc cccgctcccg agatgctggg cggacccagc      300
gtgttcatct tccctcccaa gcccaaggac acactgctga tcgccaggac cccggaggtg     360
acctgcgtgg tggtggacct ggatcccgaa gaccccgagg tgcagatcag ctggttcgtg     420
gatggaaagc agatgcagac cgccaagacc caaccccggg aagagcagtt ccaaggcacc     480
tacagggtgg tgagtgtgtt gcccatcggc caccaggact ggctgaaggg gaagcaattc     540
acatgcaagg ttaataacaa ggccctgccc agccccatcg agaggaccat cagcaaggcc    600
aggggccagg cccaccagcc atctgtgtac gtgctgcccc catctaggga ggaactgagc     660
aagaacacag tcagccttac ttgcctgatc aaggacttct tcccaccgga catagacgtg      720
gagtggcaga gtaacggcca gcaggagccc gagagcaagt ataggaccac accgccccaa    780

```
ctggacgagg acggaagcta cttcctctac agcaaattga gcgttgacaa aagcaggtgg    840
cagcgaggcg acaccttcat ctgcgccgtg atgcacgagg ctttgcataa ccactacacc    900
caggagagcc tgtcccacag ccccggatag                                     930
```

<210> SEQ ID NO 51
<211> LENGTH: 289
<212> TYPE: PRT
<213> ORGANISM: Artificial Sequence
<220> FEATURE:
<223> OTHER INFORMATION: Insulin-Fc Fusion Protein

<400> SEQUENCE: 51

Phe Val Asn Gln His Leu Cys Gly Ser Asp Leu Val Glu Ala Leu Ala
1               5                   10                  15

Leu Val Cys Gly Glu Arg Gly Phe Phe Tyr Thr Asp Pro Thr Gly Gly
                20                  25                  30

Gly Pro Arg Arg Gly Ile Val Glu Gln Cys Cys His Ser Ile Cys Ser
            35                  40                  45

Leu Tyr Gln Leu Glu Asn Tyr Cys Asn Gly Gly Gly Ala Gly Gly
    50                  55                  60

Gly Gly Cys Pro Lys Cys Pro Ala Pro Glu Met Leu Gly Gly Pro Ser
65                  70                  75                  80

Val Phe Ile Phe Pro Pro Lys Pro Lys Asp Thr Leu Leu Ile Ala Arg
                85                  90                  95

Thr Pro Glu Val Thr Cys Val Val Asp Leu Asp Pro Glu Asp Pro
            100                 105                 110

Glu Val Gln Ile Ser Trp Phe Val Asp Gly Lys Gln Met Gln Thr Ala
        115                 120                 125

Lys Thr Gln Pro Arg Glu Glu Gln Phe Lys Gly Thr Tyr Arg Val Val
130                 135                 140

Ser Val Leu Pro Ile Gly His Gln Asp Trp Leu Lys Gly Lys Gln Phe
145                 150                 155                 160

Thr Cys Lys Val Asn Asn Lys Ala Leu Pro Ser Pro Ile Glu Arg Thr
                165                 170                 175

Ile Ser Lys Ala Arg Gly Gln Ala His Gln Pro Ser Val Tyr Val Leu
            180                 185                 190

Pro Pro Ser Arg Glu Glu Leu Ser Lys Asn Thr Val Ser Leu Thr Cys
        195                 200                 205

Leu Ile Lys Asp Phe Phe Pro Pro Asp Ile Asp Val Glu Trp Gln Ser
210                 215                 220

Asn Gly Gln Gln Glu Pro Glu Ser Lys Tyr Arg Thr Thr Pro Pro Gln
225                 230                 235                 240

Leu Asp Glu Asp Gly Ser Tyr Phe Leu Tyr Ser Lys Leu Ser Val Asp
                245                 250                 255

Lys Ser Arg Trp Gln Arg Gly Asp Thr Phe Ile Cys Ala Val Met His
            260                 265                 270

Glu Ala Leu His Asn His Tyr Thr Gln Glu Ser Leu Ser His Ser Pro
        275                 280                 285

Gly

<210> SEQ ID NO 52
<211> LENGTH: 927
<212> TYPE: DNA
<213> ORGANISM: Artificial Sequence
<220> FEATURE:
<223> OTHER INFORMATION: cDNA for Insulin-Fc Fusion Protein

```
<400> SEQUENCE: 52
atggaatgga gctgggtctt tctcttcttc ctgtcagtaa cgactggtgt ccactccttc    60
gtgaaccagc acctgtgcgg ctccgacctg gtggaagctc tggctctcgt gtgcggcgag   120
cggggcttct tctacaccga tcccactgga ggcggtccac gcagaggcat cgtggaacag   180
tgctgccact ccatctgctc cctgtaccag ctggaaaact actgcaatgg cggaggtggt   240
gcaggaggcg gtggatgccc caagtgcccc gctcccgaga tgctgggcgg acccagcgtg   300
ttcatcttcc ctcccaagcc caaggacaca ctgctgatcg ccaggacccc ggaggtgacc   360
tgcgtggtgg tggacctgga tcccgaagac cccgaggtgc agatcagctg gttcgtggat   420
ggaaagcaga tgcagaccgc caagacccaa ccccgggaag agcagttcaa aggcacctac   480
agggtggtga gtgtgttgcc catcggccac caggactggc tgaagggaa gcaattcaca    540 tgcaaggtta ataacaaggc cctgcccagc cccatcgaga ggaccatcag caaggccagg   600
ggccaggccc accagccatc tgtgtacgtg ctgcccccat ctaggagga actgagcaag    660 aacacagtca gccttacttg cctgatcaag gacttcttcc caccggacat agacgtggag   720
tggcagagta acggccagca ggagcccgag agcaagtata ggaccacacc gccccaactg   780
gacgaggacg gaagctactt cctctacagc aaattgagcg ttgacaaaag caggtggcag   840
cgaggcgaca ccttcatctg cgccgtgatg cacgaggctt tgcataacca ctacacccag   900
gagagcctgt cccacagccc cggatag                                       927

<210> SEQ ID NO 53
<211> LENGTH: 57
<212> TYPE: DNA
<213> ORGANISM: Artificial Sequence
<220> FEATURE:
<223> OTHER INFORMATION: Leader Sequence cDNA

<400> SEQUENCE: 53
atggaatgga gctgggtctt tctcttcttc ctgtcagtaa cgactggtgt ccactcc       57

<210> SEQ ID NO 54
<211> LENGTH: 19
<212> TYPE: PRT
<213> ORGANISM: Artificial Sequence
<220> FEATURE:
<223> OTHER INFORMATION: Leader Sequence

<400> SEQUENCE: 54

Met Glu Trp Ser Trp Val Phe Leu Phe Phe Leu Ser Val Thr Thr Gly
 1               5                  10                  15

Val His Ser
```